United States Patent
Wagner, Jr.

(10) Patent No.: US 6,329,147 B1
(45) Date of Patent: Dec. 11, 2001

(54) METHODS FOR DETECTION OF A TRIPLET REPEAT BLOCK AND A FUNCTIONAL MISMATCH BINDING PROTEIN IN A BIOLOGICAL FLUID SAMPLE

(75) Inventor: Robert E. Wagner, Jr., Fort Collins, CO (US)

(73) Assignee: ValiGen (US), Inc., Newton, PA (US)

( * ) Notice: Subject to any disclaimer, the term of this patent is extended or adjusted under 35 U.S.C. 154(b) by 0 days.

(21) Appl. No.: 09/497,933

(22) Filed: Feb. 4, 2000

Related U.S. Application Data

(60) Division of application No. 08/608,016, filed on Mar. 4, 1996, now Pat. No. 6,120,992, which is a continuation-in-part of application No. 08/431,081, filed on Apr. 28, 1995, now Pat. No. 6,114,115, which is a continuation-in-part of application No. 08/147,785, filed on Nov. 4, 1993, now Pat. No. 6,027,877.

(51) Int. Cl.[7] .............................. C12Q 1/68; G01N 33/53; G01N 33/566; C12P 19/34; C07K 1/00
(52) U.S. Cl. ........................ 435/6; 435/91.2; 435/7.1; 436/501; 530/350
(58) Field of Search .................... 435/6, 91.2, 810, 435/7.1; 530/350; 424/484, 486, 488, 489; 436/501

(56) References Cited

U.S. PATENT DOCUMENTS

| | | | |
|---|---|---|---|
| 5,175,343 | * 12/1992 | Fritzberg et al. | 560/145 |
| 5,459,039 | 10/1995 | Modrich et al. | 435/6 |
| 5,556,750 | 9/1996 | Modrich et al. | 435/6 |
| 5,679,522 | 10/1997 | Modrich et al. | 435/6 |
| 5,702,894 | 12/1997 | Modrich et al. | 435/6 |
| 5,750,335 | 5/1998 | Gifford | 435/6 |
| 5,858,754 | 1/1999 | Modrich et al. | 435/195 |
| 5,861,482 | 1/1999 | Modrich et al. | 530/350 |
| 6,027,877 | 2/2000 | Wagner, Jr. | 435/6 |

FOREIGN PATENT DOCUMENTS

| | | |
|---|---|---|
| 0 333 465 | 9/1989 | (EP) . |
| WO 91/02083 | 2/1991 | (WO) . |
| WO 93/02216 | 2/1993 | (WO) . |
| WO 93/22457 | 11/1993 | (WO) . |

OTHER PUBLICATIONS

Alani E, Chi NW, Kolodner R, 1995, "The *Saccharomyces cerevisiae* Msh2 protein specifically binds to duplex oligonucleotides containing mismatched DNA base pairs and insertions", Genes Dev. Jan. 15, 1995;9(2):234–47.

Au et al., 1987, "Enzymology of methyl–Directed DNA Mismatch Correction", Genetics Society of America, San Francisco, CA, Jun. 13–16, 1987, Genetics 116 (1 part 2), p. vi.

(List continued on next page.)

*Primary Examiner*—Carla J. Myers
*Assistant Examiner*—Diana Johannsen
(74) *Attorney, Agent, or Firm*—Pennie & Edmonds LLP

(57) ABSTRACT

A method for detecting mutations, such as a single base change or an addition or deletion of about one to four base pairs, is based on the use of an immobilized DNA mismatch-binding protein, such as MutS, which binds to a nucleic acid hybrid having a single base mismatch or unpaired base or bases, thereby allowing the detection of mutations involving as little as one base change in a nucleotide sequence. Such a method is useful for diagnosing a variety of important disease states or susceptibilities, including the presence of a mutated oncogene and the presence of DNA containing triplet repeat sequences which characterize several genetic diseases including fragile X syndrome. The present method is used to isolate or remove by affinity chromatography duplex DNA molecules containing mismatches such as error-containing molecules in PCR-amplified DNA samples. Methods for detecting and enriching minority sequences are disclosed. Also provided are compositions and kits useful for practicing the methods of the present invention.

91 Claims, 19 Drawing Sheets

OTHER PUBLICATIONS

Au et al., 1988, "Enzymology of E. coli methyl–directed mismatch correction", UCLA Symp. abstracts, Taos, NM, Jan. 24–30, 1988, J. Cell. Biochem. Suppl. 0 (12 part A), p. 235.

Bhattacharyya NP, Skandalis A, Ganesh A, Groden J, Meuth M, 1994, "Mutator phenotypes in human colorectal carcinoma cell lines", Proc Natl Acad Sci USA. Jul. 5, 1994;91(14):6319–23.

Bowen et al., 1979, "The Detection of DNA–Binding Proteins by Protein Blotting", Nucl. Acids Res. 8:1–20.

Bronner CE, Baker SM, Morrison PT, Warren G, Smith LG, Lescoe MK, Kane M, Earabino C, Lipford J, Lindblom A et al., 1994, "Mutation in the DNA mismatch repair gene homologue hMLH1 is associated with hereditary non–polyposis colon cancer", Nature. Mar. 17, 1994;368(6468):258–61.

Butler, 1992, "The Behavior of Antigens and Antibodies Immobilized on a Solid Phase", in: *Structure of Antigens*, van Regenmortel, ed., CRC Press, Boca Raton, pp. 209–259.

Butler et al., 1992, The Physical and Functional Behavior of Capture Antibodies Adsorbed on Polystyrene, J. Immunol. Meth. 150:77–90.

Butler et al., 1993, "The Immunochemistry of Sandwich ELISA's—VI. Greater than 90% of Monoclonal and 75% of Polyclonal Anti–Fluorescyl Capture Antibodies (Cabs) Are Detected by Passive Adsorption", Mol. Immunol. 30:1165–1175.

Cotton et al., 1988, "Reactivity of Cytosine and Thymine in Single Base–Pair Mismatches with Hydroxylamine and Osmium Tetroxide and Its Application to the Study Mutations", Proc. Natl. Acad. Sci. USA 85:4397–4401.

Cotton et al., 1989, "Chemical Reactivity of Matched Cytosine and Thymine Bases Near Mismatched and Unmatched Bases in a Heteroduplex between DNA Strands with Multiple Differences", Nucl. Acids Res. 17:4223–4233.

Dohet et al., 1987, "Large Non–Homology in Heteroduplex DNA is Processed Differently than Single Base Pair Mismatches", Mol. Gen. Genet. 206:181–184.

Fazakerley GV, Quignard E, Woisard A, Guschlbauer W, van der Marel GA, van Boom JH, Jones M, Radman M, 1986, "Structures of mismatched base pairs in DNA and their recognition by the *Escherichia coli* mismatch repair system", EMBO J. Dec. 20, 1986;5(13):3697–703.

Fishel R, Ewel A, Lescoe MK, 1994, "Purified human MSH2 protein binds to DNA containing mismatched nucleotides", Cancer Res. Nov. 1, 1994;54(21):5539–42.

Fishel R, Ewel A, Lee S, Lescoe MK, Griffith J, 1994, "Binding of mismatched microsatellite DNA sequences by the human MSH2 protein", Science. Nov. 25, 1994;266(5189):1403–5.

Fisel R, Lescoe MK, Rao MR, Copeland NG, Jenkins NA, Garber J, Kane M, Kolodner R, 1993, "The human mutator gene homolog MSH2 and its association with hereditary nonpolyposis colon cancer", Cell. Dec. 3, 1993;75(5):1027–38.

Flytzanis CN, 1994, "DNA binding of immobilized proteins" in *Protein Blotting: A Practical Approach*, Dunbar, BS (ed.), Oxford University Press, Inc., New York, pp. 163–168.

Fujii et al., 1989, "Isolation and Characterization of cDNA Clones Derived from the Divergently Transcribed Gene in the Region Upstream from the Human Dihydrofolate Reductase Gene", J. Biol. Chem. 264:10057–10064.

Gibbs et al., 1987, "Identification and Localization of Mutations at the Lesch–Nyhan Locus by Ribonuclease A Cleavage", Science 236:303–305.

Grompe et al., 1989, "Scanning Detection of Mutations in Human Ornithine Transcarbamoylase by Chemical Mismatch Cleavage", Proc. Natl. Acad. Sci USA 86:5888–5892.

Haber et al., 1988, "Nucleotide Sequence of the *Salmonella typhimurium* mutS Gene Required for Mismatch Repair: Homology of MutS and HexA of *Streptococcus pneumoniae*", J. Bacteriol. 170:197–202.

Hughes et al., 1992, "The Purification of a Human Mismatch–Binding Protein and Identification of Its Associated ATPase and Helicase Activities", J. Biol. Chem. 267:23876–23882.

Jiricny et al., 1988, "Mismatch–Containing Oligonucleotide Duplexes Bound by the *E. coli* mutS–Encoded Protein", Nucl. Acids Res. 16:7843–7853

Jiricny et al., 1988, "The Purification of a G–T Mismatch Binding Protein from Hela Cells", UCLA Symp. abstracts, Taos, NM, Jan. 24–30, 1988, J. Cell. Biochem. Suppl. 0 (12 part A), p. 267.

Jiricny et al., 1988, "Correlation Between the Substrate Specificity of a Hela Mismatch Binding Protein and the Efficiency of Mismatch Repair in Vivo" in *Mechanisms and Consequences of DNA Damage Processing*, Alan R. Liss, Inc., pp. 273–277.

Jones et al., 1987, "Repair of a Mismatch is Influenced by the Base Composition of the Surrounding Nucleotide Sequence", Genetics 115:605–610.

Karran et al., 1990, "Mismatch Binding Proteins and Tolerance to Alkylating Agents in Human Cells", Mutat. Res. 236:269–275.

Keller et al., 1991, "Selection of Sequences Recognized by a DNA Binding Protein Using a Preparative Southwestern Blot", Nucl. Acids Res. 19:4675–4680.

Lahue et al., 1987, "Analysis of Methyl–directed Mismatch Repair In Vitro", in *DNA Replication and Recombination*, Alan R. Liss, Inc., pp. 125–134.

Lahue et al., 1988, "Methyl–Directed DNA Mismatch Repair in *Escherichia coli* in vitro", Mutat. Res. 198:37–43.

Lahue et al., 1989, "DNA Mismatch Correction in a Defined System", Science 245:160–164.

Leach FS, Nicolaides NC, Papadopoulos N, Liu B, Jen J, Parsons R, Peltomaki P, Sistonen P, Aaltonen LA, Nystrom–Lahti M et al., 1993, "Mutations of a mutS homolog in hereditary nonpolyposis colorectal cancer", Cell. Dec. 17, 1993;75(6):1215–25.

Lew et al., 1993, "Affinity Selection of Polymerase Chain Reaction Products by DNA Binding Proteins", Meth. Enzymol. 218:526–534.

Linton et al., 1989, "Dual Bidirectional Promoters at the Mouse dhfr Locus: Cloning and Characterization of two mRNA Classes of the Divergently Transcribed Rep–1 Gene", Mol. Cell. Biol. 7:3058–3072.

Lishanskaya et al., 1992, "Mutation Detection in the Cystic Fibrosis Gene Using an *E. coli* Mismatched Binding Protein MutS", Am. J. Hum. Genet. 51(4 Suppl.):A385 (Abstract # 1517).

Lishanski A, Ostrander EA, Rine J, 1994, "Mutation detection by mismatch binding protein, MutS, in amplified DNA: application to the cystic fibrosis gene", Proc Natl Acad Sci U S A. Mar. 29, 1994;91(7):2674–8.

Lu et al., 1988, "Repair of Single Base–Pair Transversion Mismatches of *Escherichia coli* in vitro: Correction of Certain A/G Mismatches is Independent of dam Methylation and Host mutHLS Gene Functions", Genetics 118:593–600.

Lu et al., 1992, "Detection of Single DNA Base Mutations with Mismatch Repair Enzymes", Genomics 14:249–255.

Meyer et al., 1990, "The Single–Stranded DNA–Binding Protein of *Escherichia coli*", Microbiol. Rev. 54:342–380.

Miret et al., 1993, "Characterization of a DNA Mismatch–Binding Activity in Yeast Extracts", J. Biol. Chem. 268:3507–3513.

Miskimins et al., 1985, "Use of a Protein–Blotting Procedure and a Specific DNA Probe to Identify Nuclear Proteins that Recognize the Promoter Region of the Transferrin Receptor Gene", Proc. Natl. Acad. Sci. USA 82:6741–6744.

Modrich, 1989, "Methyl–Directed DNA Mismatch Correction", J. Biol. Chem. 264:6597–6600.

Modrich P and Lahue R, 1996, "Mismatch repair in replication fidelity, genetic recombination, and cancer biology", Annu Rev Biochem. 1996;65:101–33.

Myers et al., 1986, "Recent Advances in the Development of Methods for Detecting Single–Base Substitutions Associated with Human Genetic Diseases", Cold Spring Harbor Symp. Quant. Biol. 51:275–284.

Nelson SF, McCusker JH, Sander MA, Kee Y, Modrich P, Brown PO, 1993, "Genomic mismatch scanning: a new approach to genetic linkage mapping", Nat Genet. May 1994;4(1):11–8.

New L, Liu K, Crouse GF, 1993, "The yeast gene MSH3 defines a new class of eukaryotic MutS homologues", Mol Gen Genet. May 1993;239(1–2):97–108.

Norby et al., 1992, "Determination of Recognition Sequences for DNA–Binding Proteins by a Polymerase Chain Reaction–Assisted Binding Site Selection Method (BSS) Using Nitrocellulose Immobilized DNA Binding Protein", Nucl. Acids Res. 20:6317–6321.

Oliphant et al., 1989, "Defining the Sequence Specificity of DNA–Binding Proteins by Selecting Binding Sites from Random–Sequence Oligonucleotides: Analysis of Yeast GCN4 Protein", Mol. Cell. Biol. 9:2944–2949.

Pang et al., 1985, "Identification and Characterization of the mutL and mutS Gene Products of *Salmonella typhimurium* LT2", J. Bacteriol. 163:1007–1015.

Parker B and Marinus MG, 1992, "Repair of DNA Heteroduplexes Containing Small Heterologous Sequences in *Escherichia coli*", Proc. Natl. Acad. Sci. USA 89:1730–1734.

Perrino et al., 1988, "Interaction of a Folded Chromosome–Associated Protein with Single Stranded DNA–Binding Protein of *Escherichia coli* Identified by Affinity Chromatography", J. Biol. Chem. 263:11833–11839.

Priebe et al., 1988, "Nucleotide Sequence of the hexA Gene for DNA Mismatch Repair in *Streptococcus pneumoniae* and Homology of hexA to mutS of *Escherichia coli* and *Salmonella typhimurium*", J. Bacteriol. 170:190–196.

Radman et al., 1986, "Mismatch Repair in *Escherichia coli*", Annu. Rev. Genet. 20:523–538.

Radman et al., 1988, "The High Fidelity of DNA Duplication", Sci. Amer. Aug. 1988:40–46.

Reenen et al., 1993, "Isolation and Characterization of two *Saccharomyces cerevisiae* Genes Encoding Homologs of the Bacterial HexA and MutS Mismatch Repair Proteins", Genetics 132:963–973.

Reenen et al., 1993, "Characterization of Insertion Mutations in the *Saccharomyces cerevisiae* MSH1 and MSH2 Genes: Evidence for Separate Mitochondrial and Nuclear Functions", Genetics 132:975–985.

Saiki et al., 1989, "Genetic Analysis of Amplified DNA. With Immobilized Sequence–Specific Oligonucleotide Probes", Proc. Natl. Acad. Sci. USA 86:6230–6234.

Seed, 1982, "Attachment of Nucleic Acids to Nitrocellulose and Diazonium–Substituted Supports", in: *Genetic Engineering*, vol. 4, Setlow et al., eds., Plenum Press, NY, NY, pp. 91–102.

Shimada et al., 1989, "A 165 Base Pair Sequence between the Dihydrofolate Reductase Gene and the Divergently Transcribed Upstream Gene is Sufficient for Bidirectional Transcriptional Activity", J. Biol. Chem. 264:20171–20174.

Singh et al., 1988, "Molecular Cloning of an Enhancer Binding Protein: Isolation by Screening of an Expression Library with a Recognition Site DNA", Cell 52:415–423.

Singh et al., 1989, "Molecular Cloning of Sequence–Specific DNA Binding Proteins Using Recognition Site Probes", BioTechniques 7:252–261.

Stephenson et al., 1989, "Selective Binding to DNA Base Pair Mismatches by Proteins from Human Cells", J. Bio. Chem. 264:21177–21182.

Su et al., 1988, "Mispair Specificity of Methyl–Directed DNA Mismatch Correction in vitro", J. Biol. Chem. 263:6829–6835.

Takamatsu S, Kato R, Kuramitsu S, 1996, "Mismatch DNA recognition protein from an extremely thermophilic bacterium, Thermus thermophilus HB8", Nucleic Acids Res. Feb. 15, 1996;24(4):640–7.

Towbin et al., 1984, "Immunoblotting and Dot–Immunobinding—Current Status and Outlook", J. Immunol. Meth. 72:313–340.

Valle et al., 1991, "The Sequence of a 6,3 kb Segment of Yeast Chromosome III Reveals an Open Reading Frame Coding for a Putative Mismatch Binding Protein", Yeast 7:981–988.

Vinson et al., 1988, "In situ Detection of Sequence–Specific DNA Binding Activity Specified by a Recombinant Bacteriophage", Genes & Devel. 2:801–808.

Wagner R, Debbie P, Radman M., 1995, "Mutation detection using immobilized mismatch binding protein (MutS)", Nucleic Acids Res. Oct. 11, 1995;23(19):3944–8.

* cited by examiner

TRIPLET REPEAT DIAGNOSTIC

I. To detect repeat block larger than probe repeat block (Disease diagnostic):

Probe: (CCG or CAG repeat)

*BxxxxxxxxxxCCGCCGCCGCCGCCGCCGCCGCCGCCGCCGCCGCCGCCGCCGCCGnnnnnnnnnn
Repeat block smaller than smallest block to be detected. (SEQ ID NO: 18)

A. Test repeat block smaller than probe repeat block.

```
                                                              (SEQ ID NO: 19)
         xxxxxxxxxGGCGGCGGCGGCGGCGGCGGCGGCGGCGGCnnnnnnnnnn     Test
        *BxxxxxxxxxxCCGCCGCCGCCGCCGCCGCCGCCGCCGCCGCCGnnnnnnnnnn Probe
                         CG                                    (SEQ ID NO: 18)
                       C    C
                      G      C
                     C        G
                    C          C
                     G        C
                      C      C
                       C C G
```

MutS does NOT recognize this duplex.

B. Test repeat block larger than probe repeat block:

```
                       CG
                       GG
                       GC
                       CG
                       GG
                       GC
                       CG
                       GG                    (SEQ ID NO: 20)
                       GC                         Test
  xxxxxxxxxGGCGGCGGCGGCGGCGGCGGCGGCGGCGGCGGCGGCGGCGGCGGCnnnnnnnnnn
 *BxxxxxxxxxxCCGCCGCCGCCGCCGCCGCCGCCGCCGCCGCCGCCGCCGCCGCCGnnnnnnnnnn
                                                   Probe
      MutS DOES recognize this duplex.    (SEQ ID NO: 18)
```

FIG.12A

II. To detect repeat block smaller than probe repeat block:

Probe: (CGG or CTG repeat)

\* BxxxxxxxxxCGGCGGCGGCGGCGGCGGCGGCGGCGGCGGCGGCGGCGGCGGnnnnnnnnn (SEQ ID NO: 21)

Repeat block larger than largest block to be detected.

A. Test repeat block smaller than probe repeat block.

```
         xxxxxxxxxCCGCCGCCGCCGCCGCCGCCGCCGCCGnnnnnnnnn   Test    (SEQ ID NO: 22)
       * BxxxxxxxxxGGCGGCGGCGGCGGCGGCGGCGGCGGCnnnnnnnnn   Probe   (SEQ ID NO: 23)
                                    GC
                                    GG
                                    CG
                                    GC
                                    GG
                                    CG
                                    GC
                                    GG
                                    CG
```

MutS DOES recognize this duplex.

B. Test repeat block larger than probe repeat block.

```
                    G C C
                  C       G
                C           C
                G           C
                C           G
                  C  C
                    GC
xxxxxxxxxGCCGCCGCCGCCGCCGCCGCCGCCGCCGCCGCCGCCGCCGCCGCCnnnnnnnnn    Test    (SEQ ID NO: 24)
*BxxxxxxxxxCGGCGGCGGCGGCGGCGGCGGCGGCGGCGGCGGCGGCGGCGGnnnnnnnnn     Probe   (SEQ ID NO: 25)
```

MutS does NOT recognize this duplex.

FIG.12B

SEQUENCE LISTING

<160> NUMBER OF SEQ ID NOS: 25

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Probe

<400> SEQUENCE: 1
gcacctgact cctggggaga agtctgccgt                            30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Probe

<400> SEQUENCE: 2
cgtggactga ggacccctct tcagacggca                            30

<210> SEQ ID NO 3
<211> LENGTH: 30
<212> TYPE: DNA
<213> ORGANISM: Artificial Sequence
<220> FEATURE:

<223> OTHER INFORMATION: Description of Artificial Sequence: Probe

<400> SEQUENCE: 3
acggcagact tctcctcagg agtcaggtgc            30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Probe

<400> SEQUENCE: 4
gcacctgact cctgtggaga agtctgccgt            30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Probe

<400> SEQUENCE: 5
acggcagact tctccgcagg agtcaggtgc            30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Probe

<400> SEQUENCE: 6
gcacctgact cctgcggaga agtctgccgt            30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Probe

<400> SEQUENCE: 7
gcacctgact cctgaggaga agtctgccgt            30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Probe

<400> SEQUENCE: 8
acggcagact tctccacagg agtcaggtgc            30

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Probe

<400> SEQUENCE: 9
acggcagact tctcccccag gagtcaggtg c            31

```
<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Probe

<400> SEQUENCE: 10
acggcagact tctccaccca ggagtcaggt gc                           32

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Probe

<400> SEQUENCE: 11
acggcagact tctccgaccc aggagtcagg tgc                          33

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: Probe

<400> SEQUENCE: 12
acggcagact tctccggacc caggagtcag gtgc                         34

<210> SEQ ID NO 13
<211> LENGTH: 100
<212> TYPE: DNA
<213> ORGANISM: Artificial Sequence
<220> FEATURE:
<223> OTHER INFORMATION: Description of Artificial Sequence: Probe

<400> SEQUENCE: 13
gcactaactt cagggtgatg ctggtgaagg tgggagaagg tgaggagggg cagtggagcg    60
tgaagaccaa agaccagatg atgaggtagg ggctcctgcg                         100

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Probe

<400> SEQUENCE: 14
gcactaactt cagggtgatg                                        20

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 15
gcgtcctcgg ggatgagta                                         19

<210> SEQ ID NO 16
<211> LENGTH: 18
<212> TYPE: DNA
<213> ORGANISM: Artificial Sequence
<220> FEATURE:
```

<223> OTHER INFORMATION: Description of Artificial Sequence: Probe

<400> SEQUENCE: 16
gaaggtgatg agacggat                                           18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Probe

<400> SEQUENCE: 17
cccaggagat tctgtctc                                           18

<210> SEQ ID NO 18
<211> LENGTH: 63
<212> TYPE: DNA
<213> ORGANISM: Artificial Sequence
<220> FEATURE:
<223> OTHER INFORMATION: Description of Artificial Sequence: Probe
<221> NAME/KEY: modified_base
<222> LOCATION: (1)..(9)
<223> OTHER INFORMATION: n = a, c, g or t
<221> NAME/KEY: modified_base
<222> LOCATION: (55)..(63)
<223> OTHER INFORMATION: n = a, c, g or t

<400> SEQUENCE: 18
nnnnnnnnnc cgccgccgcc gccgccgccg ccgccgccgc cgccgccgcc gccgnnnnnn   60 nnn                                                           63

<210> SEQ ID NO 19
<211> LENGTH: 48
<212> TYPE: DNA
<213> ORGANISM: Artificial Sequence
<220> FEATURE:
<223> OTHER INFORMATION: Description of Artificial Sequence: Probe
<221> NAME/KEY: modified_base
<222> LOCATION: (1)..(9)
<223> OTHER INFORMATION: n = a, c, g or t
<221> NAME/KEY: modified_base
<222> LOCATION: (40)..(48)
<223> OTHER INFORMATION: n = a, c, g or t

<400> SEQUENCE: 19
nnnnnnnnnc ggcggcggcg gcggcggcgg cggcggcggn nnnnnnn             48

<210> SEQ ID NO 20
<211> LENGTH: 81
<212> TYPE: DNA
<213> ORGANISM: Artificial Sequence
<220> FEATURE:
<223> OTHER INFORMATION: Description of Artificial Sequence: Probe
<221> NAME/KEY: modified_base
<222> LOCATION: (73)..(81)
<223> OTHER INFORMATION: n = a, c, g or t
<221> NAME/KEY: modified_base
<222> LOCATION: (1)..(9)
<223> OTHER INFORMATION: n = a, c, g or t

<400> SEQUENCE: 20
nnnnnnnnnc ggcggcggcg gcggcggcgg ccggcggcgg cggcggcggg gcggcggcg   60 cggcggcggc gggnnnnnnn n                                       81

<210> SEQ ID NO 21
<211> LENGTH: 60

```
<212> TYPE: DNA
<213> ORGANISM: Artificial Sequence
<220> FEATURE:
<223> OTHER INFORMATION: Description of Artificial Sequence: Probe
<221> NAME/KEY: modified_base
<222> LOCATION: (1)..(9)
<223> OTHER INFORMATION: n = a, c, g or t
<221> NAME/KEY: modified_base
<222> LOCATION: (52)..(60)
<223> OTHER INFORMATION: n = a, c, g or t

<400> SEQUENCE: 21
nnnnnnnnnc ggcggcggcg gcggcggcgg cggcggcggc ggcggcggcg gnnnnnnnnn      60

<210> SEQ ID NO 22
<211> LENGTH: 45
<212> TYPE: DNA
<213> ORGANISM: Artificial Sequence
<220> FEATURE:
<223> OTHER INFORMATION: Description of Artificial Sequence: Probe
<221> NAME/KEY: modified_base
<222> LOCATION: (1)..(9)
<223> OTHER INFORMATION: n = a, c, g or t
<221> NAME/KEY: modified_base
<222> LOCATION: (37)..(45)
<223> OTHER INFORMATION: n = a, c, g or t

<400> SEQUENCE: 22
nnnnnnnnnc cgccgccgcc gccgccgccg ccgccgnnnn nnnnn                      45

<210> SEQ ID NO 23
<211> LENGTH: 63
<212> TYPE: DNA
<213> ORGANISM: Artificial Sequence
<220> FEATURE:
<223> OTHER INFORMATION: Description of Artificial Sequence: Probe
<221> NAME/KEY: modified_base
<222> LOCATION: (1)..(9)
<223> OTHER INFORMATION: n = a, c, g or t
<221> NAME/KEY: modified_base
<222> LOCATION: (55)..(63)
<223> OTHER INFORMATION: n = a, c, g or t

<400> SEQUENCE: 23
nnnnnnnnnc ggcggcggcg gcggcggcgg cggcggcggc ggcggcggcg gcggnnnnnn      60 nnn                                                                   63

<210> SEQ ID NO 24
<211> LENGTH: 78
<212> TYPE: DNA
<213> ORGANISM: Artificial Sequence
<220> FEATURE:
<223> OTHER INFORMATION: Description of Artificial Sequence: Probe
<221> NAME/KEY: modified_base
<222> LOCATION: (1)..(9)
<223> OTHER INFORMATION: n = a, c, g or t
<221> NAME/KEY: modified_base
<222> LOCATION: (71)..(78)
<223> OTHER INFORMATION: n = a, c, g or t

<400> SEQUENCE: 24
nnnnnnnnng ccgccgccgc cgccgccgcc gccgccgccg ccgccgccgc cgccgccgcc      60
gccgccgccn nnnnnnn                                                    78

<210> SEQ ID NO 25
<211> LENGTH: 63
<212> TYPE: DNA
<213> ORGANISM: Artificial Sequence
<220> FEATURE:
```

-continued

```
<223> OTHER INFORMATION: Description of Artificial Sequence: Probe
<221> NAME/KEY: modified_base
<222> LOCATION: (1)..(9)
<223> OTHER INFORMATION: n = a, c, g or t
<221> NAME/KEY: modified_base
<222> LOCATION: (55)..(63)
<223> OTHER INFORMATION: n = a, c, g or t

<400> SEQUENCE: 25
nnnnnnnnng gcggcggcgg cggcggcggc ggcggcggcg gcggcggcgg cggcnnnnnn      60 nnn                                                                   63
```

METHODS FOR DETECTION OF A TRIPLET REPEAT BLOCK AND A FUNCTIONAL MISMATCH BINDING PROTEIN IN A BIOLOGICAL FLUID SAMPLE

This application is a divisional application of application Ser. No. 08/608,016 filed Mar. 4, 1996, now U.S. Pat. No. 6,120,992, which is a continuation-in-part of application Ser. No. 08/431,081 filed Apr. 28, 1995, now U.S. Pat. No. 6,114,115, which is a continuation-in-part of application Ser. No. 08/147,785 filed Nov. 4, 1993, now U.S. Pat. No. 6,027,877, each of which is incorporated by reference herein in its entirety.

BACKGROUND OF THE INVENTION

1. Field of the Invention

The invention in the fields of molecular biology and medicine relates to a method for detecting or screening for mutations or heterozygosity involving as little as one base change or a single base addition to, or deletion from, the wild-type DNA sequence, as well as methods for removing mismatch-containing DNA from batches of amplified DNA.

2. Description of the Background Art

Progress in human molecular and medical genetics depends on the efficient and accurate detection of mutations and sequence polymorphisms, the vast majority of which results from single base substitutions and small additions or deletions. Assays capable of detecting the presence of a particular mutation or mutant nucleic acid sequence in a sample are therefore of substantial importance in the prediction and diagnosis of disease, forensic medicine, epidemiology and public health. Such assays can be used, for example, to detect the presence of a mutant gene in an individual, allowing determination of the probability that the individual will suffer from a genetic disease. The ability to detect a mutation has taken on increasing importance in early detection of cancer or discovery of susceptibility to cancer with the discovery that discrete mutations in cellular oncogenes can result in activation of that oncogene leading to the transformation of that cell into a cancer cell.

The desire to increase the utility and applicability of such assays is often frustrated by assay sensitivity as well as complexity and cost. Hence, it would be highly desirable to develop more sensitive as well as simple and relatively inexpensive assays for detection of alterations in DNA.

Nucleic acid detection assays can be based on any of a number of characteristics of a nucleic acid molecule, such as its size, sequence, susceptibility to digestion by restriction endonucleases, etc. The sensitivity of such assays may be increased by altering the manner in which detection is reported or signaled to the observer. Thus, for example, assay sensitivity can be increased through the use of detectably labeled reagents such as enzymes (Kourilsky et al., U.S. Pat. No. 4,581,333), radioisotopes (Falkow et al., U.S. Pat. No. 4,358,535; Berninger, U.S. Pat. No. 4,446,237), fluorescent labels (Albarella et al., EP 144914), chemical labels (Sheldon III et al., U.S. Pat. No. 4,582,789; Albarella et al., U.S. Pat. No. 4,563,417), modified bases (Miyoshi et al., EP 119448), and the like.

Most methods devised to attempt to detect genetic alterations consisting of one or a few bases involve hybridization between a standard nucleic acid (DNA or RNA) and a test DNA such that the mutation is revealed as a mispaired or unpaired base in a heteroduplex molecule. Detection of these mispaired or unpaired bases has been accomplished by a variety of methods (Myers, R. M. et al., *Cold Spring Harbor Symp. Quant. Biol.* 51:275–284 (1986); Gibbs, R. et al., *Science* 236:303–305 (1987); Lu, A. S. et al., 1992, *Genomics* 14:249–255 (1992); Cotton, R. G. et al., *Proc. Natl. Acad. Sci. USA* 85:4397–4401 (1988); Cotton, R. G., *Nucl. Acids Res* 17:4223–4233 (1989)). Major problems of various of these methods include a requirement for using RNA or an ability to detect only a limited number of mismatches (though the Cotton et al. method is said to detect all possible single base pair mismatches). These methods are also generally laborious, require that the exact location of the mutation be known and are difficult to interpret when the sample DNA is heterozygous for the mutation in question. Therefore, they are not practical for use in screening for polymorphisms. Publications from Caskey's laboratory (Caskey, C. T. et al., European Patent Publication 333,465 (Sep. 20, 1989); Grompe, M. et al., *Proc. Natl. Acad. Sci. USA* 86:5888–5892 (1989)) disclose a method for localizing a mutation using PCR-amplified cDNA.

Wagner et al. (PCT publication WO93/02216, disclosing an invention made by the present inventor) shows that *E. coli* MutS, in solution, detects G//T, G//G and A//C mismatches as well as a frameshift mutation of +1 base. There is no disclosure of using immobilized MutS in this method. (The symbol "//" is used herein with nucleotide base designations to indicate mispaired bases. Proper Watson-Crick base pairs are designated with a ":" for example G:C.)

Lishanskaya et al (*Human Genet* 51,(4 Suppl):A385, abstract #1517 (1992)) is an abstract disclosing the detection of heterozygotes for the amplified CFTR (cystic fibrosis) gene. The method was not shown to be useful for detecting single base mismatches, or mispairings of 1, 2 or 4 bases. Rather, this reference disclosed detection of only one specific mutation of one type caused by a three base pair deletion. The detection was achieved by a gel mobility band-shift assay of MutS-heteroduplex complexes. This reference did not suggest immobilizing a MBP. Lishanski, A. et al., *Proc. Natl. Acad. Sci. USA* 91:2674–2678 (1994 March) described detection of frame shift mutations and A//C, G//T, G//A and T//C mismatches (though primarily G//T) using MutS. Significantly, the method worked poorly with duplexes containing single base pair mismatches. At the time this paper was published (after the filing date of the priority application of the present application), Lishanski et al. were still trying to develop improved detection methods (page 2677 column 2, end of "Conclusions" section, referring to "preliminary experiments") such as the very methods that the present inventor had already invented and disclosed in U.S. Ser. No. 08/147,785). Lishanski et al. (supra) thereby documents (1) the recognition in the art of the need or desire for the present invention and (2) the fact that the present methods were not yet available to the public (as of the date this paper was submitted, Dec. 17, 1993).

A number of publications describe methods for studying certain DNA binding proteins, in particular sequence-specific transcription factors, by electrophoretic separation of generally under denaturing conditions, blotting ("Southwestern blots") or spotting of the separated proteins onto nitrocellulose filters, and probing of the filters with labeled DNA or oligonucleotides. See, for example, Bowen, B. et al., *Nucl. Acids Res.* 8:1–20 (1979); Miskimins, W. K. et al, *Proc. Natl. Acad. Sci. USA* 82:6741–6744 (1985); Keller, A. D. et al., *Nucl. Acids Res.* 19:4675–80 (1991); Norby, P. L. et al., *Nucl. Acids Res.* 20:6317–6321 (1992)). Such initially denatured proteins must be renatured to perform their DNA binding functions; many of these proteins cannot be successfully renatured.

Similar approaches have been used to screen expression libraries by preparing protein replica filters and probing them with labeled DNA or oligonucleotides (Singh et al., *Cell* 52:415–423 (1988); Singh et al., *BioTechniques* 7:253–261 (1989); Vinson et al., *Genes & Devel.* 2:801–806 (1988)). Oliphant, A. R. et al. (*Molec. Cell. Biol.* 9:2944–2949 (1989)) reported use of a sequence-specific DNA binding protein (yeast GCN4 transcriptional activator) coupled to Sepharose to select DNA molecules containing binding sites for this protein from random sequence oligonucleotides. Interactions of DNA with immobilized *E. coli* single stranded DNA-binding protein (SSB) has been reported (Perrino, F. W. et al., *J. Biol. Chem.* 263:11833–11839 (1988)) and is reviewed in Meyer, R. R. et al. (*Microbiol. Rev.* 54:342–380 (1990)).

MISMATCH REPAIR SYSTEMS AND MISMATCH BINDING PROTEINS

DNA mismatch repair systems employ a family of proteins including proteins which recognize and bind to mismatch-containing DNA, which are designated mismatch binding proteins (MBPs). For reviews, see Radman, M. et al., *Annu. Rev. Genet.* 20:523–538 (1986); Radman, M. et al., *Sci. Amer.*, August 1988, pp. 40–46; Modrich, P., *J. Biol. Chem.* 264:6597–6600 (1989)). In 1983, Modrich's laboratory (Lu, A-L. et al., *Proc. Natl. Acad. Sci. USA* 80:4639–4643 (1983)) reported in vitro repair of DNA mismatches using *E. coli* extracts and DNA substrates designed to form a restriction enzyme site after mismatch repair. These first experiments examined only G//T mismatches.

The MutS protein was identified as such a component of the *E. coli* mismatch repair system (Lahue, R. S. et al., *Science* 245:160–164 (1989); Jiricny, J. et al., *Nucl. Acids Res.* 16:7843–7853 (1988); Su, S. S. et al., *J. Biol. Chem.* 263:6829–6835 (1988); Lahue, R. S. et al., *Mutat. Res.* 198:37–43 (1988); Dohet, C. et al., *Mol. Gen. Genet.* 206:181–184 (1987); and Jones, M. et al., *Genetics* 115:605–610 (1987)). Analogous proteins are known in other bacterial species including MutS in *Salmonella typhimurium* (Lu, A-L. et al., *Genetics* 118:593–600 (1988); Haber L. T. et al., *J. Bacteriol.* 170:197–202 (1988); Pang, P. P. et al., *J. Bacteriol.* 163:1007–1015 (1985)) and hexA in *Streptococcus pneumoniae* (Priebe S. D. et al., *J. Bacteriol.* 170:190–196 (1988); Haber et al., supra).

Modrich's laboratory, using the same system described by Lu et al., 1983 (supra) for demonstrating in vitro repair of G//T mismatches, subsequently examined all eight mismatches (Su, S-S. et al., *J. Biol. Chem.* 263:6829–6835 (1988)) and found that all except C//C were repaired. Although C//C mismatches were not sufficiently well recognized to be repaired, Su et al. concluded that the MutS protein recognizes all eight mismatches. The experiments from which this conclusion was drawn were not in vitro repair experiments, but, rather, were nuclease protection or "footprinting" experiments. In the nuclease protection assay, mismatch-containing DNA was incubated with MutS (10 min) and then briefly (20 sec) treated with DNase I. In these experiments, protection of mismatch containing regions was observed with all mismatches, including C//C (which had an apparent affinity less than $\frac{1}{12}$ that of G//T. These results suggested to the present inventor that there are at least two levels of MutS interaction with mismatch-containing DNA:

(1) an interaction sufficient to protect the region of DNA containing the mismatch from degradation by the nuclease enzyme but not sufficient to allow further steps in the DNA repair process, and (2) an interaction sufficient to provide nuclease protection for the mismatch region and to allow further steps in the repair process.

These two types of interaction appear to be mismatch-specific. The more stable interaction would be that which allows further steps in the repair process to occur.

Results of Jiricny et al., *Nucl. Acid Res.* 16:7343–7353 (1987)), which preceded the Su et al. (supra) publication, suggested yet a third level of mismatch-specific interaction between MutS and mismatch-containing DNA in vitro. This paper reported results of (a) nitrocellulose filter binding and (b) gel band-shifting experiments. In these studies, MutS was mixed with small, radiolabeled oligonucleotides (16mers) containing various mismatches, and the resulting complexes detected either by (a) their retention on nitrocellulose or (b) an alteration of DNA mobility in polyacrylamide gel electrophoresis. All mismatches were not tested. However, the results of these experiments were radically different from those observed in both in vitro repair and nuclease protection experiments discussed above. In particular, a G//T mismatch was bound whereas the complementary A//C mismatch at the same position was not. (A//C mismatches were well-repaired in the in vitro repair experiments.) Clearly, there exists a fundamental difference between the Jiricny et al. binding experiments and the Lu et al. (supra) or Su et al. (supra) footprinting or in vitro repair experiments: Repair or nuclease protection requires a more stable interaction (binding) between the MutS and DNA and further requires the retention of the DNA duplex substrate by the MutS. Again, the interaction (binding) appears to be mismatch specific. Jiricny et al. (supra) also reported results suggesting that this stable binding can be competed by the less stable interaction characteristic of footprinting. When unlabeled G//T-containing oligonucleotides were mixed in large excess (40-fold) with labeled G//T-containing oligonucleotides, the amount of binding to G//T was decreased.

Purified MutS protein binds DNA containing mispaired bases, but does not bind DNA without mismatches or single-stranded DNA. The MutS-DNA interaction does not result in any degradation or modification of the DNA. None of the above references disclose the possibility of using a MBP or immobilized MBP as part of a mutation detection assay or for purposes of removing mismatched DNA from amplified DNA samples. Modrich et al., U.S. Pat. No. 5,459,039 (Oct. 17, 1995), having a priority filing date of May 12, 1989, discloses methods for detecting base sequence differences comprising annealing complementary strands and detecting the binding of a MBP to a base pair mismatch using a suitable analytical method. This document does not disclose any information concerning MBP-DNA interactions not contained in the documents cited above, particularly Su et al., supra, and Jiricny et al., supra. Importantly, none of the these three references discloses or suggests the immobilization of the MBP prior to contacting with putative heteroduplex DNA nor do they point to any expected advantages of such immobilization.

The literature concerning DNA repair suggests that all mismatches are not repaired with equal efficiency in vivo (Dohet, C. et al., *Proc. Natl. Acad. Sci. USA* 82:503–505 (1985). If poorly-repaired mismatches were created as frequently as well-repaired mismatches, one would not observe the 100–1000-fold increase in mutation rate in mutant cells lacking MutS function. Therefore, the poorly-recognized mismatches, in particular C//C (Dohet et al., supra, Jiricny et al., supra), must not be created as frequently as other well-recognized mismatches, since 99.9% of created mutations are repaired. Hence, MutS must bind to mismatched DNA (and induce the repair process) for virtually any error made by a polymerase enzyme.

DETECTION OF INFECTIOUS AGENTS

Classical methods of detecting infectious agents involved either: (1) culturing of the microorganism, which is slow and virtually impossible with some organisms, (2) microbiological characterization, (3) serological typing or (4) indirect detection by detection of specific antibodies in the infected host. The obvious limitations of these classical methods, in terms of feasibility and accuracy, coupled with their prohibitive requirements for labor, time and money, have made them, for all practical purposes, obsolete. More recently, detection methods have been developed using specific PCR amplification in which PCR primers are designed to amplify specifically DNA of a particular strain of an infectious agent. These methods greatly improved the speed and accuracy of detection and characterization and made it possible to: (1) detect those organisms difficult or impossible to culture, (2) detect organisms directly from biological samples (e.g., blood, urine, feces, biopsy samples, etc.), (3) detect genomes of pathogens integrated into the host genome, and (4) estimate the concentration of pathogenic organisms in complex samples. In these assays, the presence of a PCR product is indicative of the presence of a specific infectious organism. However, the disadvantages of specific PCR amplification detection include: (a) detection, in general, involves gel electrophoresis, and (b) specific primer pairs must be selected for each variant and must amplify that variant exclusively. The present invention provides solutions to these shortcomings.

MBPs AND CANCER

The recent discoveries that mutations in genes coding for MBPs can predispose to many types of cancer, particularly colon cancer, have stimulated increasing interest in determining whether such proteins are present in tumor cells. These MBPs, generally homologs of the bacterial protein MutS, are commonly referred to as "MutS homologs" (designated MSH) and are key elements of the mismatch repair system. Individuals heterozygous for a mutation in the human homologue hMSH2 are predisposed to a form of colon cancer (hereditary non-polyposis colon cancer or HNPCC) (Leach, S. S. et al., *Cell* 75:1212–1225 (1993); Fishel, R. et al., *Cell* 75:1027–1029 (1993)). Although the somatic cells of these individuals have normal levels of mismatch repair, HNPCC tumors have been found to be deficient in mismatch repair and have lost function of the homologous copy of the hMSH2 gene, generally by a second mutation (Parsons, R. et al., *Cell* 75:1227–1236 (1993)). HNPCC tumors were originally characterized by the presence of microsatellite instability, also known as the replication error or "RER" phenotype. However, all RER tumors are not necessarily hMSH2 deficient. Mutations in other mismatch repair genes, in particular homologs of the bacterial mutL gene (MLH and PMS) can also produce an RER phenotype (Papadopoulos, N. et al., *Science* 263:1625–1629 (1994); Bronner, E. C. et al., *Nature* 368:258–261 (1994)). Defects in other cellular functions may also give an RER phenotype (Bhattacharya, N. P. et al., *Proc. Natl. Acad. Sci. USA* 91:6319–6323 (1994)).

Current methods for determining if a tumor cell line is deficient in mismatch binding activity include in vitro mismatch repair assays and sequencing. Mismatch repair assays are somewhat laborious and cannot distinguish MSH deficiencies from MLH deficiencies unless complementation assays are performed. Sequencing is extremely laborious because the homologous chromosome sequences must be separately cloned and sequenced to distinguish heterozygotes from homozygotes. In addition, neutral polymorphisms, i.e., sequence differences between the homologs which do not affect protein function, can make interpretation of sequencing results difficult.

In response to these deficiencies in the art, the present inventor provides a simple, rapid and inexpensive assay for activity of a MBP in a test sample which does not require the use of gels, sequencing or radioactivity. The assay is based upon the immobilized mismatch binding protein mutation detection assay.

TRIPLET REPEATS

A growing number of diseases is known to be associated with the expansion of "triplet" or trinucleotide repeat sequences (Trottier, Y. et al., *Current Biology* 3:783–786 (1993); Bates, G. et al., *Bioessays* 16:277–284 (1994); Kawaguchi, Y. et al., *Nature Genetics* 8:221–227 (1994)). In each of these diseases, the size of the repeat block directly correlates with, and thereby "anticipates" the severity and age of the onset of the disease. Some diseases are correlated with small increases in the size of the repeat block, for example, Huntington's disease, spino-cerebellar ataxia type I, spinal and bulbar muscular atrophy, Machado-Joseph disease and dentatorubralpallidoluysian atrophy. Other diseases involve up to 100-fold expansions of the normal block, such as fragile X type A, fragile X type E and myotonic dystrophy. In general, it appears that, if the repeated motif is short, for example, <10 nucleotides, and the repeat block is shorter than about 0.3 kb, replication slippage is the principal mechanism of instability (Kunkel, T. A., *Nature* 36S:207–208 (1994)). If the repeat block is greater than 0.3 kb (the minimum size for efficient homologous DNA interactions), recombination and/or DNA methylation can affect the size and the sequence of such repeats.

"Satellite DNA" is a term used to describe highly repetitive sequences that are clustered together, and may consist of tandem repeats of a simple sequence. These range in size, with shorter sequences being termed "minisatellite" and yet shorter sequences described as "microsatellite." The most prevalent form of human microsatellite DNA comprises small expansions and contractions of $CA_n$ repeat blocks. These occur very frequently as a result of replication slippage in mismatch repair-deficient HNPCC tumor cells (Bronner, E. C. et al., *Nature* 368, 258–261 (1994)).

DNA methylation is found in the CGG repeats of fragile X syndrome (Trottier, Y. et al., *Current Biology* 3:783–786 (1993); Bates, G. et al., *Bioessays* 16:277–284 (1994); Radman, M. et al. In: *GENOME ANALYSIS,* vol 7 (Genome Rearrangement and Stability) eds. K. E. Davies et al., pp. 139–152 (1993)). Changes in "minisatellite" size (polymorphic repeat blocks several kb in length) and in DNA sequence occur by gene conversion (Jefferys, A. J. et al., *Nature Genetics* 6:136–145 (1994)). However, the mechanism of the rapid and large expansions of CGG/CCG and CAG/CTG repeats is unknown.

The present invention is designed in part to detect the presence of such expanded triplet repeat blocks for diagnosing diseases associated with such repeats.

SUMMARY OF THE INVENTION

The present inventor has conceived of the use of compositions and methods which employ immobilized mismatch binding proteins (MBPs), for example, the MutS protein of *E. coli,* for the following: (1) screening for or detection of genetic mutations, heterozygosity or genomic polymorphisms, (2) partial or complete purification of amplified DNA samples by removing contaminating sequences and sequences containing errors introduced during the amplification processes, as well as detecting and enriching minority sequences; (3) identifying the presence of a specific allele in multi-allelic systems; (4) screening for the presence of either a specific known sequence in a selected region of an allele or an unknown sequence in the same selected region of a previously unknown allele of a multi-allelic system.

The nucleic acid, preferably DNA, being analyzed can be obtained from any source, including blood cells, tumor tissues, cells in culture or any tissue, and can be obtained from any species including humans. The DNA may be labeled by any of a variety of well-known methods, using colorimetric, chemiluminescent or radioactive markers. In fact, it is not necessary to label test DNA at all.

For detection of mutations or polymorphisms, the assay can be performed with a labeled competing oligonucleotide. For purification of amplified DNA, no label is required. For allele identification, the label must be in a synthesized single-stranded oligonucleotide probe.

The methods of the present invention depend on the creation of mismatches in the test DNA which are revealed by denaturing the test DNA and allowing it to reanneal. When testing for heterozygosity or for polymorphism within a test DNA sample, the test DNA can simply be self-annealed, resulting in formation of mismatches when the single strands reanneal with a strand descended from the other parental chromosome. If no heterozygosity exists, no mismatches will be formed. In this case, the label can be in the primers used for amplification or may be added to the termini of the test DNA if amplification is not required.

A similar procedure and labeling scheme is used to remove sequences containing errors introduced during amplification of DNA or minority sequence species. In these cases, the material which does not bind to the MBP is recovered, and contains only those duplex sequences without mismatches. These sequences will therefore be greatly enriched for the majority sequence in the amplified population. When the starting material contains only one sequence, the unbound material will contain those sequences which are identical to the starting material, while those sequences containing errors introduced during amplification will, provided they are relatively rare, have formed mismatches which are retained by the immobilized MBP. This method therefore allows purification of the faithfully replicated DNA or removal of a majority of error-containing sequences.

To detect homozygous mutations, it is necessary to anneal the test DNA in the presence of known wild-type sequences. Such sequences can be synthesized artificially or created during amplification by adding known wild-type sequences to the starting material before amplification. When annealing is performed in the presence of known wild-type sequences, the assay will detect both homozygous and heterozygous mutations.

For allele identification, it is necessary to add a labeled single-stranded probe DNA to the test DNA after amplification. The probe sequence must be identical to the allele of interest such that no mismatches are formed when it anneals to DNA of that allele. The sequence of the probe is selected so that it forms mismatches when annealed to the DNA of any other allele. When test DNA is annealed to such a probe (with the test DNA in excess such that the probe sequences all anneal to form a duplex) and exposed to excess immobilized MBP, the presence of unbound label indicates that the allele in question is present in the test DNA sample.

In its most fundamental form, the present invention is directed to a method for detecting in a test polynucleotide sample, preferably DNA, the presence of a heteroduplex having a single base pair mismatch or a deletion or addition of up to about 4 nucleotides, which method comprises detecting the binding of polynucleotides of said sample to a mismatch-binding protein immobilized on a solid support. The mismatch binding protein is preferably E. coli MutS protein, or a homologue thereof from a different prokaryotic or eukaryotic species.

The present invention is also directed to a method for detecting a mutation in heterozygous form in a test polynucleotide sample, preferably DNA, wherein the heterozygosity or mutation is the result of (i) a nucleotide substitution or (ii) a deletion or addition of up to about 4 nucleotides, which method comprises:

(a) obtaining test polynucleotide comprising sequences corresponding to all four DNA strands from a pair of chromosomes, or from a segment thereof, of a diploid organism;

(b) detectably labeling the test polynucleotide any time prior to step (c) below, and, optionally amplifying the test polynucleotide;

(c) denaturing any double stranded polynucleotide in the sample into single strands and allowing the single strands to reanneal into duplexes;

(d) incubating the detectably labeled polynucleotide duplexes with an immobilized mismatch-binding protein under conditions in which heteroduplexes containing a mismatch or one to about four unpaired bases bind to the immobilized protein; and (e) detecting the binding of any of the heteroduplexes of step (d) to the protein, wherein the presence of detectably labeled polynucleotide bound to the protein is indicative of the presence of the mutation in the test polynucleotide.

In the above method, the mismatch-binding protein is preferably E. coli MutS protein, or a homologue thereof from a different prokaryotic or eukaryotic species.

This invention further provides a method for detecting or screening for a homozygous or heterozygous mutation in a test polynucleotide, preferably DNA, in a sample, wherein the mutation is the result of (i) a nucleotide substitution or (ii) a deletion or addition of up to about 4 nucleotides, which method comprises:

(a) detectably labeling anytime prior to step (c) below, (i) the test polynucleotide, or (ii) an added polynucleotide or oligonucleotide, preferably DNA, as recited in step (b), below, or (iii) both (i) and (ii);

(b) denaturing double stranded polynucleotide in the sample into single strands in the presence of an added polynucleotide or oligonucleotide molecule having the wild-type sequence for the mutation, and allowing the strands to reanneal into duplexes;

(c) incubating the detectably labeled polynucleotide duplexes with an immobilized mismatch-binding protein under conditions in which heteroduplexes containing a mismatch or one to four unpaired bases bind to the immobilized protein; and (d) detecting the binding of any mismatch-containing double stranded polynucleotide from the sample to the protein, wherein the presence of detectably labeled polynucleotide or oligonucleotide bound to the immobilized protein is indicative of the presence of the mutation in the test polynucleotide.

In the above method, the sample polynucleotide may be amplified prior to step (b). The added polynucleotide or oligonucleotide of step (b) may be added prior to the amplifying step.

The present invention is also directed to a competitive assay method for detecting or screening for heterozygosity or the presence of a mutation in heterozygous form in a test polynucleotide, preferably DNA, in a sample, wherein the heterozygosity or the mutation is the result of (i) a nucleotide substitution or (ii) a deletion or addition of up to about four nucleotides, which method comprises:

(a) obtaining test polynucleotide comprising sequences corresponding to all four DNA strands from a pair of chromosomes, or a segment thereof of a diploid organism;

(b) denaturing double stranded polynucleotide in the sample into single strands and allowing the single strands to reanneal into duplexes;

(c) incubating the denatured and reannealed duplexes of step (b) with a E. coli MutS protein, or a homologue thereof from a different prokaryotic or eukaryotic species, immobilized on a solid support, either (i) in the presence of a detectably labeled mismatch-containing oligonucleotide capable of binding to the protein; or (ii) wherein the immobilized protein was preincubated with and allowed to bind a detectably labeled mismatch-containing oligonucleotide, under conditions in which heteroduplexes containing a mismatch or one to four unpaired bases bind to the immobilized protein; and (d) detecting the amount of detectably labeled mismatch-containing oligonucleotide bound to the protein, wherein the presence of the heterozygosity or the mutation in the test polynucleotide results in a decrease in the binding of the detectably labeled oligonucleotide to the protein.

In the method above, the sample DNA may be amplified prior to step (a).

Also provided is a competitive assay method for detecting or screening for a homozygous or heterozygous mutation in test polynucleotide, preferably DNA, in a sample, wherein the mutation is either the result of a nucleotide substitution or a deletion or addition of up to about four nucleotides, which method comprises:

(a) denaturing any double stranded polynucleotide in the sample into single strands in the presence of an added polynucleotide or oligonucleotide molecule having the wild-type sequence for the mutation, and allowing the single strands to reanneal into duplexes;

(b) incubating the denatured and reannealed duplexes formed in step (a) with a E. coli MutS protein, or a homologue thereof from a different prokaryotic or eukaryotic species, immobilized on a solid support, either (i) in the presence of a detectably labeled mismatch-containing oligonucleotide capable of binding to the protein; or (ii) wherein the immobilized protein had first been preincubated with, and allowed to bind to, a detectably labeled mismatch-containing oligonucleotide prior to the incubating, under conditions in which heteroduplexes containing a mismatch or one to four unpaired bases bind to the immobilized protein; and (c) detecting the detectably labeled mismatch-containing oligonucleotide bound to the protein, wherein the presence of the homozygous or heterozygous mutation in the test polynucleotide of the sample decreases the amount of detectably labeled oligonucleotide bound to the protein.

In the method above, the sample DNA may be amplified prior to step (a). The added polynucleotide or oligonucleotide of step (a) (preferably a deoxyribopolynucleotide or a deoxyribo-oligonucleotide), may be added prior to the amplifying step.

The present invention also includes methods for detecting and/or enriching nucleic acid molecules, preferably DNA, having minority sequences relative to nucleic acid molecules having a majority sequence in a nucleic acid sample, which minority sequences differ from the majority sequence by one or more single base pair substitutions or additions or deletions of one to four base pairs. The enriching method comprises:

(a) causing the minority sequences to anneal to nucleic acid strands having the majority sequence, thereby forming a mixture of
 i. homoduplexes, and
 ii. heteroduplexes comprising hybrids of minority sequence and majority sequence;

(b) incubating the mixture with immobilized mismatch binding protein, preferably immobilized on nitrocellulose or magnetic beads, under conditions wherein heteroduplexes containing a mismatch or one to four unpaired bases bind to and are retained by the immobilized protein; and (c) removing unbound nucleic acid fragments from the immobilized protein, thereby enriching the minority sequences.

In the above method, the nucleic acid sample may be an RNA sample, and the majority sequences of step (a) are added DNA molecules, such that the heteroduplexes formed in step (a) and retained on the immobilized protein in step (b) are RNA/DNA hybrids.

In another embodiment, the above method further comprises detecting the minority sequence by first amplifying the heteroduplexes bound and retained on the protein in step (b).

The above method for detecting minority sequences comprises:

(a) obtaining and amplifying test polynucleotides in a sample;

(b) detectably labeling the test polynucleotide any time prior to step (d) below;

(c) denaturing double stranded polynucleotide in the sample into single strands and allowing the single strands to reanneal into duplexes;

(d) incubating the detectably labeled duplexes with an immobilized mismatch-binding protein, under conditions in which heteroduplexes containing a mismatch or one to four unpaired bases bind to and are retained by the immobilized protein; and (e) detecting the binding of any of the heteroduplexes of step (d) to the protein, wherein the presence of detectably labeled polynucleotide bound to U the immobilized protein is indicative of the presence of the minority sequence.

In another embodiment, the invention is directed to a method for the removal from an amplified DNA sample of a majority of (i) sequences containing sequence errors introduced during the process of amplification and (ii) minority sequences, wherein the sequence errors and the minority sequences are the result of a nucleotide substitution or a deletion or addition of up to about 4 nucleotides, which method comprises:

(a) subjecting the amplified DNA sample to conditions of denaturation followed by reannealing, such that the error-containing or the minority sequences form heteroduplexes containing a mismatch or one to four unpaired bases, thereby generating a mixture of perfectly matched duplexes and the heteroduplexes;

(b) incubating the mixture of step (a) with an immobilized mismatch binding protein under conditions in which the heteroduplexes formed in step (a) bind to the immobilized protein; and (c) removing the immobilized protein to which the heteroduplexes are bound from the amplified DNA sample, thereby removing the majority of the sequences containing sequence errors and minority sequences from the amplified DNA sample.

Also provided is a method for screening a test polynucleotide sample, preferably DNA, for the presence of either a specific known sequence in a selected region of an allele or an unknown sequence in the same selected region of a previously unknown allele of a multi-allelic system, wherein the known sequence is characterized as differing from other known sequences in the same selected region of other known alleles of said multi-allelic system by a nucleotide substitution or a deletion or addition of up to 4 nucleotides, which method comprises:

(a) mixing a detectably labeled oligonucleotide probe, which probe
  (i) is perfectly complementary to the known sequence of the allele, and
  (ii) forms detectable heteroduplexes containing a single base mismatch or one to four unpaired bases when annealed with any other known sequences in the selected region of other known alleles of the multi-allelic system, with an excess of the test polynucleotide under conditions of denaturation followed by annealing such that, every copy of the probe is in a homoduplex or heteroduplex;

(b) incubating the mixture formed in step (a) with an excess of immobilized mismatch binding protein under conditions in which the heteroduplexes formed in step (a) bind to the immobilized protein; and (c) removing the immobilized protein to which said heteroduplexes are bound from said test DNA; and (d) detecting the presence of said detectable label in the remaining mixture of step (c) from which the bound heteroduplexes have been removed, wherein, the presence of the labeled probe in the remaining mixture of step (d) indicates the presence in the test DNA sample of either (i) the said specific sequence, or (ii) the unknown sequence, which unknown sequence is characterized in that it differs from the known sequence such that when the unknown sequence is annealed to the probe, the resulting heteroduplex is not bound by the immobilized protein.

In the method above, the test DNA may be amplified DNA

Also provided herein is a method for screening a test DNA sample for the presence of a mutation or polymorphism in a specific region compared to DNA of known sequence, wherein the mutation or polymorphism:

(i) results from a nucleotide substitution or a deletion or addition of up to four nucleotides, and (ii) results in formation of a heteroduplex when a mutant or polymorphic DNA strand is paired with a DNA strand of known sequence, which heteroduplex is bound by a mismatch-binding protein, the method comprising:

(a) detectably labeling the test DNA any time prior to step (c) below;

(b) denaturing double stranded DNA in the sample into single strands and allowing the single strands to reanneal into duplexes;

(c) incubating the detectably labeled DNA duplexes with an immobilized mismatch-binding protein under conditions in which heteroduplexes containing a mismatch or one to four unpaired bases bind to the immobilized mismatch-binding protein; and (d) detecting the binding of any of the heteroduplexes of step (c) to the immobilized protein, wherein the presence of detectably labeled DNA bound to the protein is indicative of the presence of the mutation or polymorphism in the known region of the test DNA.

The test DNA above may be amplified prior to step (b).

Also provided is a method for screening a test polynucleotide sample, preferably DNA, for the presence of a specific known sequence in a selected region of an allele of a multi-allelic system, wherein the known sequence is characterized as differing from other known sequences in the same selected region of other known alleles of the multi-allelic system by one or more nucleotide substitutions, or deletions or additions of up to 4 nucleotides, which method comprises:

(a) mixing a detectably labeled oligonucleotide probe, which probe (i) is perfectly complementary to the known sequence of the allele, and (ii) forms detectable heteroduplexes containing a single base mismatch or one to four unpaired bases when annealed with any other known sequences in the selected region of other known alleles of the multi-allelic system, with the test polynucleotide under conditions of denaturation followed by annealing such that the probe anneals with the test polynucleotide to form a homoduplex or heteroduplex;

(b) incubating the mixture formed in step (a) with a immobilized mismatch binding protein under conditions in which the heteroduplexes formed in step (a) bind to the immobilized mismatch binding protein under conditions in which the heteroduplexes formed in step (a) bind to the immobilized protein; and (c) detecting the binding of any of the heteroduplexes of step (b) to the protein, wherein the absence of detectably labeled polynucleotide bound to the immobilized protein is indicative of the presence of the specific known sequence in the test polynucleotide sample.

Also provided is a method for screening a test polynucleotide sample, preferably DNA, for a homozygous or heterozygous mutation in a specific region of known sequence, wherein the specific mutation (i) results from a nucleotide substitution or a deletion or addition of up to about four nucleotides, and (ii) results in formation of a heteroduplex when a mutant DNA strand is paired with a DNA strand having the wild type sequence, which heteroduplex is bound by a mismatch-binding protein, the method comprising:

(a) detectably labeling anytime prior to step (c) below, the test polynucleotide or an added polynucleotide or oligonucleotide as recited in step (b), below, or both the test polynucleotide and the added polynucleotide or oligonucleotide;

(b) denaturing any double stranded polynucleotide in the sample into single strands in the presence of an added polynucleotide or oligonucleotide molecule having the wild-type sequence for the mutation, and allowing the single strands to reanneal into duplexes;

(c) incubating the detectably labeled duplexes with an immobilized mismatch-binding protein under conditions in which heteroduplexes containing a mismatch or one to four unpaired bases bind to the immobilized mismatch-binding protein; and (d) detecting the binding of any of the heteroduplexes of step (c) to the immobilized protein, wherein the presence of detectably labeled polynucleotide bound to the protein is indicative of the presence of the mutation in the specific region in the test DNA.

In the method above, the test DNA may be amplified prior to step (b).

In another embodiment, the invention provides a method for detecting in a test DNA a heterozygous mutation in a specific region having a known sequence, wherein the mutation is the result of (i) a nucleotide substitution or (ii) a deletion or addition of up to about 4 nucleotides, which method comprises:

(a) digesting the test DNA with one or two restriction enzymes to create a restriction fragment containing the site of the mutation, and, for PCR or other DNA synthetic amplification, preferably at least one primer site for initiation of DNA synthesis;

(b) denaturing the restriction fragment into single strands and allowing the strands to reanneal into duplexes;

(c) incubating the duplexes with an immobilized mismatch-binding protein under conditions in which heteroduplexes among the duplexes containing a mismatch or one to four unpaired bases bind to the immobilized protein;

(d) removing any DNA not bound to the immobilized protein;

(e) amplifying the DNA which contains the site of the mutation and which remains bound to the immobilized protein; and (f) detecting the amplified DNA, wherein the presence of the amplified DNA is indicative of the presence of a mismatch in the annealed duplexes, thereby detecting the heterozygous mutation in the test DNA.

Also provided is a method for detecting a homozygous or heterozygous mutation having a known sequence in a specific region of a test DNA, wherein the mutation is the result of (i) a nucleotide substitution or (ii) a deletion or addition of up to about 4 nucleotides, which method comprises:

(a) digesting the test DNA with one or two restriction enzymes to create a restriction fragment containing the site of the mutation, and, for PCR or other DNA synthetic amplification, preferably at least one primer site for initiation of DNA synthesis;

(b) denaturing the restriction fragment into single strands in the presence of an added DNA polynucleotide or oligonucleotide molecule having the wild-type sequence for the mutation, and allowing the strands to anneal into duplexes;

(c) incubating the duplexes with an immobilized mismatch-binding protein under conditions in which heteroduplexes among the duplexes containing a mismatch or one to four unpaired bases bind to the immobilized protein;

(d) removing any DNA not bound to the immobilized protein;

(e) amplifying the DNA which contains the site of the mutation and which remains bound to the immobilized protein; and (f) detecting the amplified DNA, wherein the presence of the amplified DNA is indicative of the presence of a mismatch in the annealed duplexes, thereby detecting the homozygous or heterozygous mutation in the test DNA.

Another method of the present invention is directed to determining the presence or absence of a functional mismatch-binding protein in a biological fluid sample, comprising:

(a) mixing the biological fluid sample with a detectably labeled double-stranded oligonucleotide heteroduplex containing a mismatch or mispairing, or a denatured single stranded oligonucleotide which will anneal to create the heteroduplex, thereby forming a mixture;

(b) contacting the mixture with an immobilized mismatch-binding protein under conditions where the immobilized mismatch-binding protein binds to labeled heteroduplex in the mixture;

(c) detecting the binding of any of the heteroduplexes to the immobilized protein, (d) separately detecting the binding of the labeled oligonucleotide heteroduplex to the immobilized protein in the absence of the sample, wherein a decrease in the binding detected in step (c) compared to step (d) is indicative of the presence of a functional mismatch-binding protein in the sample.

A method for detecting the presence of a triplet repeat block of unit sequence

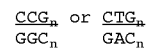

in a test DNA molecule in a sample, which block is longer than a triplet repeat block in a diagnostic oligonucleotide probe, comprises:

(a) incubating the test DNA with a detectably labeled single stranded diagnostic oligonucleotide probe having a unit triplet repeat sequence $CGG_m$ or $CTG_m$, wherein i. n is the number of repeats of the triplet repeat block of the test DNA ii. m is the number of repeats of the triplet repeat block of the probe, and iii. n and m are integers, this probe preferably also including sequences of the DNA region flanking the triplet repeat sequences;

(b) denaturing any double stranded DNA in the mixture of step (a) into single strands and allowing the strands to reanneal into duplexes;

(c) incubating the mixture of step (b) with an immobilized mismatch binding protein under conditions in which heteroduplexes containing a mismatch or one to four unpaired bases bind to the immobilized protein; and (d) detecting the binding of any of the heteroduplexes of step (d) to the immobilized protein, wherein the presence of detectably labeled DNA bound to the protein is indicative of the presence in the test DNA a triplet repeat block with a repeat number n greater than m.

In a related embodiment is provided a method for detecting the presence of a triplet repeat block of unit sequence

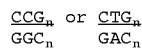

in a test DNA molecule in a sample, which block is shorter than a triplet repeat block in a diagnostic oligonucleotide probe, which method comprises:
(a) incubating the test DNA with a detectably labeled single stranded diagnostic oligonucleotide probe having a unit triplet repeat sequence CGGm or CTGm, wherein
   i. n is the number of repeats of the triplet repeat block of the test DNA,
   ii. m is the number of repeats of the triplet, repeat block of the probe, and
   iii. n and m are integers,
this probe preferably also including sequences of the DNA region flanking the triplet repeat sequences;
(b) denaturing any double stranded DNA in the mixture of step (a) into single strands and allowing the strands to reanneal into duplexes;
(c) incubating the mixture of step (b) with an immobilized mismatch binding protein under conditions in which heteroduplexes containing a mismatch or one to four unpaired bases bind to the immobilized protein; and
(d) detecting the binding of any of the heteroduplexes of step (d) to the immobilized protein,
wherein the presence of detectably labeled DNA bound to the protein is indicative of the presence in the test DNA a triplet repeat block with a repeat number n less than m. The above method may be conducted with the following modifications: (i) prior to step (a), the test DNA is amplified to produce multiple copies of amplified oligonucleotides having the triplet repeat block sequence; and (ii) the amplified nucleotides are incubated in step (b) with the detectably labeled single stranded oligonucleotide probe.

In another embodiment, the invention provides a competitive assay method for detecting the presence of a triplet repeat block of unit sequence

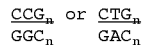

in a test DNA molecule in a sample, which block is longer than a triplet repeat block in a diagnostic oligonucleotide probe, which method comprises:
(a) incubating the test DNA with a single stranded diagnostic oligonucleotide probe having a unit triplet repeat sequence $CGG_m$ or $CTG_m$, wherein
   i. n is the number of repeats of the triplet repeat block of the test DNA
   ii. m is the number of repeats of the triplet repeat block of the probe, and
   iii. n and m are integers;
(b) incubating the duplexes formed in step (a) with E. coli MutS protein, or a homologue thereof from a different prokaryotic or eukaryotic species, immobilized on a solid support, either
   i. in the presence of a detectably labeled mismatch-containing double stranded oligonucleotide capable of binding to the protein; or
   ii. wherein the protein was preincubated with and allowed to bind to a detectably labeled mismatch-containing double stranded oligonucleotide, under conditions in which heteroduplexes containing a mismatch or one to four unpaired bases bind to the immobilized protein; and
(c) detecting the amount of detectably labeled mismatch-containing oligonucleotide bound to the immobilized protein,
wherein a decrease in the binding of the detectably labeled oligonucleotide to the protein is indicative of the presence in the test DNA of a triplet repeat block with a repeat number n greater than m.

Another related competitive assay method detects the presence of a triplet repeat block of unit sequence

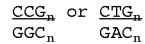

in a test DNA molecule in a sample, which block is shorter than a triplet repeat block in a diagnostic oligonucleotide probe, which method comprises:
(a) incubating the test DNA with a single stranded diagnostic oligonucleotide probe having a unit triplet repeat sequence $CGG_m$ or $CTG_m$, wherein
   i. n is the number of repeats of the triplet repeat block of the test DNA
   ii. m is the number of repeats of the triplet repeat block of the probe, and
   iii. n and m are integers;
(b) incubating the duplexes formed in step (a) with E. coli MutS protein, or a homologue thereof from a different prokaryotic or eukaryotic species, immobilized on a solid support, either
   i. in the presence of a detectably labeled mismatch-containing double stranded oligonucleotide capable of binding to the protein; or
   ii. wherein the protein was preincubated with and allowed to bind to a detectably labeled mismatch-containing double stranded oligonucleotide,
   under conditions in which heteroduplexes containing a mismatch or one to four unpaired bases bind to the immobilized protein; and
(c) detecting the amount of detectably labeled mismatch-containing oligonucleotide bound to the immobilized protein,
wherein a decrease in the binding of the detectably labeled oligonucleotide to the protein is indicative of the presence in the test DNA of a triplet repeat block with a repeat number n less than m.

The present invention provides methods of detecting an allele in a subject which, when passed to progeny, will result in a disease or syndrome associated with triplet repeats, including fragile X syndrome (type A or type E), myotonic dystrophy, Huntington's disease, spino-cerebellar ataxia type I, spinal bulbar muscular atrophy, Machado-Joseph disease and dentatorubralpallidoluysian atrophy.

The present invention also provides a method for enriching nucleic acid molecules, preferably DNA, having minority sequences relative to nucleic acid molecules having a majority sequence in a nucleic acid sample, which minority sequences differ from the majority sequence by one or more single base pair substitutions or additions or deletions of one to four base pairs, which method comprises:
(a) causing the minority sequences to anneal to nucleic acid strands having the majority sequence, thereby forming a mixture of (i) homoduplexes and (ii) heteroduplexes comprising hybrids of minority sequence and majority sequence;
(b) incubating the mixture with immobilized mismatch binding protein (preferably immobilized to magnetic beads or nitrocellulose) under conditions wherein heteroduplexes containing a mismatch or one to four unpaired bases bind to and are retained by the immobilized protein; and (c) removing unbound nucleic acid fragments from the immobilized protein, thereby enriching the minority sequences.

In another embodiment of the above method, the nucleic acid sample is an RNA sample, and the majority sequences of step (a) are added DNA molecules, such that the heteroduplexes formed in step (a) and retained on the immobilized protein in step (b) are RNA/DNA hybrids.

The foregoing methods may further comprise detecting the minority sequences by (d) amplifying the heteroduplexes bound and retained on the protein in step (b); and (e) detecting the amplified sequences.

Also provided is a method for detecting a minority nucleotide sequence among majority sequences present in a polynucleotide sample, wherein the minority sequence differs from the majority sequence by (i) a nucleotide substitution or (ii) a deletion or addition of up to about 4 nucleotides, which method comprises:

(a) obtaining and amplifying test polynucleotides in a sample;

(b) detectably labeling the test polynucleotides any time prior to step (d) below;

(c) denaturing double stranded polynucleotide in the sample into single strands and allowing the single strands to reanneal into duplexes;

(d) incubating the detectably labeled duplexes with an immobilized mismatch-binding protein, under conditions in which heteroduplexes containing a mismatch or one to four unpaired bases bind to and are retained by the immobilized protein; and (e) detecting the binding of any of the heteroduplexes of step (d) to the protein, wherein the presence of detectably labeled polynucleotide bound to and retained by the immobilized protein is indicative of the presence of the minority sequence.

In all the methods described above, the solid support is preferably selected from the group consisting of natural cellulose, modified cellulose, nitrocellulose, polystyrene, polypropylene, polyethylene, dextran, nylon, polyacrylamide, polyvinylidene difluoride, agarose and magnetic beads. A most preferred solid support is a nitrocellulose membrane.

The detectable label in the above methods is preferably a colorimetric compound, a chemiluminescent compound, a bioluminescent compound, a fluorescent compound or a radiolabel. Most preferably, the detectable label is biotin, detected by enzyme conjugated streptavidin.

In all of the methods of the present invention which utilize an MBP, the MBP is preferably *E. coli* MutS protein, or a homologue thereof from a different prokaryotic or eukaryotic species.

In another embodiment, the present invention is directed to kits useful for carrying out the methods described above. Provided is a kit useful for detecting a mutation from a non-mutated sequence of a target polynucleotide sequence in a sample, the kit being adapted to receive therein one or more containers, the kit comprising:

(a) a first container containing an immobilizable mismatch-binding protein;

(b) a second container containing a solid support capable of immobilizing the mismatch binding protein; and (c) a third container or a plurality of containers containing a reagent or reagents capable of detecting the binding of a detectably labeled mismatch-containing nucleic acid duplex to the mismatch-binding protein.

In another embodiment, the invention provides a kit useful for detecting a mutation from a non-mutated sequence of a target polynucleotide sequence in a sample, the kit being adapted to receive therein one or more containers, the kit comprising:

(a) a first container containing a mismatch-binding protein immobilized on a solid support;

(b) a second container or a plurality of containers containing a reagent or reagents capable of detecting the binding of a detectably labeled mismatch-containing nucleic acid duplex to the protein.

In the above kits, the mismatch-binding protein is preferably *E. coli* MutS protein, or a homologue thereof from a different prokaryotic or eukaryotic species.

In the above kits, the solid support is selected from the group consisting of natural cellulose, modified cellulose, polystyrene, polypropylene, polyethylene, dextran, nylon, polyacrylamide, polyvinylidene difluoride, agarose and magnetic beads. A most preferred solid support is a nitrocellulose membrane.

The present invention is further directed to a composition useful for detecting the presence of a mismatch or mispairing in a test polynucleotide or oligonucleotide heteroduplex, comprising a mismatch-binding protein immobilized on a solid support or matrix. The mismatch-binding protein is preferably *E. coli* MutS protein, or a homologue thereof from a different prokaryotic or eukaryotic species. The solid support is preferably selected from the group consisting of natural cellulose, nitrocellulose or other modified cellulose, polystyrene, polypropylene, polyethylene, dextran, nylon, polyacrylamide, polyvinylidene difluoride, agarose and magnetic beads.

5' Biotin- GCACCTGACTCCTGGGGAGAAGTCTGCCGT -3' (SEQ ID NO: 1)

3'- CGTGGACTGAGGACTCCTCTTCAGACGGCA -5' (SEQ ID NO: 3)

The negative control was a 30-mer homoduplex described above containing a G:C match at the same position:

5' Biotin- GCACCTGACTCCTGGGGAGAAGTCTGCCGT -3' (SEQ ID NO: 1)

3'- CGTGGACTGAGGACCCCTCTTCAGACGGCA -5' (SEQ ID NO: 2)

Figure 4:
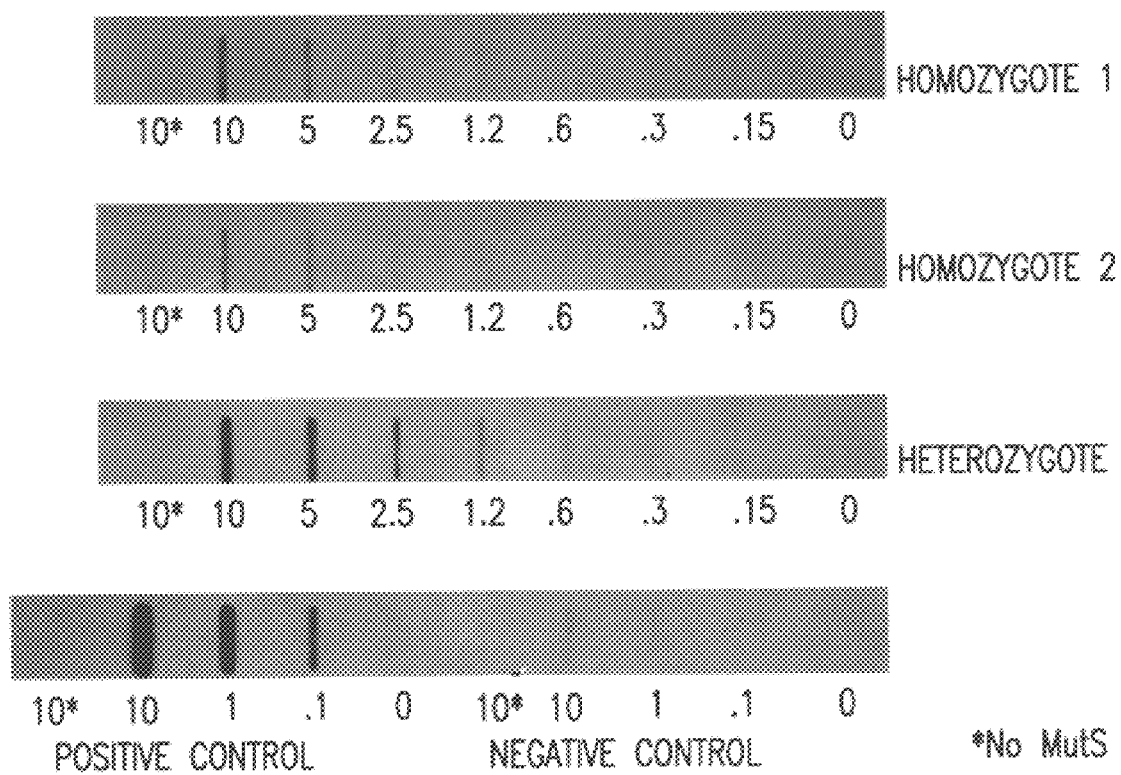
FIG. 4 shows the binding of homozygote and heterozygote DNA to immobilized MutS. The positive control was a G//T-containing 30-mer heteroduplex described above.
Figure 5A:
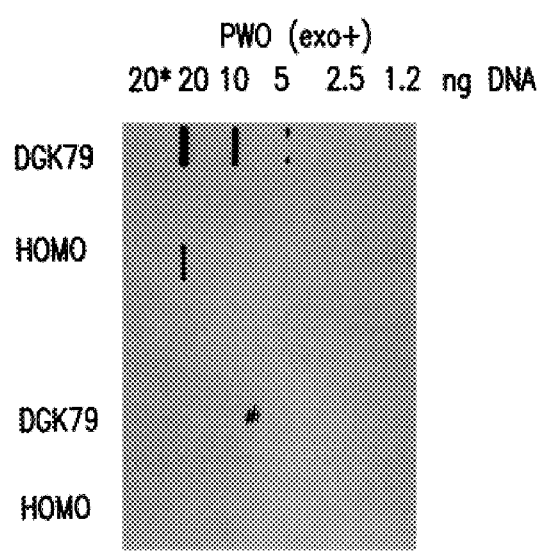
Figure 5B:
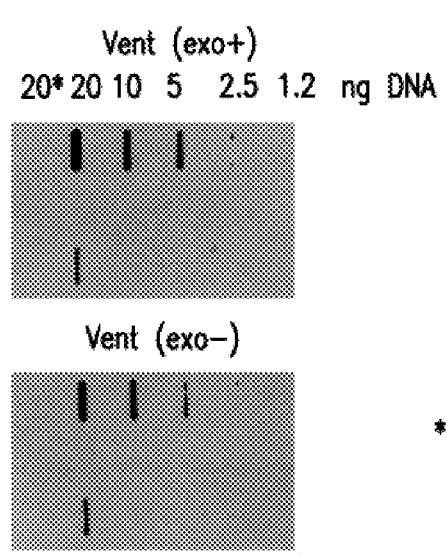
Figure 5C:
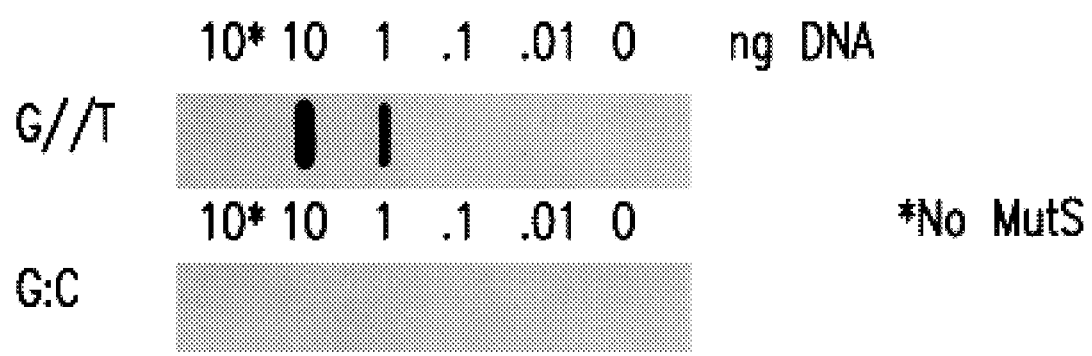

FIGS. 5A, 5B, and 5C show the binding of PCR amplified homozygote and heterozygote 230mer DNA duplexes to immobilized MutS. DGK79 refers to a heterozygous 230mer containing a G//A and T//C mismatches. HOMO refers to the homoduplex 230mer lacking any known mismatches. The DNA was amplified using three different polymerase preparations. Panel A shows results using PWO (exo+) (containing exonuclease). Panel B shows results using Vent (exo+) and Vent (exo−) (containing or lacking exonuclease activity, respectively). Panel C shows results with the positive and negative control 30mers used in FIG. 4.

Figure 6:
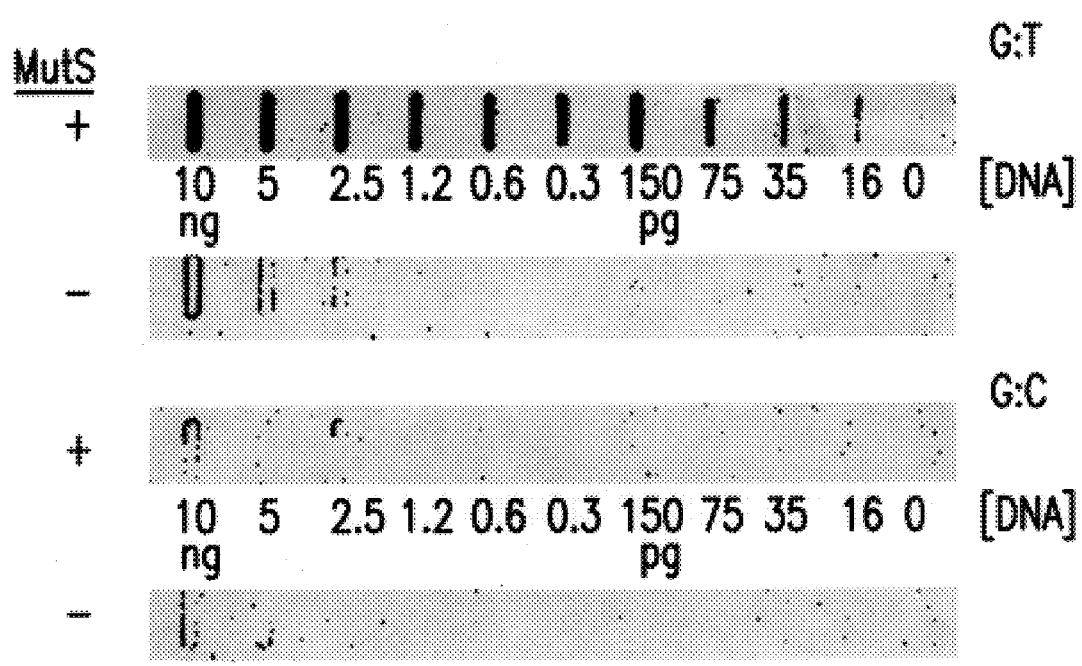

FIG. 6 shows the binding of mismatch containing DNA by MutS immobilized on PVDF. This study utilized the biotin label and the ECL assay.

Figure 7:
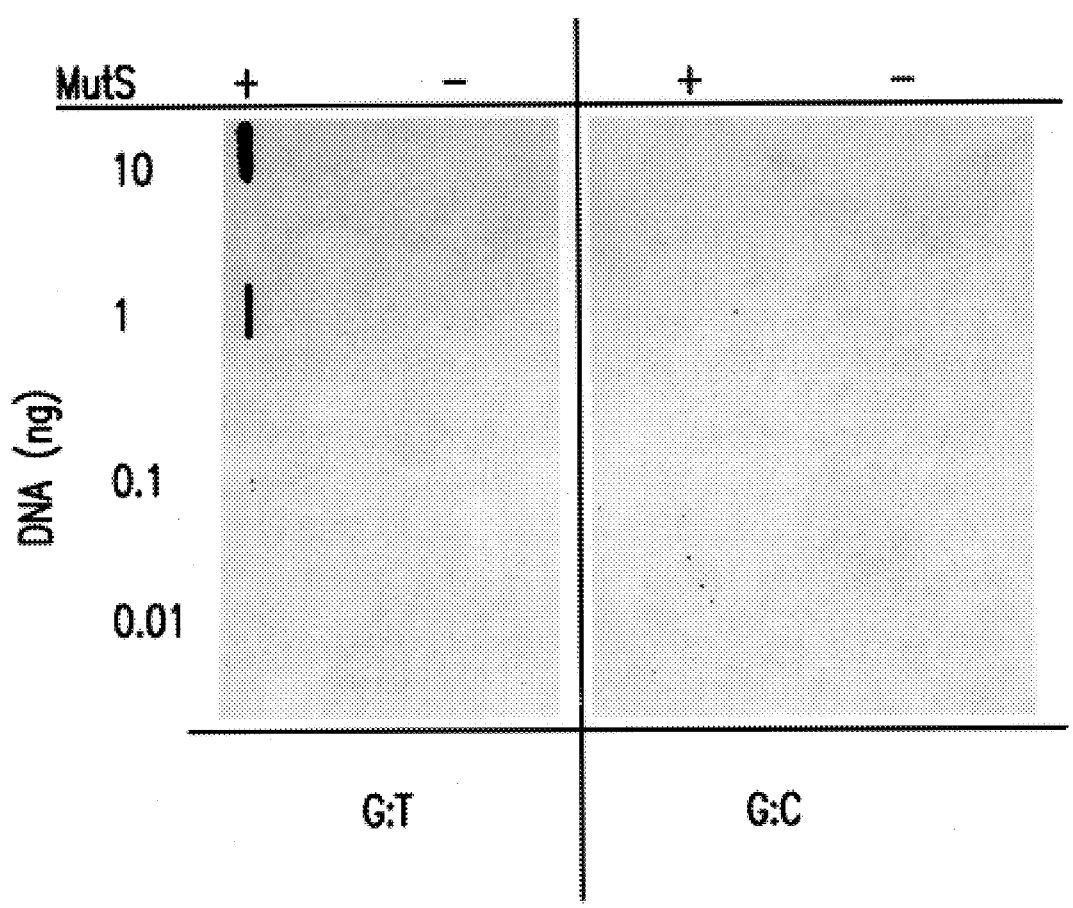
Figure 8:
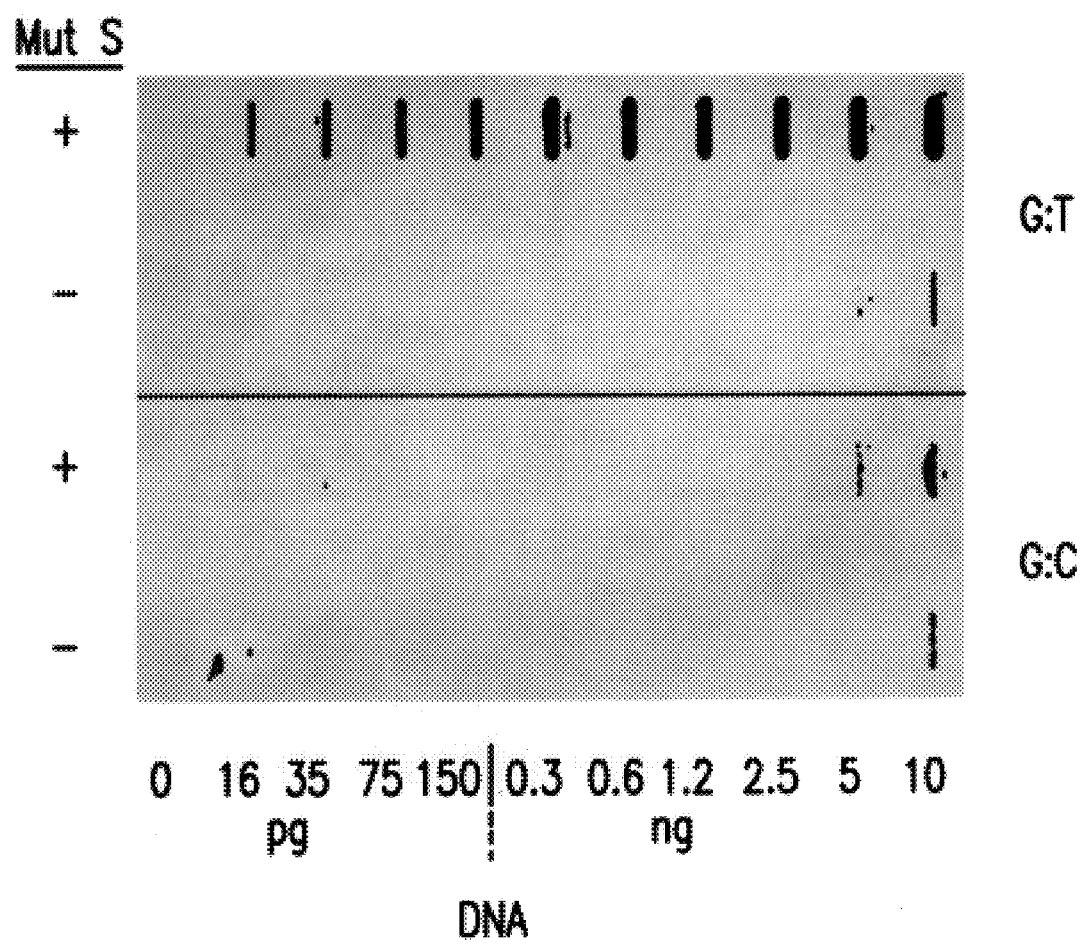

FIG. 7 shows the binding of mismatch containing DNA by MutS immobilized on nylon. This study utilized a $^{32}$P label and assayed bound radioactivity (by radioautography). the 30-mers described under FIG. 4 were utilized. Control slots: no MutS FIG. 8 shows the binding of DNA preparations to MutS immobilized on nitrocellulose as part of a comparison with binding to soluble MutS.

Figure 9A:
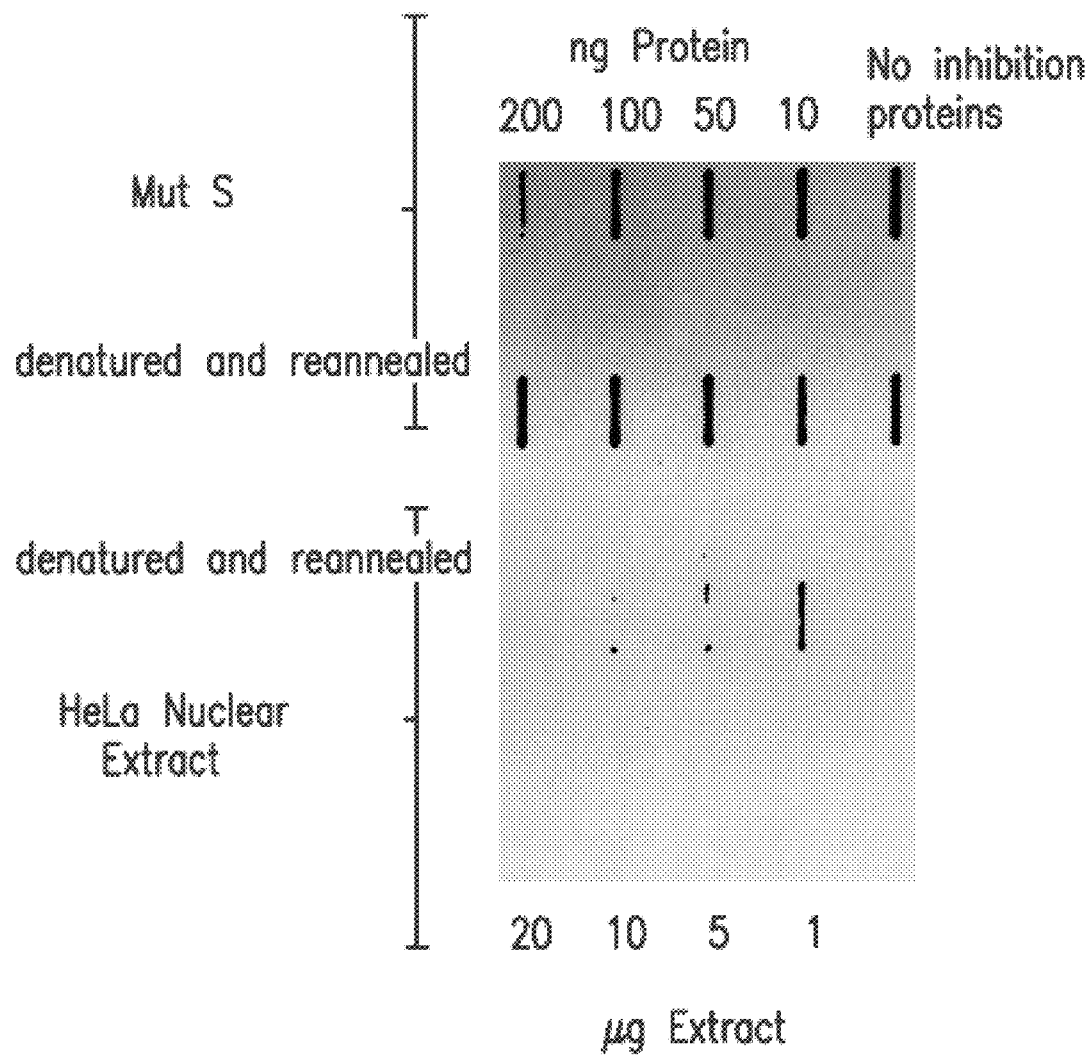
Figure 9B:
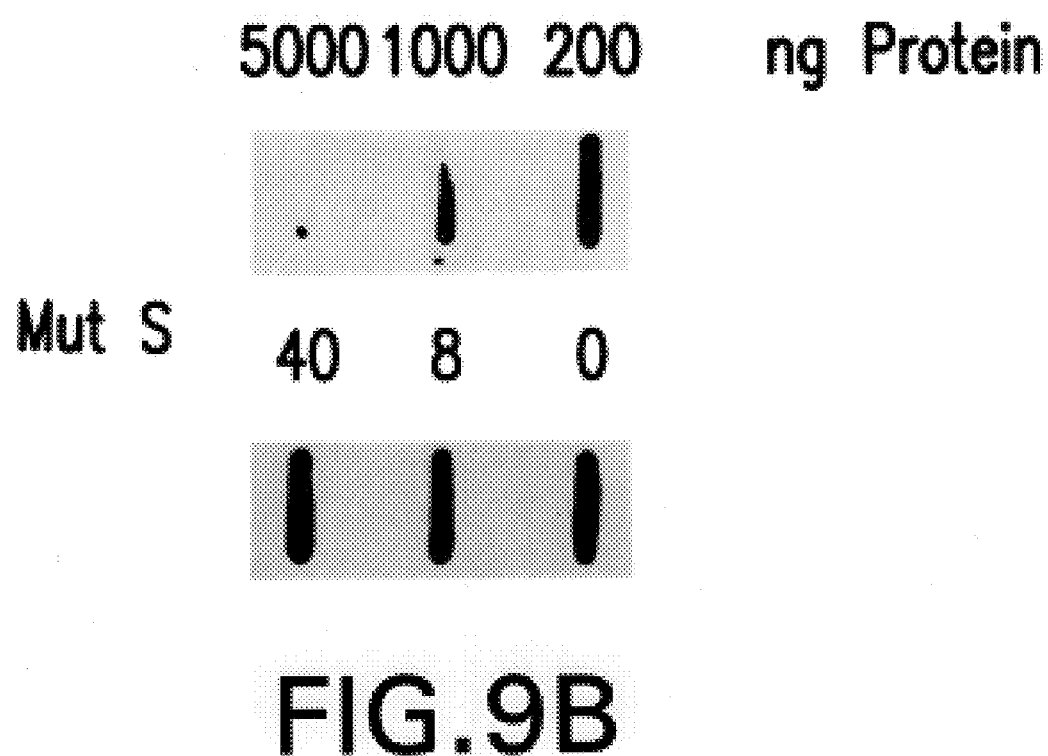

FIGS. 9A and 9B show the inhibition of the binding of mismatched DNA to MutS by soluble HeLa cell extract and soluble MutS. Panel A, upper half shows the inhibition by varying concentrations of soluble purified MutS of binding of 2 ng Bio-Het (G//T containing 30mers). Panel A, lower half, shows inhibition by varying concentrations of HeLa cell nuclear extract. The inhibition by both inhibitors is shown to be reduced by denaturing conditions. Panel B shows the inhibition by MutS at varying concentrations (up to 5 μg) of binding of 10 ng of Bio-Het to 500 ng immobilized MutS.

Figure 10:
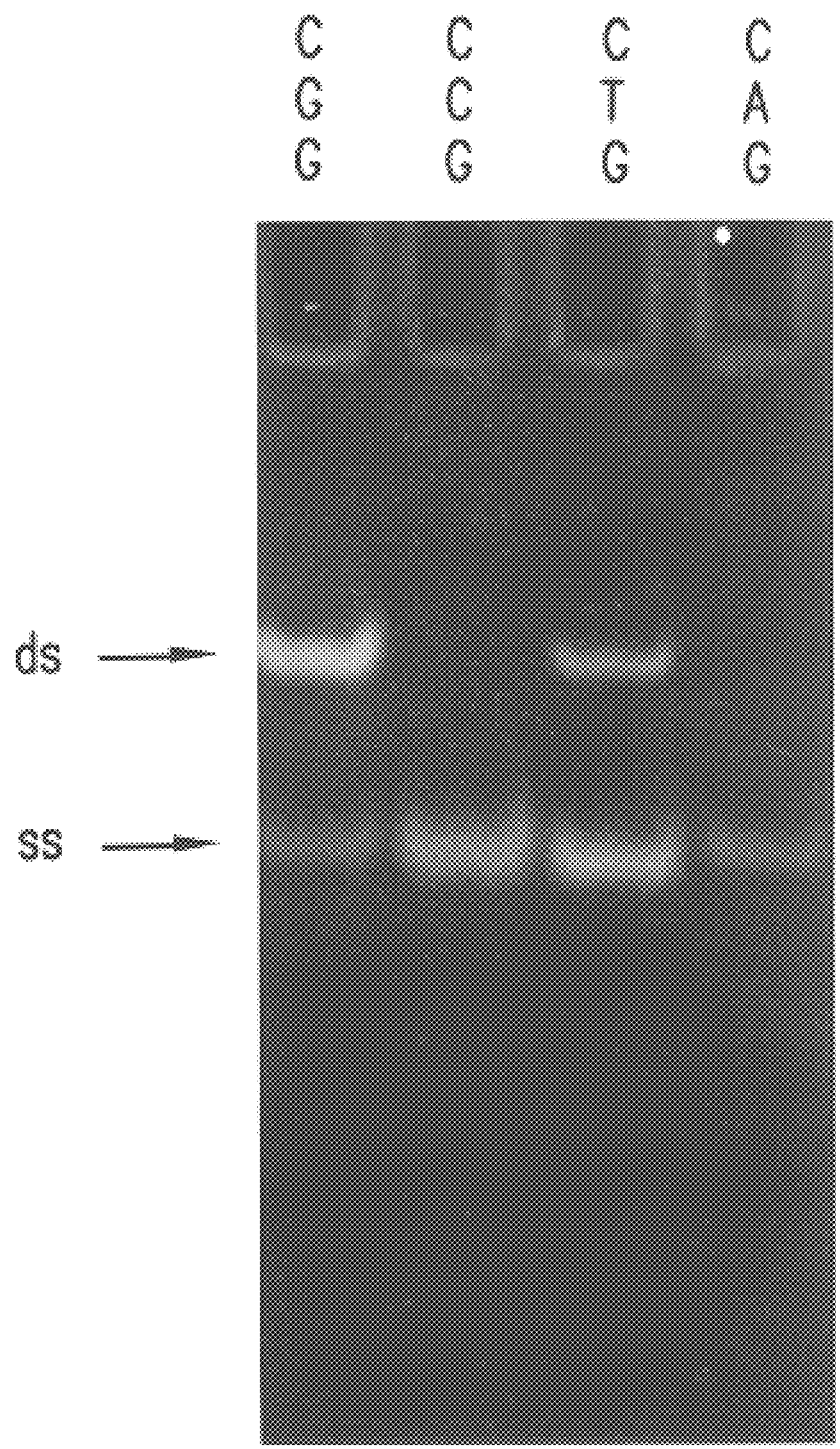

FIG. 10 shows the results of polyacrylamide gel electrophoresis of (CXG)$_{10}$ oligonucleotides. ds—double stranded 30mer. ss—single stranded 30mer.

Figure 11:
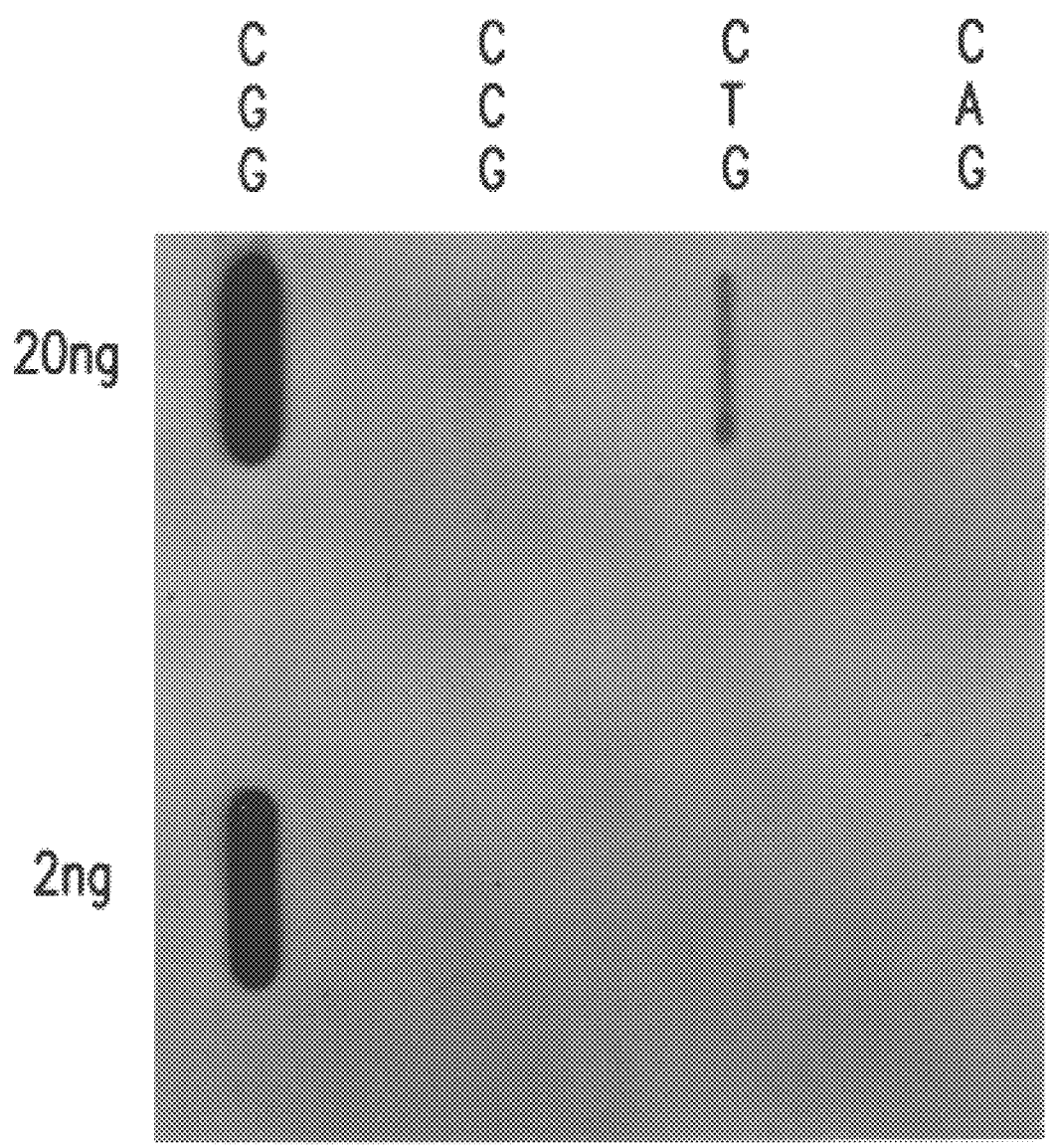

FIG. 11 shows the results of an immobilized mismatch binding protein assay of single stranded and double stranded triplet repeat block sequences. CCG: Single-stranded biotinylated CCG$_{10}$ 30mer. CGG: Single stranded biotinylated CGG$_{10}$ 30mer. CCG/CGG: Annealed double-stranded biotinylated CCG$_{10}$/CGG$_{10}$ 30mer. Column A: 1.3 ng DNA. Column B: 13 ng DNA. Exposure was for 30 sec.

FIG. 12A and FIG. 12B depict schematically an exemplary probe to detect triplet repeat blocks DNA and the relationship between probe length, repeat block length in test DNA and detectability by immobilized MBP.

Figure 13:
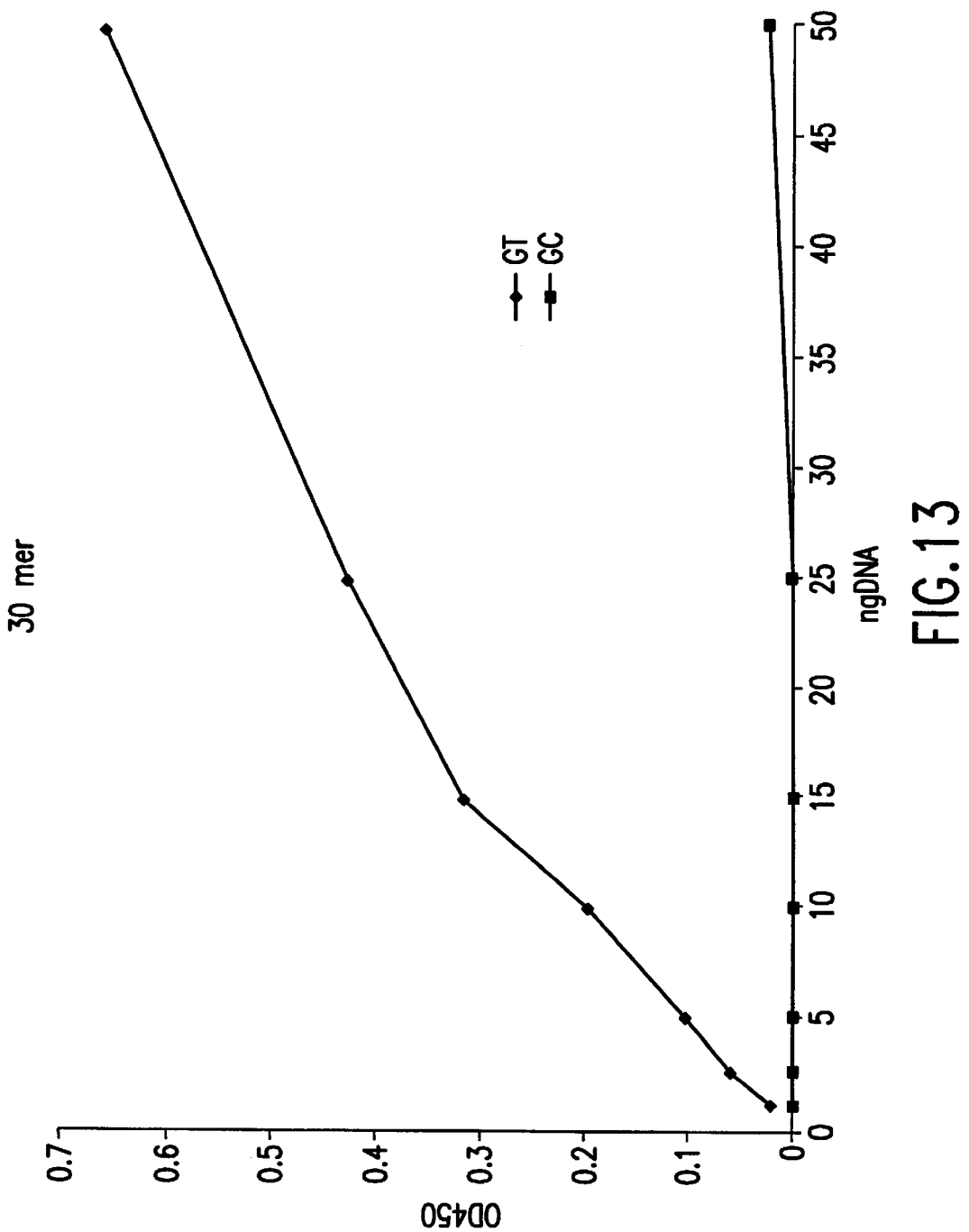

FIG. 13 is a graph showing the detection of mismatch (G//T)-containing DNA as a function of DNA concentration using MutS-immobilized on magnetic beads, biotin-conjugated DNA and streptavidin-horseradish peroxidase.

Figure 14:
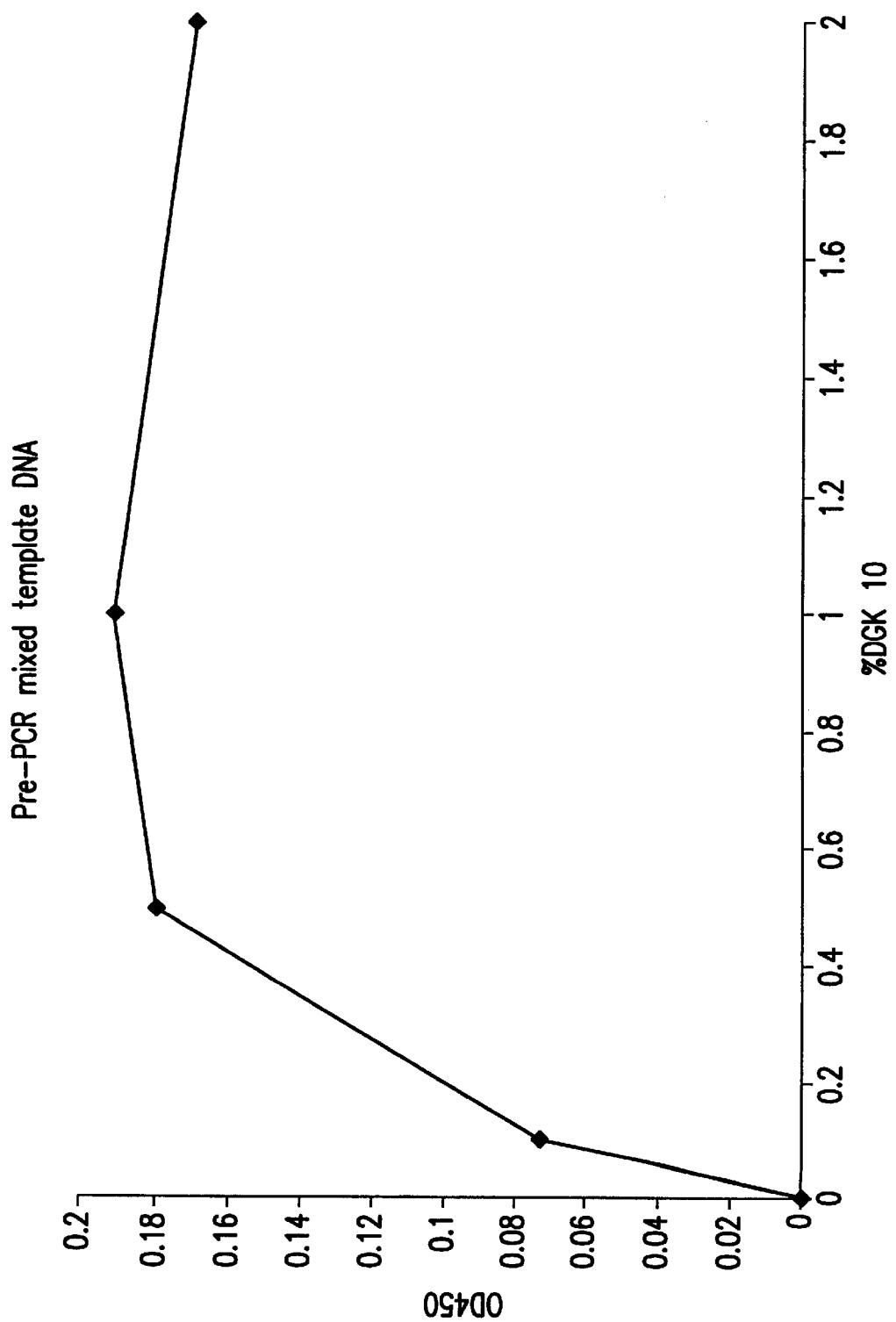

FIG. 14 is a graph showing the detection, using MutS immobilized on magnetic beads, of varying amounts of mismatch-containing minority sequence which has been added to a DNA sample. The mean OD$_{450}$ of duplicate samples is shown. Background (beads not exposed to DNA) has been subtracted.

Figure 15:
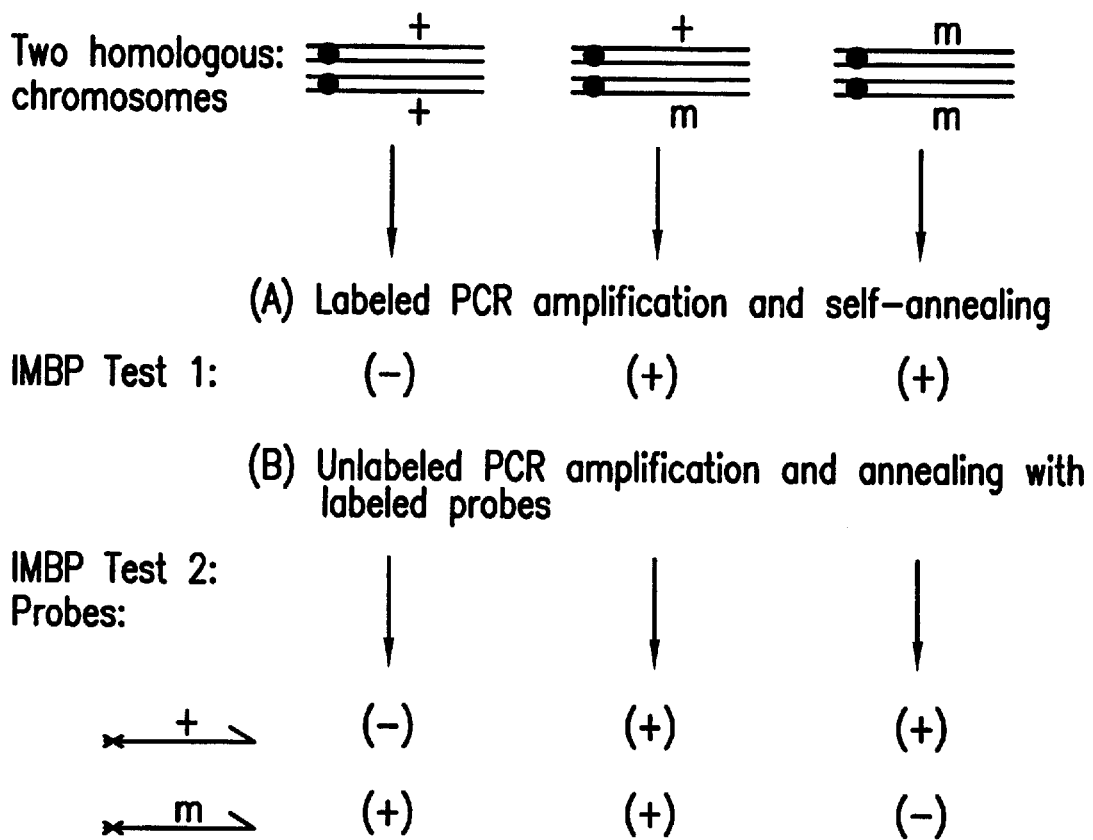

FIG. 15 is a schematic illustration of allele identification using immobilized MBP.

Figure 16:
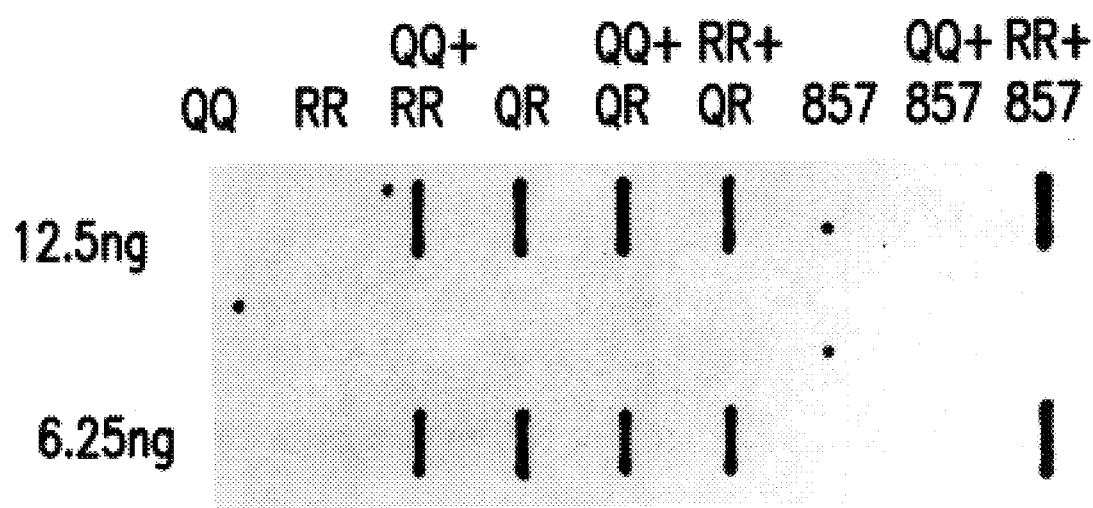

FIG. 16 shows the results of an immobilized mismatch binding protein assay to identify a specific allele in unknown DNA Sheep DNA samples of known genotype (QQ, RR and QR) and of an unknown genotype (857) were examined.

Figure 17:
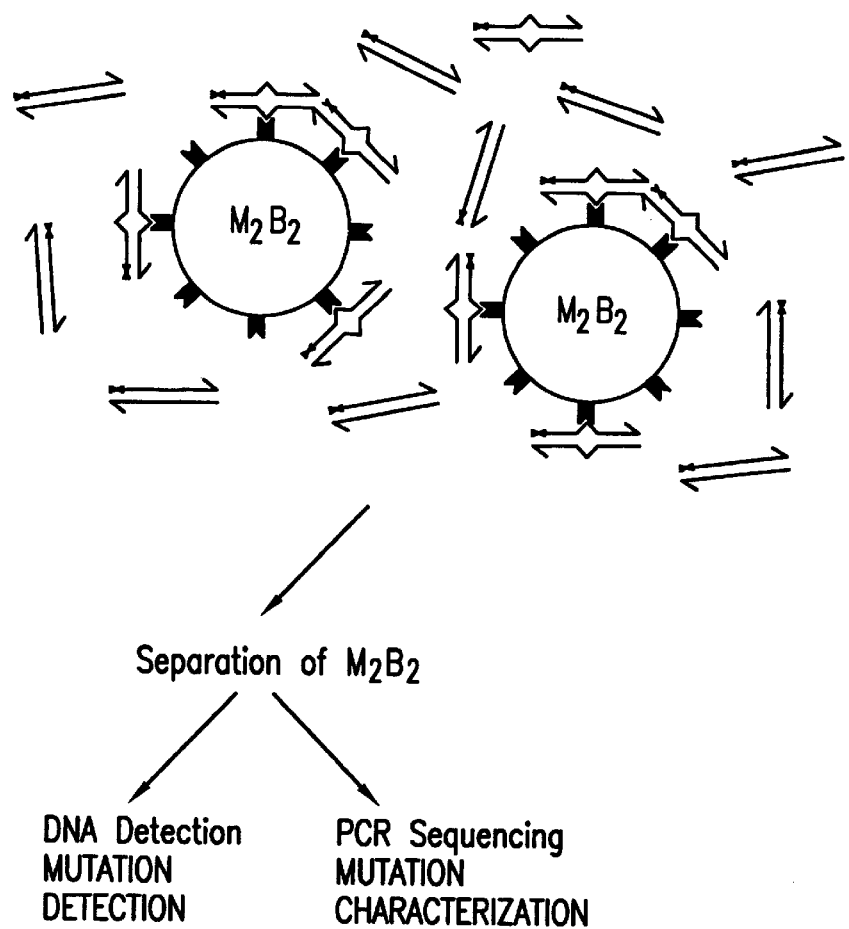

FIG. 17 is a schematic illustration of use of MBP immobilized on magnetic beads to detect and separate mismatch-containing DNA.

DESCRIPTION OF THE PREFERRED EMBODIMENTS

The present inventor conceived of a new, broadly applicable and relatively simple method for detecting a single base change in a DNA sequence or several such base changes. This method is based upon the formation of a mismatch-containing heteroduplex when a strand of mutant DNA and a "complementary" strand of wild-type DNA hybridize.

The presence of the mismatch is detected in a highly specific manner by first allowing the DNA to bind to an immobilized mismatch-binding protein (MBP), such as the MutS protein of *E. coli*. The presence of DNA bound to the MBP is then detected in any of a number of ways, depending on the label used and whether the assay is a direct assay or a competitive assay. This method stands in stark contrast to methods of the prior art which employ mismatch cutting nuclease enzymes capable of breaking DNA at or near a mispaired base pair. The present method provides an increase in sensitivity of anywhere from greater than 5-fold to usually approaching 1000-fold in detection of those mismatches and mispairings detected by the same MBP in solution. A major advantage of the present assay lies in the fact that immobilized MBP (as shown with *E. coli* MutS) binds little or no homoduplex DNA even at relative high concentrations, in comparison with binding of homoduplex by MutS in solution, thereby allowing the powerful discriminatory ability of this assay.

The methods described herein provide a mutation/polymorphism detection system having the advantages of (a) simplicity, (b) accuracy, (c) ability to be used without radioactivity, (d) ability to detect all single base substitution mutations and addition or deletion mutations of 14 bases. The present invention also provides a method for detecting a functional MBP, or a deficiency thereof, in a sample, which is useful for screening normal or tumor cells for mismatch repair deficiencies. Such assays are important in the diagnosis of susceptibility to certain types of cancer.

Standard reference works setting forth the general principles of recombinant DNA technology and cell biology, and describing conditions for isolation and handling of nucleic acids, denaturing and annealing nucleic acids, hybridization assays, and the like, include: Sambrook, J. et al., *MOLECULAR CLONING: A LABORATORY MANUAL,* 2nd Edition, Cold Spring Harbor Press, Cold Spring Harbor, N.Y., 1989; Albers, B. et al., *MOLECULAR BIOLOGY OF THE CELL,* 2nd Ed., Garland Publishing, Inc., New York, N.Y., 1989; Watson, J. D., et al., *MOLECULAR BIOLOGY OF THE GENE,* Volumes I and II, Benjamin/Cummings Publishing Co., Inc., Menlo Park, Calif., 1987; Darnell J. E. et al., *MOLECULAR CELL BIOLOGY,* Scientific American Books, Inc., New York, N.Y., 1986; Lewin, B. M., *GENES II,* John Wiley & Sons, New York, N.Y., 1985, which references are hereby incorporated by reference in their entirety.

MBPs are proteins of around 100 kDa, have been identified in and isolated from both bacteria and higher organisms and selectively bind DNA containing mismatched bases. MBPs have been found in yeast (Valle G et al., 1991 *Yeast* 7:981–988; Miret J. J. et al., 1993, *J. Biol Chem.* 268:3507–3513), as well as in humans (Stephenson, C. et al., 1989, *J. Biol. Chem.* 264:21177–21782; Karran, P et al., 1990, *Mutat. Res.* 236:269–275; Hughes M. J. et al., 1992, *J. Biol. Chem.* 267:23876–23882; Reenan, A. G. et al., 1993, *Genetics* 132:963–973; Reenan, A. G. et al., 1993, *Genetics* 132:975–985). Mismatch binding proteins from Xenopus and from mouse have been cloned by M. Radman and colleagues (Varlet et al, *Nucl. Acid Res.* 22:5723–5757 (1994)).

A preferred MBP is characterized by its ability to bind DNA-DNA (or DNA-RNA or RNA-RNA) duplexes containing mispaired or unpaired bases, to the significant exclusion of single stranded polynucleotides or perfectly matched duplexes. MBP binding to DNA duplexes is exemplified below. However, the fact that uridine is present in RNA while thymidine is absent does not preclude detection of RNA:DNA or RNA:RNA duplexes.

RNA:DNA duplexes contain thymidine in the DNA strand and are expected to be bound by the MBP. An RNA:DNA mismatch-containing duplex could include a detectable G//T mispairing, which is among those most readily detectable by the present methods. *E. coli* MutS (in solution) is known to detect G//T, G//G and A//C mismatches (Wagner et al. PCT publication WO93/02216). Based on testing using nuclease protection, MutS is known to bind to all 8 possible mismatches in DNA (Su et al. (supra). All but thymidine-containing mismatches can occur and be detected in RNA:RNA duplexes. The only other chemical difference between DNA and RNA, the presence of the sugar deoxyribose vs. ribose in the sugar-phosphate backbone, is not known or expected to have any effect on binding of a mismatch-containing heteroduplex to MutS or any other MBP. Thus, while the preferred embodiments of the present invention are directed to detection of DNA-DNA duplexes, the methods disclosed herein are useful for detecting mismatches in any "polynucleotide" (or oligonucleotide) molecule, including RNA.

Peptide nucleic acid (PNA) is a DNA analogue with a protein-like backbone typically consisting of N-(2-aminoethyl)glycine units. Hence the backbone is held together by amide rather than by phosphodiester bonds. PNA mimics DNA in forming Watson-Crick complementary duplexes with normal DNA. Two complementary PNA strands can hybridize to one another to form a helical duplex (Wittung, P. et al., *Nature* 368:561–563 (1994); Nielsen P. E. et al., *Bioconjug. Chem.* 5:3–7 (1994); Bohler, C. et al., *Nature* 376:578–581 (1995); for a review, see Frank-Kamenetskii, M. D. et al., *Annu. Rev. Biochem.* 64:65–95 (1995)). Demidov V. V. et al. (*Proc. Natl. Acad. Sci. USA* 92:2637–2641 (1995)) elucidated the mechanism of recognition of double-stranded DNA homopyrimidine polyamide PNA leading to the strand displacement. The sequence specificity of the recognition is essentially provided at the "search" step of the process, which consists in the highly reversible transient formation of duplex between one PNA molecule and the complementary strand of duplex DNA while the other DNA strand is displaced. This search step is followed by virtually irreversible "locking" step via PNA2/DNA triplex formation. The binding of homopyrimidine PNA to dsDNA meets two apparently mutually contradictory features: high sequence specificity of binding and remarkable stability of both correct and mismatched PNA-PNA-DNA complexes. PNA oligomers have been used to detect single base mutations through PCR clamping. PNA can be used to provide enhanced amplification (Demers, D. B. et al., *Nucl. Acid Res.* 23:3050–5 (1995)). Other references which describe formation of PNA-DNA hybrids include Peffer, N. J. et al., *Proc. Natl. Acad. Sci. USA* 90 10648–10652 (1993); Iyer, M. el al., *J. Biol. Chem.* 270 14712–14717 (1995); Vickers, T. A., *Nucl. Acid Res.* 23:3003–3008 (1995)).

The present invention includes the use of an immobilized MBP to bind to and detect any of the following duplexes or triplexes containing the base pair mismatch or other mispairing which the MBP is capable of recognizing: a DNA-PNA duplex, a PNA-PNA, a RNA-PNA duplex, DNA triplex containing a third strand of either PNA or RNA, a DNA-RNA-PNA triplex, a PNA-PNA-DNA triplex. In a preferred embodiment, instead of using a labeled oligonucleotide probe, as described herein, to anneal to a test DNA to produce a detectable mismatch, a PNA having the same mismatch-producing sequence is used. Because PNA containing hybrids form more stable helices, immobilized MBP used with a PNA-DNA rather than a DNA-DNA heteroduplex will allow improved detection of mismatches which are poorly recognized by the MBP (in conventional DNA duplexes), for example, C//C mismatches.

Mismatch Binding Protein and Derivatives

In a preferred embodiment, the intact native MutS protein from *E. coli* is used. However, as used herein, the term "mismatch binding protein" or "MBP" is intended to encompass a functional derivative of the intact, native protein. By "functional derivative" is meant a "fragment," "variant," "analog," or "chemical derivative" of the protein which retains the ability to bind to a mismatch-containing nucleic acid heteroduplex, which permits its utility in accordance with the present invention.

A "fragment" of a MBP refers to any subset of the molecule, that is, a shorter peptide. A "variant" of the protein refers to a molecule substantially similar to either the entire protein or a DNA-hybrid-binding fragment thereof A variant of a mismatch-binding protein, for example, of MutS, may be prepared by recombinant DNA methods well-known in the art. A preferred functional derivative of MutS is a homologue of *E. coli* MutS in another species. The term homologue (or homologue) as used here in is well-defined in the art, and can be described as any member of a set of genes or DNA sequences from different organisms whose nucleotide sequences show a high degree of one-to-one correspondence (see, for example, Micklos, D. A. et al., *DNA SCIENCE,* Cold Spring Harbor Press, 1990, p. 468).

Examples of *E. coli* MutS homologues are the MutS protein of *Salmonella typhimurium* (Lu, A. L. et al., supra;

Haber L. T. et al., supra; Pang, P. P. et al., supra) and the hexA protein of *Streptococcus pneumoniae* (Priebe S. D. et al., supra; Haber et al., supra). In addition, eukaryotic homologues of MutS or HexA can also be used, such as those encoded by the homologous sequences identified in yeast, human, mouse, frog or hamster DNA (Shimada, T. et al., *J. Biol. Chem.* 264:20171 (1989); Linton, J. et al., *Molec. Cell Biol.* 7:3058–3072 (1989); Fujii, H. et al., *J. Biol. Chem.* 264:10057 (1989)).

The homology between MutS homologues in prokaryotic and eukaryotic species is illustrated in Reenan et al., *Genetics* 132:963–973 (1992), where the *E. coli* MutS nucleotide sequence is shown to be highly homologous in one region to *S. typhimurium* MutS, *S. pneumoniae* hexA, mouse Rep-1, and human DUC-1. PCR primers which successfully led to the cloning of *Saccharomyces cerevisiae* (yeast) homologues of MutS, named MSH1 and MSH2, were based on this homology. This reference shows the amino acid sequence homology between yeast MSH1, MSH2 and *E. coli*, *S. typhimurium* and *S. pneumoniae* MutS homologues. New et al., *Mol. Gen. Genet.* 239:97–108 (1993) disclosed another yeast gene, MSH3, which is a homologue of eukaryotic MutS and indicates the most conserved sequences among MutS, HexA and mouse REP-3. A search for a new yeast gene based on this sequence homology led to discovery of yeast MSH3. R. Fishel et al., *Cell* 75:1027–1029 (1993) describes the cloning of a another human MutS homologue (hMSH2) using for PCR the homologous sequences from other MutS homologues as described by Reenan et al., supra).

Therefore, any homologue of *E. coli* MutS which recognizes DNA mismatches (single base mismatches or 1–4 unpaired bases) is included within the scope of the present invention.

A "chemical derivative" of the MBP contains additional chemical moieties not normally a part of the protein, including additional stretches of amino acids as in a fusion protein. Covalent modifications of the peptide are included within the scope of this invention. Such modifications may be introduced into the molecule by reacting targeted amino acid residues of the protein with an organic derivatizing agent that is capable of reacting with selected side chains or terminal residues.

In selecting a protein as being a useful MBP for the methods of the present invention, assays can be performed by one of ordinary skill in the art using conventional methods of the prior art. However, novel methods described herein are preferred and are particularly well-suited for a simple screening method to detect a candidate MBP in a sample such as a cell extract. This method, described in more detail below, utilizes competitive binding of the unknown MBP to a known mismatch containing oligonucleotide to inhibit binding of a standard, known MBP such as *E. coli* MutS. Thus, in evaluating a candidate MBP, (or homologue or functional derivative) for utility in the present invention, a mismatch binding assay is performed using a known mismatch-containing heteroduplex. For screening cell extracts, or preferably, for evaluating the binding activity of a candidate MBP which has been identified, the cell extract or purified or semipurified candidate MBP is immobilized, as disclosed herein, and its binding to mismatch- or mispair-containing heteroduplexes is examined, for example, in an immobilized filter binding assay. To prepare the oligonucleotide heteroduplex, an oligonucleotide, preferably of about 30 bases, may be labeled with $^{32}$P using a linase reaction with γ-$^{32}$P-ATP and any appropriate kinase, for example, T4-polynucleotide linase. Longer oligonucleotides may also be used. Alternatively, the oligonucleotide can be labeled with biotin at the 5'-end of one strand, as described below. The 5'-labeled oligonucleotide (which can be stored at −20° C.) is then annealed with a complementary oligonucleotide to form the desired mismatch under standard conditions. As described in more detail below for the competitive assay, the annealed heteroduplex is mixed with the preparation being tested for MBP activity and immobilized MutS. Alternatively, the labeled heteroduplex is mixed with the test MBP which has been immobilized as described herein. The heteroduplex is allowed to bind to the immobilized MutS or test MBP and label associated with the solid phase is determined. In the competitive assay, a decrease in bound heteroduplex compared to a control indicates the presence of an MBP recognizing the mismatch in the unknown. (In the direct assay, the presence of bound heteroduplex indicates that an MBP was bound to the solid phase.) Thus, by using such a simple assay, one can easily detect and select a MBP useful in the methods of the present invention.

As used in the detection, screening and "clean-up" methods of the present invention, the MBP is immobilized to a solid support or carrier. By "solid support" or "carrier" is intended any support capable of binding a protein while permitting washing without dissociating from the protein. Well-known supports or carriers include, but are not limited to, natural cellulose, modified cellulose such as nitrocellulose, polystyrene, polypropylene, polyethylene, polyvinylidene difluoride, dextran, nylon, polyacrylamide, and agarose or Sepharose®. Also useful are magnetic beads. The support material may have virtually any possible structural configuration so long as the immobilized MBP is capable of binding to the target nucleic acid molecule. Thus, the support configuration can include microparticles, beads, porous and impermeable strips and membranes, the interior surface of a reaction vessel such as test tubes and microtiter plates, and the like. Preferred supports include nitrocellulose disks or strips. Those skilled in the art will know many other suitable carriers for binding the MBP or will be able to ascertain these by routine experimentation.

Most preferred is a solid support to which the MBP is attached or fixed by covalent or noncovalent bonds. Preferably, noncovalent attachment is by adsorption using methods that provide for a suitably stable and strong attachment. The MBP is immobilized using methods well-known in the art appropriate to the particular solid support, providing that the ability of the MBP to bind mismatch-containing DNA is not destroyed. For a review of protein immobilization and its use in binding, assays, see, for example, Butler, J. et al. In: Van Regenmortel, M. H. V., ed., *STRUCTURE OF ANTIGENS*, Volume 1, CRC Press, Boca Raton, Fla., 1992, pp. 209–259. Immobilization may also be indirect, for example by the prior immobilization of a molecule which binds stably to the MBP or to a chemical entity conjugated to the MBP. For example, an antibody (polyclonal or monoclonal)specific for the MBP may be immobilized by passive adsorption or covalent attachment. The MBP is then allowed to bind to the antibody, rendering the MBP immobilized. Indirect immobilization, as intended herein, includes bridging between the MBP and the solid surface using any of a number of well-known agents and systems. For example, the "Protein-Avidin-Biotin-Capture" (PABC) system is described by Suter, M. et al., *Immunol. Lett.* 13:313–317 (1986). In such a system, any biotinylated protein is immobilized by passive adsorption (or covalent linking) to the solid phase. Streptavidin, which is multivalent, binds with high affinity to the biotin sites on the immobilized protein while maintaining available binding sites for biotin in solution. The MBP, in biotinylated form, is then allowed to bind to the immobilized streptavidin, rendering the MBP immobile. Alternatively, the streptavidin can be passively adsorbed or covalently bound to the solid phase without the intervening protein. An MBP immobilized by any of the foregoing approaches (provided that they do not interfere with its ability to bind and retain mismatch containing oligo- or polynucleotides) is within the scope of the present invention.

The immobilized MBP is then used in a simple, economical assay to detect heterozygosity (or polymorphism) as well as single base mutations and expanded trinucleotide repeats, or to isolate mismatch-containing DNA from a mixture, to rid a mixture of mismatch-containing DNA, etc.

In one embodiment, the surface of polystyrene or other plastic multiwell plates serves as the solid support. In another embodiment, a solid support to which the MBP is bound is affixed to the bottom or placed loosely in the wells of multiwell plates. Multiwell plates in which the bottoms of the wells comprise nitrocellulose or a similar membrane material and through which liquid can be moved under pressure or vacuum may also be used.

In a preferred embodiment, the immobilization to a filter followed by DNA binding are performed in a 96- or 48-well blotting apparatus and the resulting sheet of nitrocellulose (or other support) filter material is removed from the apparatus to evaluate reactions. For example, color development on the nitrocellulose can be used to evaluate binding where the detection system comprises an enzyme and a chromogenic or chemiluminescent substrate for the enzyme serving as the precursor of the detectable colored product.

Following attachment of the MBP to the support, the support is preferably treated ("blocked") to prevent further binding of proteins or nucleic acids, using methods and reagents well-known in the art, for example, incubation with a solution containing bovine serum albumin (BSA).

The immobilized MBP is contacted with, and allowed to bind (to saturation) to, small oligonucleotide heteroduplex molecules. The oligonucleotides preferably have about 30 base pairs. For testing, one uses a DNA duplex containing a mismatch which is well recognized (i.e., bound and retained) by the MBP.

PREPARATION OF OLIGONUCLEOTIDES WITH OR WITHOUT MISMATCHES

Such oligonucleotides are prepared using a detectably labeled nucleotide, preferably modified at the 5' end with a detectable label, such that they can be quantitatively detected by appropriate detection methods, preferably spectrophotometry or chemiluminescence. As used herein, the term "detectable label" is intended to include not only a molecule or label which is "directly" detected (e.g., a radionuclide or a chromogen) but also a moiety such as biotin, which is "indirectly" detected by its binding to a second (or third) binding partner one of which carries the "direct" label. In a preferred embodiment, the oligonucleotide is biotin-modified, and is detectable using a detection system based on avidin or streptavidin which binds with high affinity to biotin. The avidin or streptavidin is preferably conjugated to an enzyme, the presence of which is detected by allowing the enzyme to react with a chromogenic substrate and measuring the color developed. If the PABC system is used to immobilized the MBP, it is important that no free biotin sites on either the initially immobilized protein or the biotinylated MBP be available for reaction in the detection phase of the assay. Thus, it may be necessary to use a detection system other than biotin/streptavidin when the PABC system is employed to immobilize the MBP Non-limiting examples of useful enzymes in the methods of the present invention are horseradish peroxidase (HRP), alkaline phosphatase, glucose-6-phosphate dehydrogenase, malate dehydrogenase, staphylococcal nuclease, delta-V-steroid isomerase, yeast alcohol dehydrogenase, α-glycerophosphate dehydrogenase, triose phosphate isomerase, asparaginase, glucose oxidase, β-galactosidase, ribonuclease, urease, catalase, glucoamylase and acetylcholinesterase.

Other examples of detectable labels are: (1) a radioisotope which can be detected by such means as the use of a gamma counter or a scintillation counter or by autoradiography; (2) a fluorescent compound, which, when exposed to light of the proper wave length, becomes detectable due to it fluorescence and is measured by microscopy or fluorometry. Commonly used fluorescent labelling compounds include fluorescein isothiocyanate, rhodamine, phycoerythrin, phycocyanin, allophycocyanin, o-phthaldehyde and fluorescamine. The detectable label may be a fluorescence emitting metal such as $^{152}$Eu, or others of the lanthanide series which can be attached to the oligonucleotide using metal chelating groups such as diethylenetriaminepentaacetic acid or ethylenediaminetetraacetic acid.

The detectable label may be a chemiluminescent compound, the presence of which is detected by measuring luminescence that arises during the course of a chemical reaction. Examples of useful chemiluminescent labeling compounds are luminol, isoluminol, theromatic acridinium ester, imidazole, acridinium salt and oxalate ester. Likewise, a bioluminescent compound may be used to label the oligonucleotide and is detecting by measuring luminescence. In this case, a catalytic protein increases the efficiency of the chemiluminescence reaction. Examples of useful bioluminescent labeling compounds include luciferin, luciferase and aequorin.

Mismatch-containing DNA-DNA, DNA-RNA or RNA-RNA duplexes can be detected either directly or indirectly. For direct detection, the poly- or oligonucleotide duplex is detectably labeled using labels as discussed herein. For indirect detection, the assay utilizes competition of binding to the MBP of the test DNA with an already bound or a contemporaneously exposed mismatch-containing oligo- or polynucleotide duplex. Thus, for example, a labeled mismatch-containing DNA oligonucleotide is pre-bound to the MBP or is incubated together with the MBP and test DNA. The more mismatch-containing DNA in the test sample, the less binding of the labeled oligonucleotide to the MBP will occur.

The test sample to be assayed can be in any medium of interest, and will generally be a samples of medical, veterinary, environmental, nutritional, or industrial significance. Human and animal specimens and biological fluids particularly can be assayed by the present method, providing that they contain cells from which nucleic acids can be prepared. Preferred sources include blood, sperm, other tissue (particularly tumor tissue or cells), milk, urine, cerebrospinal fluid, sputum, fecal matter, lung aspirates, throat swabs, genital swabs and exudates, rectal swabs, and nasopharyngeal aspirates. Preferred biological fluids in which the presence or absence of a functional MBP may be determined according to this invention include cells and cell extracts or any body fluid as above, or a protein-containing fraction of such an extract or fluid.

A key advantage of the present invention stems from the use of an immobilized MBP, as compared to a soluble MBP, for detecting mismatch-containing DNA. This discovery by the present inventor did not flow naturally from the teachings in other related fields such as the immunoassay art. First, the fact that a complex "AB" of two components (A and B) formed in solution binds to a solid support Z to yield ABZ does not ensure that A will interact effectively with BZ or that B will interact effectively with AZ. The order in which A and B bind to form a complex may be significant. This is especially noteworthy in the case of MutS or other MBPs which function physiologically as part of a complex pathway of mismatch repair. MutS recognition is particularly targeted to a minimal deviation from a normal base paired structure, while being non-existent for the normal base pair. In other words, almost counter-intuitively, the more a mismatch "looks like a match," the more likely it is to be recognized by MutS (Fazakerley et al., *EMBO J.* 5:3697–3703 (1986)). Thus, for example, MutS varies from (1) absolutely no recognition of a G:C match to (2) optimal recognition of the most minimal (as determined by nuclear magnetic resonance) mismatch G//T, to (3) poor recognition of a more distinct mismatch, C//C. In contrast, antibody recognition and binding of a particular antigenic structure or epitope gradually declines as the structure of the epitope is gradually modified, antibody until the epitope structure is sufficiently distinct from the original antigen that no recognition is observed. The "recognition pattern" of MutS for C//C, G//T and G:C would never have been predicted from knowledge of antibody-antigen recognition. For the foregoing reasons, lessons learned from analysis of the recognition and binding of antigens by antibodies cannot be applied in an overly simple manner to the recognition and binding of nucleic acids by MutS in the methods of the present invention.

As discussed in the Background section, there appear to be three levels of interaction between MutS and mismatch-containing DNA in vitro based on the disclosure of S-S. Lu et al. (supra), Su et al. (supra), Jiricny et al. (supra) and Modrich et al. (U.S. Pat. No. 5,459,0395). All appear to be mismatch-specific. These interactions are ranked from weak to strong (or from unstable to stable), below:

1. Footprinting interactions. These interactions are observed in nuclease protection and competition experiments. All mismatches are recognized.
2. Repair interactions. These interactions are observed in in vitro repair experiments in the presence of other components of the *E. coli* mismatch repair system. All mismatches except C//C are recognized, and the pattern of recognition appears to be identical to that of mismatch repair in vivo.
3. Binding interactions. These interactions are observed in filter binding and band-shift experiments. Only the best repaired mismatches appear to be bound. Binding requires stable, retentive interaction.

The present inventor was the first to develop an assay using an immobilized mismatch binding protein (e.g., MutS) to detect mutations by detecting mismatches. Given that detection of mismatch-containing DNA by immobilized MutS would appear to require a binding interaction involving retention of substrate, it would be expected by one skilled in the art that the recognition pattern would be of the type descried as #3 above, i.e., detection should be limited to the very well-detected mismatches but not all mismatches. However, the results reported herein clearly indicate that immobilized MutS binds and retains all mismatches except C//C (which is, at best, only poorly recognized). See also: Wagner et al., 1995, *Nucl. Acid Res.* 23:3944–3948 (1995).

Thus, the interaction between immobilized MutS and mismatch-containing DNA more closely resembles the repair interactions than the binding interactions described above, although they clearly require retentive binding. This unexpected finding indicates that the immobilized MutS of the present invention mimics MutS acting in the repair process. This would occur through alteration of the MutS by immobilization such that it no longer resembles MutS in solution, but rather resembles MutS which has interacted with the second protein in the repair pathway (MutL). It is noteworthy, however, that during repair, the interaction of MutL with MutS requires that MutS first have interacted with mismatch-containing DNA. This is clearly not a requirement of the interactions of immobilized MutS according to the present invention.

Furthermore, until the discovery by the present inventor, it was not predictable that MutS could be immobilized and still retain its DNA binding properties. It is well known that proteins undergo varying degrees of denaturation and may loose over 95% of their binding activity after immobilization by various methods, in particular, passive adsorption (Butler et al., supra, Butler, J. E. et al., *J. Immunol. Meth.* 150:77–90 (1992)). Additionally, as stated above, the order of binding of reactants is not trivial. Thus, the binding of a MBP (e.g., MutS) to DNA to yield a MutS-DNA complex, which then binds to a solid support such as nitrocellulose (NC) yielding MutS-DNA-NC, is not equivalent to the binding of MutS to NC to yield immobilized MutS-NC which then binds to DNA in solution to yield DNA-MutS-NC. As noted above, MutS does not interact in solution directly with the next protein in the physiological mismatch repair pathway, MutL; however, once MutS has bound DNA, the complex then binds to MutL (Grilley et al., *J. Biol. Chem.* 264:1000–1004 (1989)). This further supports the notion that order of binding is important in MutS interactions.

Further evidence that binding in solution of a DNA binding protein to DNA is not predictive of binding in immobilized form comes from studies performed by the present inventor showing that the DNA-binding protein recA from *E. coli* (which is not a mismatch binding protein) lost its ability to bind DNA after immobilization on nitrocellulose. This finding further supports the unexpected nature of the present invention.

A significant reason for the advantage of the present methods over prior art methods resides in the fact that when the MBP is immobilized, a heteroduplex containing a mispairing of the type recognized by the MBP is not only bound to the MBP but is also better retained on that immobilized protein. This allows more vigorous removal of unbound nucleotide fragments thereby lowering the background and enhancing the specificity and sensitivity of the assay remarkably. While not wishing to be bound to any particular theory, the present inventor proposes that in performing its physiological role, the MBP binds loosely to a double stranded region of DNA, and moves along the strands seeking areas of mispairing. This loose binding ability, which can be considered analogous to mere "binding" in vitro, accounts for background levels of binding of MBP to perfectly matched DNA in a binding assay. This background problem has prevented successful development and commercialization of mutation detection assays based on MBP binding prior to the present invention. When a MBP acting in vivo encounters a recognized mismatch or mispairing, it binds more tightly and recruits additional proteins which catalyze the excision and repair processes to correct the error. This tighter binding could be considered analogous to "binding plus retention" in vitro which is a hallmark of immobilized MutS as compared to MutS in solution. Such retentive binding in vivo is associated with the binding to the MutS-DNA complex of MutL which further stabilizes the interaction and leads to repair.

DETECTION OF HETEROZYGOSITY OR POLYMORPHISM

A mutation never exists as a mismatched base pair once DNA has replicated following the original mutational event. Rather, the mutated base will exist in the DNA in vivo in the form of a "matched" (albeit mutant) base pair. The existence of this mutation may be revealed as a mismatch using the methods disclosed herein. For such detection it is necessary to denature and anneal DNA to obtain a detectable mismatch.

The types of mutations that can be detected by the present methods include both homozygous and heterozygous mutations. Heterozygosity really means nothing other than the presence on one of a pair of homologous chromosomes of a DNA sequence difference. Depending upon the context, such a sequence difference is commonly referred to as a mutation ("heterozygous mutation") or as an alternative "allele" for a given genetic locus. By definition, heterozygosity only exists in DNA of a diploid organism.

However, the present methods are not limited to testing heterozygous or diploid organisms, because any detectable sequence difference among a population of DNA molecules in a sample (i.e., a difference that, under assay conditions, will produce a mismatched or mispaired heteroduplex bound by the MBP) can be screened for, or detected, using the present methods. In other words, the principle underlying the detection of homozygous mutations by the present methods is applicable to viral or bacterial DNA sequences or other non-diploid DNA species.

While it is important that the test DNA used in the present method comprises sequences of all four DNA strands from one or more pairs of chromosomes of a diploid organism, it is not necessary that DNA from the entire chromosome be included in the assay. That is, fragments of DNA much shorter than a chromosome can be tested for the presence of a heterozygous mutation using the present method as long as, for the region containing the mutation (or heterozygosity), nucleic acid sequences representing the sequence of both strands of both chromosomes is present in the assay.

It is also important to note that the present method does not require a double stranded DNA preparation be used to initiate the assay. Thus, for example, a conventional double stranded diploid test DNA preparation may be heated or otherwise denatured into single strands, maintained in this denatured state for a prolonged period and shipped in this single stranded form to a testing laboratory which utilizes the present methods. The testing laboratory then carries out the assays described herein using as its "test DNA" this single stranded (rather than a conventional double stranded) preparation. This assay is operable and will yield the same results as if the testing laboratory had used as its "test DNA" a conventional double stranded DNA preparation from cells of a diploid organism. This example illustrates that the present methods can be practiced successfully without a strict requirement for a double stranded DNA preparation in the assay itself; several embodiments of this invention provide the necessary second DNA strand for creation and detection of DNA mismatches and mispairings.

In the case of heterozygosity, the mismatch which is detected (and is created during the assay) occurs between two strands of DNA from the same individual (test DNA from the homologous chromosomes). However, the present methods are also capable of detecting "population heterozygosity," wherein a "variant" nucleotide sequence can exist at a level well below the 50% common for a heterozygous allele in a diploid cell. Thus, the present methods allow detection of such population heterozygosity in a population of eukaryotic somatic cells (preferably human), bacterial cells or viral particles where a difference recognizable by a MBP is present in only a small proportion of cells (or DNA molecules).

For detection of homozygous mutations, described below, the mismatch will occur in the pairing of the denatured DNA strands with a wild-type (or different) DNA strand added as part of the assay method. With the present methods, no a priori choice between these two possibilities must be made in selecting a test DNA to be analyzed. The methods described herein are operable with any DNA containing a mutation, either heterozygous or homozygous.

The method of the present invention is capable of detecting a mutation of the type described herein (or heterozygosity or polymorphism), even if one or several of the eight possible mismatches are not detectable. The present inventor as well as others have failed to detect C//C mismatches in a number of their experimental determinations because $E.\ coli$ MutS binds less well to C//C as compared to other mismatches. Note however, in Example A, below, the C//C mismatch could be detected using the present method. Yet even when binding to C//C is poorly detectable (or undetectable) in a given test on a given day or under a given condition, the present methods nevertheless enable detection of a mutation in which the DNA of one pair of strands produces a C//C mismatch during the assay. This is because the complementary pair of DNA strands will yield a G//G mismatch which gives a strong signal using the present method. Therefore, even if a given MBP, such as a MutS homologue from another bacterial species or from a eukaryotic species, does not bind detectably to all eight possible mismatches, this MBP can nevertheless detect all mutations when used according to the present methods.

To detect heterozygosity or polymorphism in DNA from a diploid organism, test DNA is preferably prepared by denaturing and annealing amplified DNA from a diploid organism. The test DNA is prepared with labeled primers, annealed and added to a well or other reaction vessel which contains immobilized MBP already bound to mismatched oligonucleotides. Alternatively, test DNA can be mixed with mismatched oligonucleotides and the mixture added to a well or other vessel containing immobilized MBP.

A spectrophotometric reading is made at the wavelength appropriate for quantitative detection of the test DNA. After an incubation period suitable to allow either (1) binding of the test DNA to the immobilized MBP or (2) displacement of the mismatched oligonucleotide from the immobilized MBP, the DNA solution is removed, the well washed, and a spectrophotometric reading made at the wavelength appropriate for quantitative detection of the bound mismatched oligonucleotide.

The ratio of the reading for test DNA to the reading for the mismatched oligonucleotide will be vastly different for mismatch-containing and mismatch-free test DNA over a wide range of DNA concentrations. Standard curves are prepared using known quantities of DNA to allow characterization of test DNA as homozygous or heterozygous without having to quantitate the test DNA prior to the assay. Thus, a single DNA sample is sufficient to determine heterozygosity and, for example, a single 96-well microplate will allow the testing of at least about 80 different DNA samples.

DETECTION OF HOMOZYGOUS MUTATIONS

To detect a homozygous mutation from wild-type, known wild-type DNA must be combined with the test DNA sample before, or at the time of, denaturing and annealing. Only test DNA containing a mutation (heterozygous or homozygous) will form a mismatch-containing heteroduplex with this added wild-type DNA. Such a heteroduplex will compete, for example, with the detectable (e.g., biotin-labeled) mismatch-containing oligonucleotide for binding to immobilized MBP. One skilled in the art will appreciate that this method will detect equally well a "mutation" from mutant to wild-type (i.e., a reverse mutation). In fact, the "mutant" and "wild-type" nomenclature is simply a convention of convenience. The presence of two nucleotide sequences which result, following denaturation and re-annealing, in a mismatch or mispairing recognized by the immobilized MBP is detectable using the present methods.

The method of the present invention can be used with (a) only the mismatched oligonucleotide labeled or (b) only the test DNA labeled. When the mismatched oligonucleotides are labeled, the test is a competitive assay, based on competition of the labeled oligonucleotide heteroduplex with several different concentrations of test DNA. The competing oligonucleotide may either be mixed with the test DNA in solution or may be pre-bound to the MBP. The resulting curve (with concentration expressed as moles of duplex molecules) is compared with a standard curve obtained with a mismatched standard and a perfectly matched standard.

When the test DNA is labeled, the test preferably involves measuring the extent of binding to the MBP at several concentrations below saturation and comparison of the resulting curve with standard curves for a mismatched standard and a perfectly matched standard.

The test DNA which is examined for the presence of a mutation is preferably mammalian DNA, more preferably human DNA However, the present methods may also be used with DNA obtained from any non-mammalian species, including both eukaryotic and prokaryotic DNA.

The present methods are particularly useful for screening for the absence of a mutation. If a nucleic acid sample tests negative in the present methods, it can be safely concluded that the sample contains no variant DNA which will form a mismatch with the wild-type sequence (or a known sequence which is added to the assay).

The present methods using immobilized MBP may also be used to screen for specific known mutations, although these methods must be followed by sequencing to verify the identity of the specific mutation. For such screening methods, the mutation must have a known sequence compared to the wild type sequence. Mutations detectable using the present methods are ones which result from a nucleotide substitution, a deletion or the addition of 14 nucleotides which produce heteroduplexes when the DNA is annealed with wild-type sequences. The mutations which may be screened are those which result, during the assay, in creation of mispaired heteroduplexes of the types recognized and bound by the MBP or functional derivative of the invention.

Thus, a preferred MBP (even if not strictly a MutS homologue as defined herein) for the present invention is one which recognizes the specific types of mispairings. A preferred MBP is characterized by its ability to bind duplexes containing mispaired or unpaired bases, to the significant exclusion of single stranded polynucleotides or perfectly matched duplexes (see above). Also included in the scope of the present invention are MBPs which recognize a different array of mismatches or mispairings than does *E. coli* MutS. As long as the nature of the mismatches or mispairings recognized by the protein are characterized, the protein can be used in the presently disclosed methods to detect mutations, heterozygosity and polymorphisms defined by the range of heteroduplex structures recognized by the MBP protein. One skilled in the art will readily appreciate which MBPs can be used to identify which types of mismatches or mispairings or unpaired bases in the methods disclosed herein without undue experimentation.

PURIFICATION OF AMPLIFIED DNA SAMPLES

One of the most revolutionary and widely used technologies currently employed in modern molecular biology is the process of polymerase chain reaction (PCR), which amplifies DNA sequences from starting amounts so minute as to be nearly undetectable. For reviews of PCR, see: Mullis, K. B., 1986, *Cold Spring Harbor Symp. Quant. Biol.* 51:263–273; Saiki, R. K. et al., 1985, *Bio/Technology* 3:1008–1012; and Mullis, K. B. et al, 1987, *Meth. Enzymol.* 155:335–350. In addition, because PCR can amplify specific sequences, it allows the purification of specific sequences, basically in a single step, from genomic DNA PCR is an essential component of virtually all studies of the human genome, is a central component of gene identification and cloning, is increasingly used in the diagnosis of genetic and infectious diseases and is widely used in forensics.

However, for some applications, in particular, gene cloning and mutation detection, PCR suffers from an inherent tendency of the polymerases to make mistakes by inserting incorrect, non-complementary bases during synthesis. Although the fidelity of in vivo DNA replication, including mismatch repair, is such that only one incorrect base is inserted for every $10^{10}$ bases replicated, polymerases used in PCR can have error rates as high as one incorrect base for every $10^4$ bases replicated. This high an error rate can mean that a significant fraction of the amplified molecules will not be identical in sequence with the starting material.

The present methods include using an immobilized MBP to remove a major proportion of error-containing sequences and minority sequences from PCR amplified material, which results in relative (and possibly complete) purification of the amplified. DNA. Those errors that are detected and removed are those which result from a nucleotide substitution, a nucleotide deletion or the addition of up to about 4 nucleotides. For example, if a DNA segment is amplified through 20 rounds of replication (a common amount of amplification), a significant fraction of the molecules generated may contain one or more incorrect bases. In cloning experiments, this greatly increases the risk of cloning a nucleotide sequence different from the starting sequence.

In mutation detection assays involving denaturation and annealing of a PCR-amplified sample, incorrect bases inserted during PCR may be scored as if they were mutations in the original sample. Thus, for accurate mutation detection it is necessary to eliminate all DNA molecules with sequence alterations introduced by PCR copy errors. The method described here accomplishes this purification in a simple and straightforward manner.

Immobilized MBP is used to purify amplified DNA samples. MBP is immobilized by binding to solid phase supports, preferably nitrocellulose filters, sepharose beads or magnetic beads. The filters or beads are treated, if necessary, to prevent the binding of double-stranded DNA. The amplified DNA sample is denatured, by heating, and allowed to reanneal. Given the random nature of PCR mistakes, virtually all incorrect bases will be found in mismatched base pairs after annealing.

The immobilized MBP is added to the sample and the solution mixed by gentle shaking. The immobilized MBP, and any bound mismatch-containing DNA, is removed, for example, by removing the filter, by centrifuging or allowing the beads to settle out of solution or by removing the beads magnetically, depending on the nature of the solid support used. In a preferred embodiment, the DNA solution is removed by vacuum filtration through solid phase filters such as nitrocellulose, to which the MBP is immobilized. The DNA duplexes left behind in solution are precisely matched duplexes.

In yet another embodiment of the present invention, amplified error-containing DNA may be removed from a PCR sample using soluble MBP. As above, the amplified DNA sample is denatured, by heating, and allowed to reanneal, leading to a state wherein incorrect bases are found in mismatched base pairs after annealing. This amplified reannealed material is mixed with an excess of about 5–100-fold of soluble MBP which is allowed to bind to mismatched heteroduplexes. The DNA-MBP complex is then allowed to adhere to a solid phase, such as a filter, preferably a nitrocellulose filter. Only mismatch-containing DNA bound to the MBP will bind to the filter. The now immobilized complex of MBP and mismatch-containing DNA is removed, for example, by removing the filter or by other means described above or well-known in the art. The DNA duplexes left behind in solution are precisely matched duplexes. This latter approach, while having lower apparent specificity than the method utilizing immobilized MBP, may offer advantages of greater capacity for bulk preparations.

In addition to purifying amplified DNA samples by removing molecules containing errors introduced during amplification, purification using an immobilized MBP is used to enrich for majority sequences during examination of samples of diverged, repeated DNA sequences, such as of immunoglobulin genes.

To remove completely a minority species from a DNA sample amplified from a mixed population of DNA (with respect to sequence), it may be necessary to perform more than one round of purification, as described herein, which may entail more than one round of amplification.

It is noteworthy that the present method can be used to purify sequences from both homozygous and heterozygous amplified sequences, since half of the parental sequences in a heterozygous sample will anneal to the complementary strand of the same parental heritage and thus form a molecule without mismatches. In other words, when the starting material is heterozygous DNA, half of the annealed molecules will be removed from the sample because they contain a mismatch due to differences in the starting sequences. However, half of the annealed molecules will not contain such mismatches and so will be removed from the sample only if they contain mismatches which were created as a result of errors during amplification. In any event, mutation detection assays will require a second round of denaturing and annealing.

While the present methods are particularly well-suited to remove error-containing sequences from PCR amplified DNA, the same methods can be used to remove sequences containing errors introduced during any type of DNA synthesis, such as normal DNA replication occurring in vivo. Because of the nature of the assay and of MBP recognition of mismatches/mispairings, any DNA containing an error leading to formation of a recognized mismatch can be removed. The DNA must not necessarily be "amplified" as the term is commonly used to describe DNA which has been subjected to PCR or similar amplification in vitro, or phage or plasmid DNA which can be considered to have been amplified in vivo.

ALLELE IDENTIFICATION IN MULTI-ALLELIC SYSTEMS

As more alleles of disease-causing genes are identified, and in the quest to develop a polymorphism map of the human genome, it is becoming increasingly important to be able to identify particular alleles of a given gene. Immobilized MBPs provide a simple and straightforward means of allele identification.

In principle, heterozygosity at a given locus wherein the two alleles differ by a single base pair (or small insertion or deletion) is no different than a "heterozygous mutation." The existence of two different alleles in the DNA of a single diploid subject can be detected by the claimed methods after denaturation and annealing, without the need of an additional wild-type polynucleotide strand. The methods disclosed herein can detect the presence of a sequence alteration (leading to a single base mismatch or mispairing in the assay, as above) which exists in the form of an allele or a variant for a genetic region that is polymorphic in a species (i.e., has more than one variant form) or, in other words, is part of a multi-allelic system. For detection by $E.\ coli$ MutS or homologue thereof, the allele or polymorphic variant must differ from the wild-type sequence, or from any "known sequence" for that particular genetic region, by a single base substitution or an addition or deletion of up to four bases. If a different MBP with a different mispairing specificity than MutS is used, then a different range of sequence differences leading to mismatches/mispairings will be detectable, as would readily be appreciated by one skilled in the art.

The present methods permit screening a test DNA sample for the presence of a specific known sequence in a selected region of an allele, with the understanding that, in those rare instances when a previously unknown allele which has a yet unknown sequence in the same selected region is present, a false positive result could be obtained. The known sequence, above, is characterized as differing from other known sequences in the same selected region of other known alleles of this multi-allelic system by a nucleotide substitution or a deletion or addition of up to 4 nucleotides recognized by the MBP. The unknown sequence above which could give rise to a false positive result is characterized in that it differs from the known sequence such that when the unknown sequence is annealed to the probe below), the resulting heteroduplex is not bound by the immobilized MBP used in the assay (i.e., lacks a detectable mismatch or mispairing).

In such a screening method, a detectably labeled oligonucleotide DNA probe is used. This probe is characterized in that it (i) is perfectly complementary to the known sequence of the selected region of the specific allele, and (ii) forms detectable heteroduplexes (containing a single base mismatch or one to four unpaired bases) when annealed with any other known sequences in the same selected region of other known alleles of this multi-allelic system.

Such a probe is mixed with excess test DNA, which preferably has been amplified, under conditions of denaturation followed by annealing such that, after denaturing and annealing, every copy of the probe is in a DNA homoduplex or heteroduplex. This duplex-containing mixture is then allowed to bind to an excess of immobilized MBP such as E. coli MutS protein under conditions in which heteroduplexes formed above bind to th immobilized protein. The immobilized protein to which these heteroduplexes are bound is removed from the test DNA. The presence of detectable (probe) label in the mixture from which heteroduplexes have been removed by the immobilized MBP indicates the presence in the test DNA of either (a) the specific known sequence in the selected region of the allele, or (b) the unknown sequence, both as characterized above.

As is evident from the foregoing, for allele identification (in contrast to heterozygous mutation detection), added probe sequences are required in the present methods. A unique, labeled oligonucleotide probe can be prepared for a selected region of each allele of a given gene, such that the probe is perfectly complementary to the region of only one allele and forms one or more detectable mismatches or mispairings when paired with any other allele. As above, the probe is mixed with an excess of (amplified) test DNA such that, after denaturing and annealing, every copy of the probe will be found in duplex. The process can then be repeated with probes representing every allele in the multiallelic system. Removal of heteroduplexes (mismatched DNA) from the mixture can be accomplished using any of a number of means, including:

(1) mixing the with immobilized MBP on a support that can be removed from the suspension by centrifugation;

(2) passing through a micro-column of immobilized MBP on an appropriate column support; or (3) passing through a filter support containing immobilized MBP.

In yet another embodiment utilizing a soluble MBP, the annealed DNA mixture as above is (4) mixed with soluble MBP, which is then allowed to bind to a solid phase support such as a nitrocellulose filter, as described above for removal of error containing DNA following PCR amplification.

As stated above in connection with purification of amplified DNA, this embodiment may provide enhanced capacity at the expense of lower specificity compared to the immobilized MBP method.

In the above allele-identification or screening methods, the immobilized MBP (or soluble MBP, as the case may be) must be in excess such that all mismatch-containing DNA is bound and retained. The supernatant, column flow through or filtrate is analyzed for the presence of label. Label will be detected only in those cases where the probe is perfectly complementary to the sequence of an allele represented in the test DNA.

In order to be certain that no single-stranded probe sequences are present, it may be necessary, or at least desirable, to include some single-stranded DNA binding component on the support for the immobilized MBP. This system works equally well for homozygous or heterozygous conditions.

SPECIFIC ALLELE IDENTIFICATION (DIPLOID DNA)

Hereditary mutations in humans (and other species) can be detected using an immobilized MBP method as described herein. Both heterozygous and homozygous mutations are detected. DNA for such tests can be obtained from a blood sample or tissue biopsy or, for fetal diagnostics, from amniotic cells, trophoblasts or circulating embryonal cells.

The detection of germ line mutations is of considerable importance for preventive medicine and gene therapy.

For this test, PCR primers specific for the fragment containing the mutation are selected. One of the primers is labeled at the 5' end with a detectable label. The primers must be highly specific, and PCR conditions are optimized such that amplification of a known homozygote (wild type or mutant) gives a low background signal in the assay.

A specific allele identification test for detecting a mutation is described in FIG. 15. The fragment amplified for the initial assay is preferably cloned into a plasmid to allow preparation of probes by PCR amplification with minimal risk of mispriming producing non-probe sequences. The probes may be prepared by PCR amplification from the plasmid with at least one labeled primer. If both primers are labeled, both strands of the probe will be labeled, which will allow direct detection of both heteroduplexes formed by pairing of the mutant and wild type alleles If desirable, for example, to decrease background or facilitate discrimination between wild type and mutant, probes can be prepared with only one strand labeled such that only one heteroduplex (and, therefore, only one mismatch) of the test/probe annealing will be labeled. The sample DNA is amplified with unlabeled primers, probe is added such that test DNA is in excess, the mixture is denatured and annealed, and the annealed mixture is exposed to immobilized MBP. Probes may be prepared from both wild type and mutant sequences. A positive signal in the test indicates that the test DNA contains sequences different from the probe. Absence of a signal indicates that the test DNA is of the same sequence as the probe and is homozygous. Heterozygotes will give a positive signal with both mutant and wild type probes. Positive signals are also generated with both probes if the test sample contains a heretofore undiscovered mutation or polymorphism.

Such a method is used to characterize sheep for susceptibility to scrapie (related to Creutzfeld-Jacob disease in humans). In some breeds of sheep, a single mutation appears to confer resistance to scrapie. The mutation in codon 171 of the prion protein gene involves a switch from glutamine (Q) to arginine (R). Thus R/R and Q/R sheep appear to be resistant to scrapie, whereas Q/Q sheep appear to be susceptible. A sample result is described in Example XIII (and FIG. 16).

To distinguish heterozygotes of the known mutation from heterozygotes or homozygotes of a previously unknown mutation, the Magnetic Mismatch Binding Bead ($MB_2B_2$™) assay is used (see below, Example XII and FIG. 15). This assay permits acquisition of quantitative data (e.g., FIG. 14). The test involves comparing probe/test mixtures with probe/known mixtures. For example, if the probe of wild type sequence is mixed with an excess of test DNA from a heterozygote, the signal obtained should be about ½ the signal obtained if the test DNA were from a homozygous mutant. Similarly, if the probe of mutant sequence is mixed with an excess of test DNA from a heterozygote [wild type×known mutant], the signal should be about ½ the signal obtained if the test DNA were from a heterozygote involving an unknown mutant, since in the latter case, the mutant probe forms mismatches with both genotypes in the sample. Thus, the $M_2B_2$™ assay serves as a screen for unknown mutations.

DETECTION AND CHARACTERIZATION OF INFECTIOUS AGENTS (HAPLOID DNA)

The immobilized MBP-based method of the present invention permits detection and characterization of an infectious agent with only a single set of primers and a set of strain-specific probes which need differ from one another by only a single base pair. Immobilized MBPs have the advantage, compared to known prior art methods, of greatly enhanced discrimination between mismatch-containing and perfectly paired DNA, as described above. Immobilized MBPs can detect mismatch-containing DNA, even when it represents less than 1% of the total DNA in the assay and even below 0.1% (FIG. 14). These properties make immobilized MBP assays ideally suited to the detection of infectious agents. The idea behind the assay is to amplify DNA, preferably by PCR, with primers specific to a particular region of the agents nucleic acid. The primers must be specific for the particular infectious agent, although the primers need not distinguish strains of the agent. It is preferable if the primers amplify DNA from all pathogenic strains of a given organism. The specificity of the primers must be such that amplification produces a product only if genomic DNA of the organism in question is present in the sample. For example, if the assay is to detect the presence of HIV DNA obtained from a human tissue sample, the primers selected must be specific for HIV DNA and not produce a product from human DNA or from DNA of another infectious agent. The presence of the infectious agent is detected by at least two different methods.

A. Mismatched Primer

If one primer selected to amplify a specific fragment of an infectious agent's nucleic acid contains a single base sequence difference from the "normal" target sequence (the sequence to which the primer is intended to be perfectly complementary), the primer will form a mismatch when annealed to that "normal" target sequence. The resulting amplification products will be of two types: (a) those having the normal sequence which were synthesized using the normal sequence primer and the normal template and (b) those of a "mutant" sequence which were synthesized either using the mismatched primer or using the normal sequence primer on a template containing the mismatched primer. In practice it is preferred to use a mixture of normal and "mutant" sequences for one of the primers and only the perfectly matched sequence for the other primer in order to keep the numbers of normal and "mutant" sequences in the final product as nearly equal as possible. One of the primers contains a 5' label (e.g., biotin).

The amplification products are denatured and annealed and exposed to immobilized MBP as described herein. If DNA of the infectious agent is present in the test sample, a positive signal will result. If samples are taken at several points during PCR amplification, it is possible, by comparison to a standard curve, to estimate the number of molecules of target DNA present in the original sample.

B. Mismatched Probe

In this method, both primers are unlabeled and perfectly complementary to the specific sequences they are intended to amplify. Following amplification, the products are denatured and annealed in the presence of a labeled probe sequence which is designed to form a detectable (preferably G//T) mismatch with all known pathogenic variants of the organism to be detected. The probe is detectably labeled (e.g., 5'-biotin) and of sufficient length such that it anneals uniquely to the amplified fragment. The annealed sample is exposed to immobilized MBP as described herein. A positive signal indicates the presence of the agent in question. If samples are taken at several points during PCR amplification and annealed to a constant amount of probe DNA, it is possible by comparison to a standard curve to estimate the number of molecules of target DNA present in the original sample.

These methods of infectious agent detection bear a similarity to detection by specific PCR amplification (as they involve specific PCR amplification). However, they offer at least two significant advantages: (1) detection does not require gel electrophoresis and is therefore amenable to automation and high throughput applications, and (2) it becomes possible to estimate, directly and simply, the concentration of infectious organisms in a biological sample.

C. Characterization of Infectious Agents

An important strength of immobilized MBP methods disclosed herein is their ability to characterize infectious agents rapidly, simply and unambiguously. For example, infectious agents can be characterized with respect to their strain or their antibiotic resistance pattern. Characterization involves the steps of:

1. Amplifying a Specific Region of a Given Infectious Agent

Primer selection has the same requirements as described above, i.e., primers must amplify only the specific region of the agent in question and not any portion of the host genome or of genomes of other infectious agents potentially present in the test sample. It is important that the region to be amplified is selected to be specific for the particular infectious agent and is different in each of the strains or variants to be distinguished. Primers are unlabeled.

2. Annealing the Amplification Products to an Array of Probes, Each of Which is Specific for a Particular Strain or Variant of the Infectious Agent The probes must be the same length as the amplification product. Each probe must be perfectly complementary to one, and only one, strain or variant of the infectious agent and be detectably labeled (e.g. 5'-biotin). The probes themselves can be amplification products produced by PCR amplification of known sequences using the same primers (except for the presence of label) as used in the characterization assay.

3. Exposing Each of the Annealed Probe/PCR Product Mixtures to Immobilized MBP

Positive signals indicate that the probe formed one or more detectable mismatches with the amplification product. A negative signal indicates identity of probe and amplification product sequences and identifies the strain or variant of the infectious agent.

If the assay is performed with a nitrocellulose support in a 48 well slot blot apparatus and if detection is by means of chemiluminescence, as described herein, the result will be a series of dark slots with a single negative for each test sample. Positive slots provide controls for: (1) the presence of the infectious agent, (2) successful amplification and (3) successful annealing of probes. If all the slots are negative, either the infectious agent is absent, amplification failed, or annealing failed. Alternative controls readily confirm that amplification and annealing could have occurred successfully. An example of such a control is the addition of known sequences to test samples before amplification, such that the absence of positive results indicates that the infectious agent was not present in the original sample. Thus, in a single step, the assay can both determine if an infectious agent is present in a sample and characterize it with respect to strain or variant. If positive signals are obtained with all probes, either there is more than one strain of the infectious agent in the sample or the strain or variant of infectious agent in the sample must be a heretofore uncharacterized strain or variant (differing by one or more mismatches or mispairings recognized by the MBP). Thus, the present method also provides a means for screening for new variants of infectious agents such as, for example, new reverse transcriptase mutants of HIV, influenza virus variants, Plasmodium variants, or antibiotic resistant bacterial mutants.

DETECTION OF FUNCTIONAL MISMATCH BINDING PROTEINS IN CELL EXTRACTS OR PURIFIED PROTEIN PREPARATIONS

This method is based upon the immobilized mismatch binding protein mutation detection assay as described above. In particular, this assay is based upon the ability of an MBP in solution to interfere with the immobilized MBP assay.

The assay is generally performed as described below. A biological sample being tested for the presence of a functional MBP, preferably a cell or tissue extract or a protein-containing fraction from such an extract, is mixed with a double-stranded oligonucleotide containing a mismatch which is readily bound by an immobilized MBP. Thus, in a preferred embodiment, the immobilized MBP is E. coli MutS and the oligonucleotide contains a well-recognized single base pair mismatch, preferably G//T, (or one to four unpaired bases) any of which mismatches or mispairings is recognized by E. coli MutS. The oligonucleotide may be in the form of a mismatch-containing heteroduplex or denatured single strands which under assay conditions will anneal to form the mismatch-containing heteroduplex.

An example of such a heteroduplex (see Examples, below) is a synthetic 30mer oligonucleotide with a G//T mismatch at position 15 and a 5' biotin label. Particularly when a cell extract is used, the method may require a mixture of (1) labeled mismatch-containing oligonucleotide and (2) an excess of unlabeled double-stranded DNA lacking mismatches which serves to bind any non-specific DNA binding proteins which may be present in the extract thereby minimizing their interference with the activity of specific MBP in the sample.

After an appropriate incubation, the mixture is contacted with an immobilized MBP, preferably E. coli MutS, as described in detail above. If the protein preparation or extract contains MBPs, the signal in the immobilized mismatch binding protein assay will be reduced. In other words, the MBPs in the sample will have bound to any labeled heteroduplex DNA, thus preventing such heteroduplex DNA from binding to the immobilized MBP.

To ensure that reduction in binding is due to the presence of an MBP in the sample and not to destruction of the of the labeled oligonucleotide probe by any nucleases in the sample, a separate aliquot of the above mixture is heated to inactivate MBPs, for example at 70° C. for 10 minutes, or under alternate conditions of time and temperature known to the skilled artisan. The immobilized mismatch binding assay is repeated on this heat-treated sample. If the absent or reduced mismatch binding signal is recovered, following such treatment, this result indicates that the activity dented was DNA binding activity and not an artifact of nuclease digestion of the oligonucleotide.

The assay preferably includes a control which comprises a known MSH2-deficient extract.

Using this method, a sample of cells from a subject suspected of being susceptible to a form of cancer associated with a deficiency in mismatch repair, for example hereditary non-polyposis colon cancer, can be tested in a simple and economic manner. This approach lends itself to an inexpensive screening procedure for large numbers of samples.

MISMATCH DETECTION BY AMPLIFICATION OF DNA BOUND TO IMMOBILIZED MISMATCH BINDING PROTEIN

The preset invention is also directed to a method for detecting mismatches in which test DNA, preferably a sample of genomic DNA, is first subjected to digestion with restriction enzymes, denatured and reannealed and then allowed to bind to an immobilized MBP. If the sequence of interest containing the mutation is present, it becomes amplified "in situ".

This method depends upon prior knowledge of the sequence of interest so that appropriate restriction as can be identified and an appropriate probe designed which will result in an MBP-detectable mismatch.

Test DNA, typically genomic DNA, with known sequence in a specific region, is subjected to restriction enzyme digestion such that the region of interest and a primer site or sites (for PCR or other DNA polymerase-based synthesis) are contained in a single restriction fragment. This digested DNA is then denatured and annealed, as described above. For a heterozygous mutation, the mismatch will be created upon reannealing with a DNA sequence from the homologous chromosome. For homozygous mutations, DNA having the wild-type sequence for the site of interest must be added prior to or during the annealing step.

The annealed DNA is then exposed to immobilized MBP, preferably MutS, and mismatch-containing heteroduplexes are allowed to bind. Unbound DNA is removed by washing. A primer or primers for DNA synthesis are added to the bound DNA and the DNA is amplified. Preferably, this is done using PCR. However, if the restriction fragment being tested is of sufficient size, a single round of DNA replication using, for example, E. coli DNA polymerase or T4 polymerase, may suffice to generate a detectable signal.

The product of the amplification may be detected by any of a number of methods. For example, for maximal simplicity, incorporation of a label such as a radiolabeled nucleotide into TCA-precipitable DNA can be measured. Alternatively, detection may be accomplished using known gel electrophoresis methods to identify a characteristic oligonucleotide band. If there was no mutation in the test sample, there would be no incorporation of label into DNA because no DNA will have been bound to the MBP. Similarly, recovery of a PCR product is indicative of the presence of a mismatch in the annealed fragments, and therefore a mutation in the sample DNA. If no exogenous (probe) DNA was added to the assay, then a positive result indicates a heterozygous state of the test DNA. A positive result in the case where wild-type DNA had been added to the sample is indicative of a homozygous or heterozygous mutation in the sampled restriction fragment.

A two step assay may also be performed in which the first step is carried out without added wild-type DNA. A heterozygous mutation would yield a positive signal whereas either a homozygous mutation or no mutation would give a negative result. A second step is then carried out in which wild-type DNA is added. A positive signal here indicates a homozygous mutation whereas a negative result indicates the absence of any mutation.

It is noteworthy that any sequence based DNA amplification or synthesis method, including PCR and the ligase chain reaction method, will allow use of this method. Importantly, the error proneness of the polymerase in PCR is of no consequence in the present method as the amplification is merely being used to generate a detectable signal (measurable amount of DNA). The expected frequency of errors in the PCR product would not affect the measurement.

Selection of the restriction enzyme or enzymes used in this method depends upon several factors. First, the requisite restriction site must flank the sequence to be tested. Two non-identical restriction sites, recognized by different restriction endonucleases, may be selected. However, the enzyme(s) must not cut between the site of interest (bearing the mutation, heterozygosity or polymorphism) and the primer site or sites. The restriction sites should be selected such to yield a fragment of appropriate length. Such a fragment is preferably as short as possible to avoid possibility of having distal from the site of interest (a) a chance polymorphic sequence or (b) internal secondary structure which could act as a mismatch or a mispairing. On the other hand, the fragment should be of sufficient length to: (1) hybridize with the requisite specificity to form a heteroduplex bindable to an immobilized MBP; (2) include the site of interest and one or two primer sites; (3) be detectable following a convenient amount of amplification. Thus, such a fragment can be of any length but is preferably from about 50–500 bases, more preferably from about 100 to 300 bases. The primer site(s) of the test fragment can either be separate from, or overlap with, the sequence of interest.

The foregoing method is especially well-suited for detection of mutations in specific regions of DNA and is very amenable to automation whether employing PCR or ligase chain reaction, or only a single round of DNA synthesis to generate a detectable product.

DETECTION OF TRIPLET REPEATS

The underlying cause of the large expansions of trinucleotide repeats may be the formation of a secondary structure in the template strand, in particular, a hairpin structure with a repeating block of G:C base pairs flanking a mismatch (A//A, T//T, C//C or G//G). Such a structure might be expected to block DNA synthesis. If so, polymerase idling (i.e., back and forth movement) may occur at the site of the hairpin resulting in the production of a single stranded loop (FIG. 8). If DNA synthesis can then resume across, or through, the hairpin, the result could be a large expansion of the repeat block in a single S-phase.

The differential ability of complementary heteroduplexes (CGG vs. CCG and CTG vs. CAG) to form secondary structures which bind to immobilized MBPs such as MutS is described in the Examples below and provides a basis for development of a rapid diagnostic test. Such a test detects the presence of expanded or contracted blocks of triplet repeats and the diseases associated with such repeats. The diagnostic test is used to identify individuals with (a) a mutation and who are at risk for developing a disease associated with triplet repeats before the onset of disease symptoms (e.g., prenatally) and (b) asymptomatic carriers of premutational alleles. The term "premutational" as used herein (see: Caskey et al., 1992, supra) refers to normal symptom free individuals who nevertheless transmit a disease condition, such as fragile X syndrome, and who have numbers of triplet repeats outside the normal range (e.g., 52–200 CGG repeats in fragile X syndrome). Fragile X syndrome is the first human disorder in which premutation DNA sequences in the parent predict risk of disease in the progeny. The present method therefore provides a means for screening parents for risk of transmitting fragile X syndrome (or other triplet repeat-associated disorders). As described herein, the assay is simple, reliable and does not require sequencing or the use or interpretation of any gel patterns.

The method is based on two discoveries by the present inventor. First, only one triplet repeat sequence of the complementary

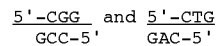

sequences is able to form partially double stranded secondary structures detectable by binding to an MBP. Second an immobilized MBP selectively binds duplexes such as those shown above (5'CGG$_n$ and 5'CTG$_n$ duplexes) but not duplexes of the forms 5'CCG$_n$ and 5'CAG$_n$ due to the formation of the double stranded secondary structure.

The assay method involves the following steps:

1. Test DNA is prepared and may be amplified if desired. If amplification is by PCR, the primers are selected to flank the triplet repeat region.
2. Test DNA (or amplified test DNA) is mixed with a labeled (e.g., biotinylated) single stranded probe complementary to the CGG- or CTG-containing strand in the triplet repeat region of the test DNA The probe includes the flanking region sequences. In one embodiment, the number of triplet repeats in the probe is equal to the number of triplet repeats in the largest triplet repeat block considered to be normal. Repeat numbers fall into three classes: (1) normal, (2) premutational and (3) disease.
3. The mixture is denatured, preferably by heating or with pH treatment and allowed to reanneal.
4. The annealed DNA is exposed to immobilized MBP, preferably E. coli MutS, and the binding is visualized, preferably by the Enhanced Chemiluminescence method described herein. Alternatively, binding may be visualized using the in situ preamplification method described above.

If the test DNA contains only normal DNA, that is, DNA having a triplet repeat number equal to or lower than the triplet repeat number in the probe, there will either be no unpaired bases or the unpaired bases will be from the probe DNA. Because, the MBP does not recognize unpaired bases (single stranded region) of the CCG or CAG repeats found in the probe, the MBP will not bind to the annealed duplexes.

If, however, the test DNA has a block of triplet repeat sequences longer than that in the probe, the unpaired bases (CGG or CTG) of the test DNA, which do form secondary structure containing mismatches (i.e., heteroduplex secondary structure) will be recognized by the MBP.

By adjusting the number of triplet repeats in the probe, the assay can be designed to detect either a premutational state or a disease state. This is schematically illustrated in FIG. 11. Thus, in one embodiment, the repeat block in the probe is shorter than the shortest block to be detected. This probe preferably contains 5° CCG repeats, or, read in the opposite polarity, 5'CGG repeats in the test DNA. Alternatively, this probe can contain 5° CAG repeats for detecting 5'GTC repeats in the test DNA. When the repeat block in the test DNA is shorter than in the probe, a looping out of probe DNA occurs, which is not recognized by the MBP. However, when the repeat block of the test DNA is longer than the probe, a looping out of test DNA occurs, which due to the 5'GGC repeat unit, forms a mismatch containing secondary structure which is recognized by the MBP.

In another embodiment, the repeat block in the probe is longer than the longest block to be detected. This probe preferably contains CGG repeats for detecting CCG (or, read in the opposite direction, GCC) repeats in the test DNA. Alternatively, this probe can contain CTG repeats for detecting CAG repeats in the test DNA. Thus, when the test block is shorter than the probe block, looping out occurs in the probe DNA which, due to the CGG repeat unit, forms a mismatch containing secondary structure which is recognized by the MBP. If the test DNA repeat block is longer than the probe block, the looping out occurs in the test DNA, which, due to the CCG unit sequence, does not form a structure that is recognized by the MBP.

As is readily apparent to those skilled in the art, this method for detecting repeat blocks is not limited to triplet repeats, but can be utilized with any microsatellite repeat number by appropriate design of the probe block sequence and length.

DETECTION AND ENRICHMENT OF MINORITY SEQUENCES

The methods described above are applicable to the detection of minority sequences which differ from the majority sequence by a single mismatch, multiple non-contiguous single mismatches, or by one or more non-contiguous additions or deletions each of about one to about four bases. Detection of such minority sequences is particularly useful in the screening of tissue samples in which only a small number of cells may have undergone mutations. One example of this is screening cells or tissues such as the "fringes" of a tumor for the presence of mutations associated with cancer, e.g., p53 mutations. Another is in screening for contaminating sequences in DNA preparations such as those used for gene therapy.

Detection of minority sequences preferably begins with amplification of DNA, such as by PCR, using primers specific to the region of interest. Such primers will amplify both wild-type and mutant (minority) nucleotide sequences. The amplified DNA product is subjected to denaturation and annealing such that minority sequences will, almost invariably, be annealed to wild-type sequences (because they are so much more prevalent), resulting in mismatch-containing heteroduplexes. Such heteroduplexes are detected using the methods described herein. A positive signal indicates the presence of minority (mutant, contaminating sequences). At least at low levels of contamination, the signal appears to be proportional to extent of contamination. Example XII shows results of a study exemplifying this approach.

Enrichment of a minority sequence preferably also begins with amplification of the DNA using primers specific to the region of interest. Such primers will amplify both wild type and mutant (minority) sequences. As above, the amplification product is denatured and annealed such that minority sequences will, almost invariably, be annealed to wild type sequences, thus forming mismatch-containing heteroduplexes. Such denatured and annealed amplification product is mixed with Magnetic Mismatch Binding Beads ($M_2B_2$™) (see below) or any MBP as described herein immobilized to any appropriate solid support or carrier.

The immobilized MBP to which mismatch-containing DNA has bound is washed thoroughly to remove unbound material. DNA remaining bound to immobilized MBP is reamplified either directly from the immobilized MBP or following removal of the DNA from the immobilized MBP by heat, high salt, etc. The newly amplified product is an enriched source (potentially 50%) of minority sequence. Such a preparation used for sequencing, cloning, etc.

MISMATCH DETECTION USING MutS IMMOBILIZED ON MAGNETIC BEADS

A preferred protocol using MutS immobilized on magnetic beads is performed as described below. See FIG. 17 for schematic illustration.

1. DNA

The key to successful mismatch or mutation detection using MutS immobilized on magnetic beads (Genecheck's Magnetic Mismatch Binding Beads $M_2B_2$™) is to provide the $M_2B_2$™ with good DNA. $M_2B_2$™ is so sensitive that 1% contamination of a DNA sample with labeled mismatch containing DNA (or even labeled single stranded DNA capable of forming secondary structure with mismatches) will give a positive signal. If DNA to be examined is a PCR product, the quality of the product must be very high. PCR products of sufficient quality for sequencing applications are often not of sufficient quality for $M_2B_2$™ assays. This is because sequencing examines each position in a fragment independently, whereas $M_2B_26$ examines the entire fragment. Therefore, a 0.1% error rate at each position of a 100 mer will give insignificant background signals in a sequencing reaction but will give a strong positive signal in an $M_2B_2$™ assay, since approximately 10% of the molecules will contain at least one error capable of forming a mismatch with the majority sequence.

$M_2B_2$™ works with DNA from any source, including synthetic oligonucleotides and amplified genomic DNA. Fragment of 100 to 300 base pairs appear to work best, although shorter (down to 30 base pairs) and longer (70 to 400 base pairs) fragments may also be used.

The following describes a preferred, though by no means exclusive, protocol for carrying out this embodiment of the invention.

2. Buffer and Sample Preparation $M_2B_2$™ wash buffer is prepared by diluting 10× $M_2B_2$™ Wash Buffer 1:10 with distilled water and filtering the diluted buffer through a 0.2 µm filter. Each test sample requires 1 ml of diluted $M_2B_2$™ wash buffer. (This is the same as the "reaction buffer" described herein). DNA dilution buffer is PBS+% BSA 400 µl is required for each test sample. After BSA is dissolved in PBS, the solution should be filtered through a 0.45 µm filter. Test DNA is end labeled. A biotin label is preferred, and is detected with a streptavidin-conjugated horseradish peroxidase (HRP) and a chromogenic HRP substrate. The amount of test DNA which is optimal for the $M_2B_2$™ assay is determined empirically and depends on the length and nature of the fragment being examined. Generally DNA amounts in the 1–100 ng range give good positive signals and good discrimination between mismatched and nonmismatched DNA. It is advisable to test a number of DNA concentrations when first working with a particular DNA fragment. DNA should be diluted to 190 µl in DNA dilution buffer.

3. DNA Binding

All steps are performed at room temperature. $M_2B_2$™ are resuspended by vortexing. Ten µl of $M_2B_2$™ are added to each test sample. Some applications may require more $M_2B_2$™. Tubes are agitated individually by "flicking" with fingers. Creation of air bubbles during agitation appears to increase mixing. Tubes are incubated for at least 30 min with agitation (shaking, rocking or rotating). Longer incubation times (up to about 3 hrs.) may increase signal. Following incubation, tubes are centrifuged briefly. A magnetic field is applied and the supernatant removed.

4. Washing $M_2B_2$™ wash buffer (200 µl) is added to each tube and the $M_2B_2$™ moved through the buffer by rotating the tubes in front of the magnet. The magnet is applied and the supernatant removed. These steps are repeated.

5. Detection of DNA

The method of DNA detection employed depends on the label employed and on the preferences of the individual performing the test. When using biotin labeling, the following detection protocol is applied: Add 200 µl 0.25 µg/ml Streptavidin/HRP in PBS+1% BSA to each sample and resuspend $M_2B_2$™ by flicking. Incubate for 20 min with agitation (shaking, rocking or rotating), centrifuge briefly and apply a magnet. Remove the supernatant, add 200 µl $M_2B_2$™ wash buffer to each sample and invert tubes and shake forcefully followed by a brief centrifugation. Add a chromogenic substrate and proceed according to manufacturer's instructions.

A typical binding curve using the above method, showing absorbance as a function of DNA concentration, appears in FIG. 13.

KITS

The present invention is also directed to a kit or reagent system useful for practicing the methods described herein. Such a kit will contain a reagent combination comprising the essential elements required to conduct an assay according to the methods disclosed herein. The reagent system is presented in a commercially packaged form, as a composition or admixture where the compatibility of the reagents will allow, in a test device configuration, or more typically as a test kit, i.e., a packaged combination of one or more containers, devices, or the like holding the necessary reagents, and usually including written instructions for the performance of assays. The kit of the present invention may include any configurations and compositions for performing the various assay formats described herein.

In all cases, the reagent system will comprise (1) an immobilizable or immobilized MBP or functional derivative, preferably MutS, and (2) additional reagents useful in carrying out the assay. The kit may optionally contain labeled mismatch-containing oligonucleotides. For detecting a particular mutation, a kit may also contain labeled primers for carrying out a PCR. For detecting triplet repeats, the kit will contain the appropriate repeat-containing probes. A kit according to the present invention can additionally include ancillary chemicals such as the buffers and components of the solution in which binding of nucleic acid duplexes to the immobilized MBP takes place.

A kit useful for the method which detects mismatches by amplification of DNA bound to an immobilized MBP preferably contains restriction enzymes for preparing the test DNA fragments, wild-type genomic DNA fragments containing the sequence of interest, one or two primers for amplification of bound fragments, and positive and negative control double stranded DNA fragments either containing or lacking a detectable mismatch. Also included in such a kit would be the immobilized or immobilizable MBP and other reagents for the assay as described above.

Having now generally described the invention, the same will be more readily understood through reference to the following examples which are provided by way of illustration, and are not intended to be limiting of the present invention, unless specified.

EXAMPLE I

Binding of Mismatch-Containing DNA by Immobilized Mismatch Binding Protein

A. Materials and Methods

1. Preparation of Immobilized MBP

A nitrocellulose sheet (0.451 m, Schleicher & Schull) was wet with reaction buffer (20 mM Tris pH 7.6, 0.01 mM EDTA, 5 mM $MgCl_2$, 0.1 mM DTT) and placed in a dot blot apparatus (Bio-Rad).

Purified MBP, *E. coli* MutS, at a concentration of 0.5 µg/10 µl reaction buffer was spotted on the nitrocellulose paper in each well. The wells were incubated at room temperature, and the remaining liquid was pulled through with vacuum. Each well was washed twice with 100 µl reaction buffer by adding the solution to the well and then pouring it out. After the second wash, the remaining solution was pulled through the vacuum.

2. Blocking

The nitrocellulose filter was blocked with bovine serum albumin (BSA) to prevent the binding of other proteins or nucleic acids. Reaction buffer (200 µl) containing 1% (w/v) BSA was added to each well. After 1 hour at room temperature, the solution was poured out and each well washed with 2×100 µl reaction buffer by adding the solution to the well and then pouring it out. After the second wash, the remaining liquid was pulled through with vacuum.

3. Oligonucleotides

The sequence of the oligonucleotides used in these studies was taken from the 30 base region surrounding the site of the sickle cell mutation in the human J-globin gene. The mismatch is at the site of the sickle cell mutation, although the mutant sequence used to form the mismatch is not the sickle cell mutation (the actual sickle cell mutation is an A:T→T:A transversion. Biotinylated oligonucleotides were biotinylated on the 5' end of the mutant strand. Biotinylation is accomplished during synthesis by adding a biotin-modified nucleotide to the 5' end of the oligonucleotides.

```
No Mismatch:

Mutant GCACCTGACTCCTGGGGAGAAGTCTGCCGT  [SEQ ID NO:1]

Mutant CGTGGACTGAGGACCCCTCTTCAGACGGCA  [SEQ ID NO:2]

G:T Mismatch:

Mutant GCACCTGACTCCTGGGGAGAAGTCTGCCGT  [SEQ ID NO:1]

Wild-  CGTGGACTGAGGACTCCTCTTCAGACGGCA  [SEQ ID NO:3]
type
```

4. Binding DNA

Biotinylated oligonucleotides, in 20 µl reaction buffer containing 1% BSA, were added to each well. After 30 minutes at room temperature, remaining liquid was poured out. Each well was washed with 5×100 µl reaction buffer by adding the solution to the well and then pouring it out. After the fifth wash, the remaining solution was pulled through by vacuum.

5. Binding Streptavidin-conjugated Horse Radish Peroxidase (HRP)

The presence of biotin was detected by its binding of Streptavidin. A 100 µl volume of Streptavidin-conjugated HRP (Pierce Chemicals) at a concentration of 50 mg/ml in reaction buffer+1% BSA was added to each well. After 2 hours at room temperature the solution was poured out and each well washed with 5×100 µl reaction buffer by adding the solution and then pouring it out. After the fifth wash, the remaining solution was pulled through with vacuum.

6. Enhanced ChemiLuminescene® (ECL) Development

The nitrocellulose sheet was removed from dot blot apparatus and washed 3 times in a petri dish with 10 ml reaction buffer. Five ml ECL development solution (Amersham) was poured over the nitrocellulose. The substrate for HRP in this reagent is a chemiluminescent compound. After 1 minute, the solution was removed. The nitrocellulose was blotted dry and placed between 2 clear plastic sheets. The nitrocellulose thus protected was exposed to X-ray film in the dark for varying periods of time. In the experiments reported here, the exposure time was 1 minute.

7. Competition

In competition studies, the DNA binding was as described above, except that a constant amount of biotinylated mismatch-containing oligonucleotide (5 ng) was mixed with varying amounts of unlabeled DNA, with or without a mismatch, and added to the wells.

B. Results

1. Specific Binding of Mismatch-Containing DNA by Immobilized MBP

Figure 1:
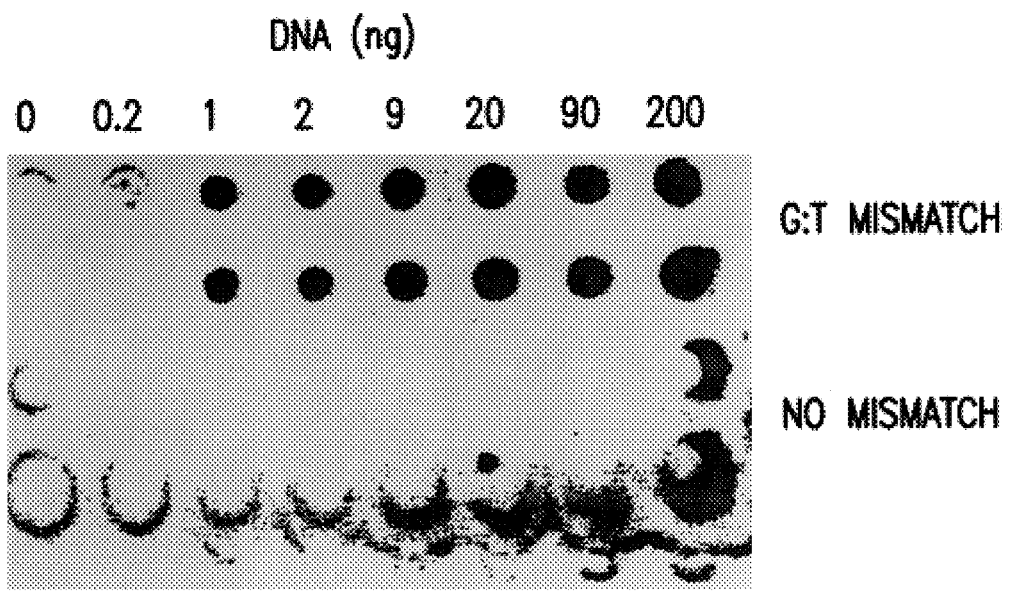
FIG. 1 shows the results of a direct assay of mismatches using nitrocellulose-bound MutS. Increasing amounts of biotinylated mismatch-containing DNA (upper 2 lines) or mismatch-free DNA (lower 2 lines) were added to the reaction mixtures.

FIG. 1 shows the results (in duplicate) of adding increasing amounts of biotinylated mismatch-containing DNA (upper 2 lines) or mismatch-free DNA (lower 2 lines).

The immobilized MBP can detect as little as 0.2 ng of mismatch-containing 30-mer, whereas no detectable binding of mismatch-free 30-mer was observed even with 200 ng of DNA. (The lines around the lower spots were artifacts of incomplete washing.)

2. Competition Assay

Figure 2:
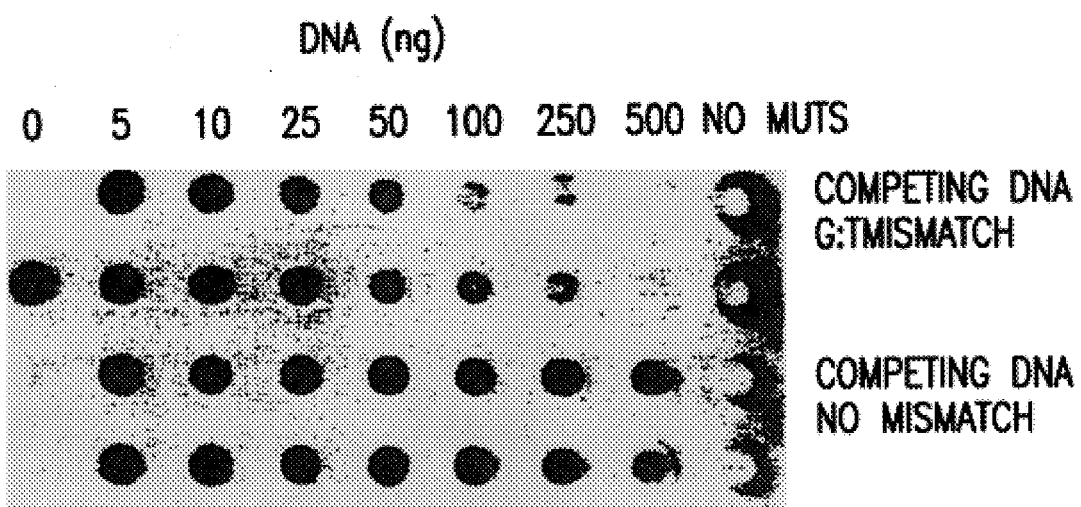
FIG. 2 shows the results of a competition assay of mismatched duplexes using nitrocellulose-bound MutS protein. Increasing amounts of unlabeled mismatch-containing 30-mer (upper 2 lines) or mismatch-free 30-mer (lower 2 lines) were added to 5 ng biotinylated mismatch-containing 30-mer. The far right column on the figure represents wells which contained no MutS.

FIG. 2 shows the results (in duplicate) of adding increasing amounts of unlabeled mismatch-containing 30-mer (upper 2 lines) or mismatch-free 30-mer (lower 2 lines) to 5 ng biotinylated mismatch-containing 30-mer. Although competition was clearly visible with 50 ng of mismatch-containing DNA, the mismatch-free DNA did not compete until 500 ng, if at all. The far right column on the figure contains no MBP.

The results indicate that, at least with the 30mers used above, immobilized MBP discriminates between mismatch-containing and perfectly paired DNA with an efficiency of at least three orders of magnitude. Similar results have been obtained using 54mers with a sequence derived from the V3 loop of HIV. Therefore, even if the discrimination decreases as the amount of perfectly paired duplex increases, the discrimination efficiency when using 300mers, considered to be the maximum useful length for polymorphism studies of the human genome, should be on the order of a factor of 100.

EXAMPLE II

Detection of Various Single Base Mismatches Unpaired Bases

This study was performed to ascertain the ability of immobilized *E. coli* MutS protein to bind to and detect various single base mismatches and one to four unpaired bases.

These studies utilized synthetic oligonucleotides (eight 30mers and one each of a 31mer, a 32mer a 33mer and a 34mer) listed below:

| | SEQ ID NO: |
|---|---|
| 5' GCACCTGACTCCTG<u>G</u>GGAGAAGTCTGCCGT 3' | 1 |
| 3' CGTGGACTGAGGAC<u>C</u>CCTCTTCAGACGGCA 5' | 2 |
| 3' CGTGGACTGAGGAC<u>T</u>CCTCTTCAGACGGCA 5' | 3 |
| 5' GCACCTGACTCCTG<u>T</u>GGAGAAGTCTGCCGT 3' | 4 |
| 3' CGTGGACTGAGGAC<u>G</u>CCTCTTCAGACGGCA 5' | 5 |
| 5' GCACCTGACTCCTG<u>C</u>GGAGAAGTCTGCCGT 3' | 6 |
| 5' GCACCTGACTCCTG<u>A</u>GGAGAAGTCTGCCGT 3' | 7 |
| 3' CGTGGACTGAGGAC<u>A</u>CCTCTTCAGACGGCA 5' | 8 |
| 3' CGTGGACTGAGGACC<u>C</u>CCTCTTCAGACGGCA 5' | 9 |
| 3' CGTGGACTGAGGACC<u>CA</u>CCTCTTCAGACGGCA 5' | 10 |
| 3' CGTGGACTGAGGACC<u>AG</u>CCTCTTCAGACGGCA 5' | 11 |
| 3' CGTGGACTGAGGACC<u>CAGG</u>CCTCTTCAGACGGCA 5' | 12 |

The nucleotide or nucleotides participating in the mismatches (or unpaired bases) are underscored above. The homoduplex and heteroduplexes containing the mismatches or unpaired bases, prepared from the above oligonucleotides are indicated below.

```
Homoduplex

5' Biotin- GCACCTGACTCCTGGGGAGAAGTCTGCCGT -3'     (SEQ ID NO: 1)

3'- CGTGGACTGAGGACCCCTCTTCAGACGGCA 5'     (SEQ ID NO: 2)

G//T Mismatch

5' Biotin- GCACCTGACTCCTGGGGAGAAGTCTGCCGT -3'     (SEQ ID NO: 1)

3'- CGTGGACTGAGGACTCCTCTTCAGACGGCA -5'    (SEQ ID NO: 3)

T//G Mismatch

5' Biotin- GCACCTGACTCCTGTGGAGAAGTCTGCCGT -3'     (SEQ ID NO: 4)

3'- CGTGGACTGAGGACGCCTCTTCAGACGGCA -5'    (SEQ ID NO: 5)
```

-continued

C//T Mismatch

5' Biotin- GCACCTGACTCCTGC GGAGAAGTCTGCCGT -3'    (SEQ ID NO: 6)
       3'- CGTGGACTGAGGACT CCTCTTCAGACGGCA -5'    (SEQ ID NO: 3)

G//G Mismatch

5' Biotin- GCACCTGACTCCTGG GGAGAAGTCTGCCGT -3'    (SEQ ID NO: 1)
       3'- CGTGGACTGAGGACG CCTCTTCAGACGGCA -5'    (SEQ ID NO: 2)

A//G Mismatch

5' Biotin- GCACCTGACTCCTGA GGAGAAGTCTGCCGT -3'    (SEQ ID NO: 7)
       3'- CGTGGACTGAGGACG CCTCTTCAGACGGCA -5'    (SEQ ID NO: 5)

G//A Mismatch

5' Biotin- yGCACCTGACTCCTGG GGAGAAGTCTGCCGT -3'
        3'-CGTGGACTGAGGACA CCTCTTCAGACGGCA -5'    (SEQ ID NO: 8)

A//C Mismatch

5' Biotin- GCACCTGACTCCTGA GGAGAAGTCTGCCGT -3'    (SEQ ID NO: 7)
       3'- CGTGGACTGAGGACC CCTCTTCAGACGGCA -5'    (SEQ ID NO: 2)

A//A Mismatch

5' Biotin- GCACCTGACTCCTGA GGAGAAGTCTGCCGT -3'    (SEQ ID NO: 7)
       3'- CGTGGACTGAGGACA CCTCTTCAGACGGCA -5'    (SEQ ID NO: 8)

T//T Mismatch

5' Biotin- GCACCTGACTCCTGT GGAGAAGTCTGCCGT -3'    (SEQ ID NO: 4)
       3'- CGTGGACTGAGGACT CCTCTTCAGACGGCA -5'    (SEQ ID NO: 3)

C//C Mismatch

5' Biotin- GCACCTGACTCCTGGC GAGAAGTCTGCCGT -3'
       3'- CGTGGACTGAGGACCC CTCTTCAGACGGCA -5'    (SEQ ID NO: 2)

Unpaired C

5' Biotin- GCACCTGACTCCTGG GGAGAAGTCTGCCGT -3'
       3'- CGTGGACTGAGGACCC CTCTTCAGACGGCA -5'    (SEQ ID NO: 9)

Unpaired CA

5' Biotin- GCACCTGACTCCTGG  GGAGAAGTCTGCCGT -3'
       3'- CGTGGACTGAGGACCCA CCTCTTCAGACGGCA -5'   (SEQ ID NO: 10)

Unpaired CAG

5' Biotin- GCACCTGACTCCTGG    GGAGAAGTCTGCCGT -3'
       3'- CGTGGACTGAGGACCCAG CCTCTTCAGACGGCA -5'  (SEQ ID NO: 11)

Unpaired CAGG

5' Biotin- GCACCTGACTCCTGG     GGAGAAGTCTGCCGT -3'
       3'- CGTGGACTGAGGACCCAGG CCTCTTCAGACGGCA -5' (SEQ ID NO: 12)

As described above, these sequences were taken from, or are closely related to, the human J-globin gene in the region of the mutation responsible for sickle-cell anemia. The mismatches are at position 15 and the unpaired bases are between positions 15 and 16 of the oligonucleotides.

Biotin Labeling of DNA

Those oligonucleotides beginning with the sequence 5'GCA were prepared with a 5' biotin label to allow detection by the Enhanced Chemiluminescence (ECL) detection system and were annealed to unlabeled oligonucleotides such that only one strand of each duplex was labeled.

Some oligonucleotides were labeled with both biotin and $^{32}$P, which did not affect either biotin or radioactivity detection.

The duplexes were used in a mismatch detection assay using immobilized mismatch binding protein (MutS), essentially as described above. The following is a description of the assay:

Oligonucleotides were diluted in TNE buffer (10 mM Tris HCl, pH 8.0; 0.01M NaCl, 1 mM EDTA). Biotin labeled or radiolabeled oligonucleotides were diluted to 10 ng/µl and unlabeled oligonucleotides to 100 ng/µl. Equal volumes of diluted oligonucleotides were mixed and annealed at 70° C. for 10 min, followed by incubation at room temperature for 30 min, followed by quenching on ice. The preparations were stored at -20° C. where appropriate. The unlabeled oligonucleotides were in 10-fold excess to assure that all biotin-labeled strands were in duplexes.

Immobilization of MutS on Solid Supports and Biotin Detection Assay (a) Nitrocellulose A nitrocellulose sheet (0.45 µm, Schleicher and Schull, BA85) was pre-wet by floating in reaction buffer (20 mM Tris HCl, pH 7.6; 5 MgCl$_2$, 0.1 mM DTT, 0.01 mM EDTA). MutS (500 ng/well) in reaction buffer was bound to the nitrocellulose in a 48 well slot blotting apparatus (Hoefer Scientific Instruments) over 3 sheets of blotting paper (Schleicher and Schull GB002). Reaction buffer alone was added to "no MutS" wells. After 20 min. at room temperature, nitrocellulose was blocked with 200 µl/well of 3% horse radish peroxidase (HRP)-free bovine serum albumin (BSA). After 1 hour, excess blocking solution was pulled through with vacuum and DNA (1 ng and 10 ng) was added in 20 µl reaction buffer containing 3% BSA. After 30 min. at room temperature, wells were washed 5 times with 100 µl reaction buffer. The wash fluids were decanted rather than pulled through with vacuum.

(b) Detection of Biotin

The presence of biotin-labeled DNA bound on the nitrocellulose sheet was detected by visualizing the binding of streptavidin to biotin. 100 µl streptavidin-conjugated HRP (0.05 µg/ml in reaction buffer+BSA) was added to each well. After 20 min. at room temperature, any remaining solution was decanted and the wells washed 5 times with 100 µl reaction buffer as above.

The nitrocellulose sheet was removed from the apparatus and washed 4 times for 1 min with 500 ml reaction buffer in a small tray. Nitrocellulose was blotted dry and immersed in 10 ml of ECL development solution (Amersham).

Results

Figure 3A:
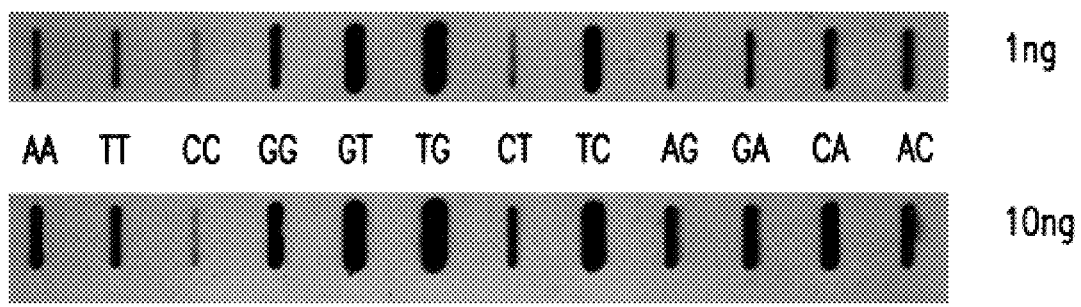
FIGS. 3A and 3B show the binding of immobilized *E. coli* MutS to various duplexes containing mismatched and unpaired bases. Mismatch containing heteroduplexes are labeled GT, GG, etc., with the two concentrations of DNA tested (1 or 10 ng) indicated. Heteroduplexes containing unpaired bases were labeled as follows: [1]: Unpaired C; [2]: Unpaired CA; [3]: Unpaired CAG; [4] Unpaired CAGG. Asterisks next to the mismatched base pair or the number label for the unpaired bases indicates "No MutS" controls.
Figure 3B:
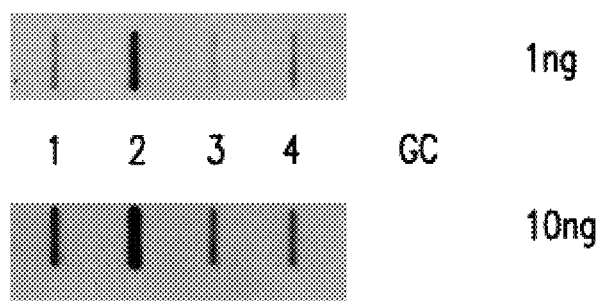

The results are presented in FIGS. 3A and 3B. Mismatch containing heteroduplexes are labeled GT, GG, etc., with the two concentrations of DNA tested (1 or long) indicated. Heteroduplexes containing various numbers of unpaired bases were labeled with the number of unpaired bases as follows: [1]: Unpaired C; [2]: Unpaired CA; [3]: Unpaired CAG; [4] Unpaired CAGG.

All mismatches except C//C were detected under these conditions. Heteroduplexes with 1–4 unpaired bases were detected, though heteroduplexes with 34 unpaired bases were not detected as well as 1–2 unpaired bases.

The fact that T//C mismatches were better detected than C//T mismatches suggested that the sequence of the neighboring bases on an individual strand may influence the extent of mismatch detection, at least in relatively short oligonucleotides such as those used here. However, G//T and T//G mismatches were equally well-detected, suggesting that well-detected mismatches are detected independent of strand orientation.

The failure to bind C//C mismatches does not diminish the utility of this method for mutation detection, since every wild-type/mutant pairing gives rise to two different mismatches, for example G//G-C//C, wherein G//G mismatches give strong signals.

These results indicate that immobilized mismatch binding protein assays, as disclosed in the instant patent application, detect all mutations due to a single base change. Thus, although the C//C mismatches were not bound by immobilized MutS, the corresponding G//G mismatch, which would of necessity occur in any mutant:wild type pairing that had a C//C mismatch, gave a strong signal. Therefore this method may be used to detect all mutations arising from a single base change as well as mutations arising from small (1–4 nucleotide) additions or deletions.

EXAMPLE III

Detection of Heterozygosity

The present methods were used to detect heterozygosity at a specific location in human genomic DNA. PCR amplification was performed on a portion of exon 3 of the human glucokinase gene extending from codon 98 (encoding glutamine) to the stop codon (Soffel et al., Proc. Natl. Acad. Sci. USA 89:7698–7702 (1992)). The wild-type double stranded sequence of 100 bases corresponding to exon 3 human glucokinase is as follows:

[SEQ ID NO:13]

5'- GCACTAACTTCAGGGTGATGCTGGTGAAGGTGGGAGAAGG

3'- CGTGATTGAAGTCCCACTACGACCACTTCCACCCTCTTCC

TGAGGAGGGG<u>CAG</u>TGGAGCGTGAAGACCAAACACCAGATG

ACTCCTCCCC<u>GTC</u>ACCTCGCACTTCTGGTTTGTGGTCTAC

ATGAGGTAGGGGCTCCTGCG - 3'

TACTCCATCCCCGAGGACGC - 5'

In the heterozygous DNA (see below), the C of the underlined CAG codon was mutated to T. The DNA sequences tested were PCR amplified from genomic DNA obtained from: (1) a known heterozygote at that position [labeled "Heterozygote", (2) a known homozygote at that position [labeled "Homozygote 1"] and (3) a presumed homozygote at that position [labeled "Homozygote 2"]. Test DNAs were denatured, by heating, allowed to reanneal and tested for the presence of mismatches (i.e., heterozygotes) by testing their binding in an immobilized mismatch binding protein assay according to the present invention, utilizing E. coli MutS.

PCR Amplification to Create 100mers

The templates used were:

(a) "HETEROZYGOTE"—DNA known to be heterozygous for a mutation (C:G to T:A) in glucokinase gene exon 3;

(b) "HOMOZYGOTE 1"—Human genomic DNA known to be homozygous at glucokinase gene exon 3;

(c) "HOMOZYGOTE 2"—Human genomic DNA, male, presumed homozygous at glucokinase gene exon 3 (commercially obtained from Sigma Chemical Co.)

The primers (obtained from Operon) were HPLC purified and had the following sequences, corresponding to the 5' termini of the two 100mer strands shown above:

Primer#1: 5'(biotin)-GCACTAACTTCAGGGTGA [SEQ ID NO:14]

Primer #2: 5'-GCGTCCTCGGGGATGGAGTA-3' [SEQ ID NO:15]

PCR Primer #1 contained biotin bound at the 5' end to allow detection in the ECL detection system described below. Primer #2 was radiolabeled with a 5'-$^{32}$P-phosphate to allow quantitation of the different amplification products after removal of unused primers.

The PCR reaction included: 10 mM Tris HCl pH 8.3; 50 mM KCl; 1.5 mM MgCl$_2$; 0.001% gelatin (w/v); 0.05 mM DATP; 0.05 mM dTTP; 0.05 mM dGTP; 0.05 mM dCTP; 0.11M primer #1; 0.0751M primer #2; 0.0251M $^{32}$P primer #2; 200 ng template DNA; and 2.5 units AmpliTaq DNA polymerase (Perkin-Elmer). Reaction volume was 1001 l. Amplification was carried out for 30 cycles in a Perkin-Elmer thermocycler by denaturing at 90° C. for 1 min., annealing at 55° C. for 1 min. and extension at 72° C. 2 min. Unused primers were removed by centrifugal dialysis using Centricon 30 (Amicon) microconcentrators according to manufacturers protocol. PCR products were quantitated by running equal amounts (measured as cpm of radioactivity) on non-denaturing 8% polyacrylamide gels, staining with ethidium bromide and comparing them to standard DNA.

PCR Amplification to Create 230mers

For the heterozygous 230mer, the template (DGK79) was human genomic DNA known to be heterozygous for a mutation (GCC to TCC, Gly to Ser, at codon 53) in exon 3 of the glucokinase gene (obtained from Dr. N. Cohen, CEPR, Paris, France. The corresponding homozygous template was human genomic DNA presumed to be homozygous in exon 3 of the glucokinase gene (obtained from Sigma Chemical Co.)

PCR amplification was performed using three different polymerase enzymes:

1. *Pyrococcus woesii* (PWO) polymerase (Boehringer-Mannheim).
2. *Thermococcus litoralis* polymerase (New England Biolabs) a. Vent (exo$^-$) or b. Vent (exo$^+$) included exonuclease The primers for the 230mers were:

Primer #1: 5'(biotin)-GAAGGTGATGAGACGGA [SEQ ID NO:16]

Primer #2: 5'-CCCAGGAGATTCTGTCTC  [SEQ ID NO:17]

PCR mixtures (100 μl) each contained: 20 mM Tris-HCl pH 8.8, 10 mM KCl, 2 mM MgSO$_4$, 10 mM (NH$_4$)$_2$SO$_4$, 0.1% Triton X-100, 0.25 mM dNTPs, 0.2 μM primer #1, 0.2 primer #2, 200 ng template DNA, 2 units DNA polymerase. 30 cycles were performed as follows: Denaturation: 1 min., 94° C. Annealing: 1 min., 3 cycles 64° C., 3 cycles 62° C., 3 cycles 60° C., 3 cycles 58° C., 3 cycles 56° C., 15 cycles 54° C. Extension was for 2 min. at 72° C. Primers were removed with QIA quick spin columns (Quigen). PCR products were eluted in 10 mM Tris-HCl pH 8.0 and were adjusted to 0.1M NaCl. The denaturation was done at 1000 for 2 min. Annealing was done at 55° C. for 60 min, 75° C. for 4min, 55° C. for 30 min, followed by cooling to room temperature.

Additional 30mer Controls

Positive and negative control DNA, also studied in Example II, above, comprised 30mer heteroduplexes with a G//T mismatch:

```
                                          (SEQ ID NO:1)
5' Biotin- GCACCTGACTCCTGGGGAGAAGTCTGCCGT -3'

(SEQ ID NO:3)
       3'- CGTGGACTGAGGACTCCTCTTCAGACGGCA -5'
``` and 30mer homoduplexes having a G:C in the same position.

```
                                          (SEQ ID NO:1)
5' Biotin- GCACCTGACTCCTGGGGAGAAGTCTGCCGT -3'

(SEQ ID NO:2)
       3'- CGTGGACTGAGGACCCCTCTTCAGACGGCA -5'
```

(b) The immobilized MutS Binding assays were performed as described above. DNA was denatured and annealed (in Perkin-Elmer thermocycler) according to the following schedule: 100° C. for 4 min; 50° C. for 1 hour; 75° C. for 4 min; 50° C. for 30 min, followed by cooling to room temperature. MutS was added to each well of a slot blot apparatus, DNA preparations were added and the wells washed as described. Streptavidin-HRP was added and allowed to bind to any biotin present on the nitrocellulose, and detected by the ECL assay, as above.

Results

The results binding of 100 mer DNA duplexes to immobilized MutS are shown in FIG. 4. The positive control was the G//T containing 30-mer heteroduplex. The negative control was the 30-mer homoduplex, as described above.

No binding of negative control was detected even at 10 ng of DNA, whereas the positive control was detected at 0.1 ng. The absence of binding without MutS indicates that all DNA binding observed was MutS-dependent. Binding of heterozygote nucleic acid to MutS was clearly visible at 0.6 ng. Homozygote binding (independent of the source of the DNA) was faintly detectable at 1.25 ng and was clearly detected at 2.5 ng. Thus, heterozygote DNA was detected as much as 5 times better than homozygote DNA in this assay. This is in contrast to the binding of MutS to the DNA in solution (see experiments described below). It was concluded from these and other results that the binding of mismatch containing DNA to immobilized MutS is markedly better than the binding to MutS in solution.

The binding of homozygote DNA at higher concentrations was considered to be the result of errors introduced during amplification by the Taq polymerase, a well-known phenomenon. Thus, such inappropriate binding still represented mismatch binding by the immobilized MutS.

The possibility that longer DNA fragments were bound by MutS regardless of the presence of mismatches is highly unlikely, because (a) the PCR products (100 base pairs) were only 3.3 times larger that the negative control DNA (30 base pairs) which did not bind, and (b) competition with a 100-fold excess of unlabeled undigested genomic DNA did not reduce "background" binding to the homozygote DNA. The results of binding of 230mer DNA duplexes to immobilized MutS are shown in FIGS. 5A, 5B, and 5C. 230mer heteroduplexes are designated "DGK79," whereas 230mer homoduplexes are designated "HOMO" in panels A and B. Panel C shows the positive control 30mer heteroduplex ("G//T") and the negative control 30mer homoduplex ("G:C").

The results indicate that heteroduplex molecules (having G//A and T//C mismatches) amplified by three different polymerase preparations (with or without exonuclease activity, bound to immobilized MutS with great specificity down to concentrations of 2.5 ng DNA. In contrast, only background binding of amplified homoduplexes was observed (at 20 ng DNA, possibly due in part to errors introduced during amplification. Binding of 30mer heteroduplex and homoduplex DNA to immobilized MutS was as expected. These results provide further evidence of the sensitivity of the present assay and show strong binding of DNA having G//T, G//A and T//C mismatches.

EXAMPLE IV

Mismatch Binding by MutS Immobilized on Other Supports

A. MutS Immobilized on Polyvinylidene Difluoride (PVDF)

Immobilization of MutS and assay of DNA binding was performed exactly as described above for nitrocellulose. The only change in the above protocol was the initial equilibration of the PVDF membrane. The membrane was slowly immersed in 100 ml ethanol and left for two minutes. The membrane was then washed five times with 100 ml distilled water. The membrane was floated on 100 ml reaction buffer and then immersed. The PVDF membrane was then equilibrated to the reaction buffer for 10 minutes prior to use.

The results are shown in FIG. 6. This study utilized the biotin label and the ECL assay as described in Examples I–III. Slots to which were bound 500 ng MutS could detect from 10 ng down to 16 pg of G//T containing 30mer DNA. G:C containing 30mers were not detected at (my concentration tested. Control slots having no MutS did not bind any DNA. The "no MutS" controls as well as the MutS-G:C combination showed halos surrounding the slots, in contrast to typical dark zones of reactivity in the slots, at the two or three higher concentrations. These halos are believed to be artifacts. However, even if there were binding of G:C detected at 2.5 ng DNA, the binding of the mismatched DNA is at least 128-fold greater.

It was concluded from this experiment that MutS immobilized on PVDF functions in accordance with the invention in binding mismatch containing DNA heteroduplexes.

B. MutS Immobilized on Nylon

Nylon filter was pre-wet with reaction buffer (as above). The slot blot apparatus was assembled as above. Reaction buffer, 100 µl/well was added and pulled through with vacuum. MutS was applied to each well (500 ng in 10 µl per well). "No MutS" controls contained 10 µl of reaction buffer. The filters were incubated for 15 min at room temperature and were then blocked as above. The apparatus was sealed with Parafilm.

This study utilized a $^{32}P$ label rather than biotin label and assayed bound radioactivity (by radioautography). $^{32}P$ labeling was achieved using a kinase reaction. The kinase reaction mix contained: 70 mM Tris HCl, pH 7.6; 10 mM $MgCl_2$; 5 mM DTT; 20 µCi $^{32}P$-ATP; 30 units T4 polynucleotide kinase; and 500 ng DNA (in the case of primer #2). The kinase reaction was performed in a 201 l reaction volume at 37° C. for 30 min. Kinase was inactivated by heating at 65–70° C. for 10–15 min. DNA was stored at –20° C.

$^{32}P$-labeled DNA was prepared in reaction buffer containing 3% BSA. Samples of 20 µl were pipetted into appropriate wells and incubated for 30 min. at room temperature. Wells were washed with 150 µl reaction buffer five times, with decanting, and the last wash was pulled through with vacuum. The filter was removed and washed with 50 ml reaction buffer 3 times. The filter was blotted dry, wrapped in Saran wrap. Radioautography was performed by exposing the filter to X-ray film overnight at –80° C. The film was then developed and the reaction zones visualized.

The results are shown in FIG. 7. Slots to which were bound 500 ng MutS could detect from 10 ng down to 0.1 ng of G//T containing 30mer DNA. G:C containing 30mers were undetected at all four concentrations tested (10, 1, 0.1 and 0.01 ng). Control slots having no MutS did not bind any DNA.

It was concluded from this experiment that MutS immobilized on nylon functions in accordance with the invention in binding mismatch-containing DNA heteroduplexes.

C. MutS Immobilized to Magnetic Beads

Dynabeads (Dynal M-280, tosyl activated) were resuspended by vortexing and 2 mg of beads were taken for the assay. The beads were washed twice with 400 µl phosphate buffered saline (PBS) (140 mM NaCl, 2.7 mM KCl, 10 mM $Na_2HPO_4$, $KH_2PO_4$, pH 7.4), and the wash fluid was aspirated by pipet. 250 µg of beads were taken for the "No MutS" control and were incubated with 50 µl PBS supplemented with 3% BSA (PBS-BSA). To the remaining beads was added 235 µg MutS (ratio of 25 µg MutS/mg beads). These mixtures were incubated overnight at room temperature with shaking. The supernatants were then removed and the beads washed with 700 µl PBS-BSA, with shaking, as follows: three times for 10 minutes, once for 30 min and overnight at 4° C. Between washes, beads were allowed to settle and the supernatant removed by aspiration.

Beads were resuspended at 250 µg/100 µl PBS-BSA and dispensed in 250 kg aliquots. The supernatant was removed, varying concentrations of DNA were added in 400 µl PBS-BSA and the mixtures incubated for 30 min. at room temperature with shaking. The DNA solution was removed and the beads were washed 3 times with 600 µl reaction buffer (see Example II, above). 0.05% HRP-conjugated streptavidin in reaction buffer was added in a volume of 400 µl per tube and incubated for 20 min. at room temperature with shaking. The streptavidin solution was removed, the beads washed 3 times with 600 µl reaction buffer and 200 µl of developer was added, comprising 2.5 ml citrate acetate (10 mM citric acid, 100 mM sodium acetate, pH 6.0), 26 µl tetramethylbenzidine and 4.25ml 3% $H_2O_2$. When color developed (3–15 min.), the reaction was stopped by adding 25 µl 2M sulfuric acid. Absorbance was read at a wavelength of 450 nm ($OD_{450}$).

TABLE I

Binding of 30mer Heterozygous (Het) and Homozygous (Homo) DNA to MutS Immobilized on Magnetic Beads
$OD_{450}$ (Absorbance Units)

| DNA (ng) | Homo | Het | Het (Net units)* |
|---|---|---|---|
| 1.6 | 0.005 | 0.021 | 0.017 |
| 3.12 | 0.003 | 0.013 | 0.009 |
| 6.25 | 0.005 | 0.018 | 0.015 |
| 12.5 | 0.003 | 0.040 | 0.036 |
| 25 | 0.004 | 0.060 | 0.056 |
| 50 | 0.002 | 0.107 | 0.103 |
| 100 | 0.005 | 0.101 | 0.097 |

*After subtraction of Background (0.004 units) which was the mean of the following two controls:
No DNA: 0.005   No MutS: 0.004 (using 100 ng Het DNA)

These results show a linear relationship between DNA concentration added to the immobilized MutS beads and the amount of DNA bound ($OD_{450}$) between 1.6 and 50 ng DNA, at which level DNA binding achieved a plateau. Homozygous DNA showed no binding whatsoever to MutS immobilized on the magnetic beads.

It was concluded that MutS immobilized on magnetic beads binds mismatch-containing DNA with high specificity.

EXAMPLE V

Comparison of Mismatch Binding by Immobilized and Soluble MutS

This study compared binding of a G//T-containing heteroduplex (30mer described above) to MutS immobilized on nitrocellulose and compared it to binding of the heteroduplex by MutS in solution. The duplexes were labeled with both biotin and $^{32}$P. The solution binding study measured radioactivity bound, whereas the immobilized MutS binding study measured biotin bound.

Oligonucleotides were labeled with both biotin and $^{32}$P, as described in the previous examples, which did not affect either biotin or radioactivity detection The binding of $^{32}$P-labeled heteroduplexes to MutS in solution was tested in a standard filter binding assay essentially as described by Jiricny, J. et al., *Nucl. Acids Res.* 16:7843–7853 (1988). The oligonucleotides were labeled as above and annealed with a 10-fold excess of unlabeled "complementary" oligonucleotides to yield a homoduplex and a heteroduplex containing a single G//T mismatch. For this assay, 500 ng of MutS in reaction buffer (20 µl) was incubated for 30 minutes at room temperature with the two types of duplexes. The mixture was spotted onto pre-wet nitrocellulose filters, which were then washed 5 times with 2 ml reaction buffer by vacuum filtration and dried at 80° C. for 15 minutes. Each filter was placed in 3 ml scintillation fluid and the radioactivity determined by scintillation counting. Background cpm (no MutS) were subtracted from the cpm bound by MutS. Means of duplicate or triplicate determinations are shown below.

The results of the binding to MutS in solution are shown in Table II, below.

TABLE II

| Mismatch | DNA (ng) | Net CPM bound | Exp/Control |
| --- | --- | --- | --- |
| Control (G:C) | 0.1 | 80 | |
| | 1.0 | 242 | |
| | 10.0 | 1403 | |
| Exp (G//T) | 0.1 | 142 | 1.8 |
| | 1.0 | 1252 | 5.2 |
| | 10.0 | 7236 | 5.2 |

These results show about a 5-fold increase in mismatch binding compared to homoduplex binding.

The results of binding of the identical DNA preparations to MutS immobilized on nitrocellulose are shown in FIG. 8. These are the same G//T and G:C pairings used above. Immobilized MutS detected binding of G//T heteroduplexes down to levels of 16 pg DNA. Control G:C homoduplexes appeared to bind only to 10 ng DNA over the "no MutS" background. These results indicate an increase of about 500-fold in mismatch binding compared to homoduplex binding. These results were highly unexpected in view of what was known from the prior art, particularly in view of the low ratios generally obtained with soluble MutS. Other experiments have given ratios as high as 1000 (see, for example, FIG. 1).

It was concluded from these studies that an immobilized mismatch binding protein is about two to three orders of magnitude more sensitive than the same protein in soluble form in a method for detecting nucleotide mismatches and thereby, for detecting mutations, heterozygosity, and allelic variants.

EXAMPLE VI

Removal of Mismatch Containing DNA from a PCR Amplified Sample

Two types of PCR products were examined. Both homozygous and heterozygous DNA 100mers (SEQ ID NO:13, supra) and 230mers were produced in PCR. For the heterozygous 230mer, the template (DGK79) was human genomic DNA known to be heterozygous for a mutation (GCC to TCC, Gly to Ser, at codon 53) in exon 2 of the glucokinase gene (obtained from Dr. N. Cohen, CEPH, Paris, France. The corresponding homozygous template was human genomic DNA presumed to be homozygous in exon 2 of the glucokinase gene (obtained from Sigma Chemical Co.)

PCR amplification was performed using "Vent" polymerase (exo$^+$) from *Thermococcus litoralis* (purchased from New England Biolabs). The primers for the 230mers were:

```
Primer #1:
5'(biotin)-   GAAGGTGATGAGACGGAT      [SEQ ID NO:16]

Primer #2:
5'-           CCCAGGAGATTCTGTCTC      [SEQ ID NO:17]
```

The primers for the 100 mers were SEQ ID NO: 14 and SEQ ID NO:15 (supra).

PCR mixtures (100 µl) each contained: 20 mM Tris-HCl pH 8.8, 10 mM KCl, 2 mM MgSO$_4$, 10 mM (NH$_4$)$_2$SO$_4$, 0.1% Triton X-100, 0.25 mM dNTPs, 0.2 µM primer #1, 0.2 µM primer #2, 200 ng template DNA, 2 units DNA polymerase. 30 cycles were performed as follows: Denaturation: 1 min., 94° C. Annealing: 1 min., 3 cycles 64° C., 3 cycles 62° C., 3 cycles 60° C., 3 cycles 58° C., 3 cycles 56° C., 15 cycles 54° C. Extension: 2 min., 72° C. Primers were removed with QIA quick spin columns (Quigen). PCR products were eluted in 10 mM Tris-HCl pH 8.0 and were adjusted to 0.1 M NaCl. The additional denaturation and reannealing was done under the following conditions: 100° C. for 4 min, 50° C. for 60 min, 75° C. for 4 min, 50° C. for 30 min and cooling in a block overnight to room temperature.

The cleanup procedure was carried out at room temperature. The reaction buffer described above (see Examples I and II) was used in the MutS immobilized binding assay described above.

The clean-up was performed by flowing DNA through MutS which had been immobilized on Millipore Immobilon P Multi-screen plates (MAIP N45). The plates had been prepared as follows:

1. Immobilon P plates were prepared according to manufacture's instructions.
2. 200 µl of a MutS solution (120 ng/µl) were added to wells and allowed to incubate for 5 min.
3. Fluid was pulled through by vacuum and collected in a standard 96 well plate.
4. The collected MutS solutions were reapplied twice more to the original wells as in step 3 for a total of 3 cycles of MutS binding to wells.
5. Wells were washed by applying and pulling through 3×200 µl reaction buffer, and the wash fluid was discarded.
6. 200 µl BSA blocking solution (1 µg/µl BSA, 200 µl/well) was added to wells, incubated 5 min and pulled through.
7. DNA (75 ng in 40 µl) was added and incubated for 60 min. with gentle shaking.
8. The solution was pulled through and collected ("first fraction"). 20 µl reaction buffer was added to each well, pulled through, and combined with the first fraction ("DNA Pool").
9. The DNA Pool of duplicate wells was combined to achieve sufficient quantity for detection. A PCR amplified DNA preparation (A) not subjected to the above clean-up procedure ("Pre-clean up") served as a control. An aliquot was removed for quantitation of DNA. The remaining material was divided into two groups. One aliquot was the "post cleanup" fraction (B). The other aliquot was subjected to denaturing and reannealing (fraction C).

10. DNA to be quantitated was measured using the DEAE/ethidium bromide method, against a DNA digest standard.

11. Equal quantities of Preparations A, B and C were tested in the immobilized MutS assay. The immobilized MutS was prepared and the assay performed essentially as described in Examples I and II, above.

The following results were obtained. Immobilized MutS removed a majority of mismatched DNA from both amplified heterozygous and amplified homozygous DNA samples. In the case of heterozygous DNA, denaturing and reannealing recovered signal equal to that of the DNA before cleanup. Little or no signal was recovered following denaturation and reannealing of homozygous DNA.

EXAMPLE VII

Detection of Functional Mismatch Binding Protein in Cell Extracts

Studies were done to evaluate the immobilized MBP assay for its utility in screening a cell extract for the presence of a MBP. This approach is based on the expectation that a biological fluid or cell extract containing a MBP would bind the appropriate heteroduplex in solution and prevent the heteroduplex from being recognized and bound by immobilized MutS.

1. Inhibition of Immobilized MutS Binding by Soluble MutS

Increasing amount of E. coli MutS (8–5000 ng) were mixed in solution with long of the heterozygous 30mer (Bio-Het) having a G//T mismatch

```
                                              (SEQ ID NO:1)
5' Biotin- GCACCTGACTCCTGGGGAGAAGTCTGCCGT -3'

(SEQ ID NO:3)
      3'- CGTGGACTGAGGACTCCTCTTCAGACGGCA -5'
``` and the mixture was incubated at room temperature with gentle shaking for 15 min. This mixture was then assayed for binding to immobilized MutS as described in Examples I and II.

The results (FIG. 9A = 9B, Panel B) indicate that inhibition of binding could be detected at 200 ng MutS and was complete at 5000 ng MutS.

2. Inhibition of Immobilized MutS Binding by HeLa Cell Extract

HeLa cell nuclear extract was purchased from Promega (Catalog No. E3091; HeLaScribe® Nuclear Extract, Transcription Grade). Increasing amounts (1–20 µg) of the HeLa nuclear extract were mixed with 2 ng Bio-Het DNA and incubated for 2 hours with gentle shaking at room temperature. This mixture was tested as above for the binding of the DNA to immobilized MutS.

The results shown in FIG. 9A and 9B, panel A, indicate that inhibition could be detected with 1 µg of extract and was complete at 5 µg.

To confirm that inhibition was due to DNA binding proteins and not to artifactual nuclease destruction of the DNA, the above mixtures were heated to 70° C. for 10 min. and cooled to room temperature for 30 min. This treatment is known to inactivate MutS and was intended to inactivate any other DNA binding proteins. The results shown in FIGS. 9A and 9B indicate that DNA (the signal in the immobilized MutS assay) was recovered from each mixture. However, the signed was reduced in proportion to the amount of extract present, indicating that both nuclease and DNA binding activities are present in the extract.

EXAMPLE VIII

Self-Annealing of Triplet Repeat Sequences

The ability of the triplet repeat sequences to form secondary structure was determined by self-annealing synthetic $(CXG)_{10}$ 30mer oligonucleotides with each of the four bases in the middle (X) position, and examining their behavior in polyacrylamide gel electrophoresis FIG. 10.

DNA in 10 mM Tris-HCl, pH 7.4, 1 mM EDTA was heated to 70° C. for 10 min., cooled 45 min to room temperature and then cooled to 4° C. DNA was stored at 4° C. A quantity of 10 ng DNA was loaded into each well of a gel apparatus in a volume of 5 µl consisting of 0.1 µl DNA solution, 4.1 µl of buffer (450 mM Tris-Borate, 1 mM EDTA) plus 0.8 µl of a 70% glycerol, 0.25% Bromophenol Blue solution. The gel was a 20% acrylamide/bis gel. The electrophoresis was performed at 75 volts for 2 hours at 4° C. and the gel stained with ethidium bromide. The results are shown in FIG. 10. Differential staining of single stranded oligonucleotides is presumably a result of oligonucleotide-dependent differences in the extent of ethidium bromide intercalation The results indicate that the formation of secondary structure is dependent on the nature of the center mismatched base pair. The CGG and CTG repeats self-annealed to form a duplex structure, whereas the CCG and CAG repeats did not.

EXAMPLE IX

Binding of Triplet Repeats to Immobilized MutS

The ability of the triplet repeat sequences to form secondary structure was further determined by assessing their interaction in binding assays with immobilized mismatch binding protein.

DNA was prepared as described in the Examples above. 500 ng E. coli MutS was bound to nitrocellulose as described above and the experiment carried out as in the previous Examples. The results are shown in FIG. 11. Self-annealed single stranded triplet repeat sequences of CGG and CTG formed double-stranded mismatch-containing DNA duplexes which were recognized by immobilized MutS. In contrast, immobilized MutS did not bind to CCG and CAG triplet repeat sequences under these conditions.

It is concluded that, with the triplet repeats used in these experiments, the density or frequency of mismatches prevents the formation of duplex structure in a mismatch-dependent fashion. However, once a duplex is formed, immobilized MutS appears to recognize the mismatches in that structure despite their density.

The results shown in Examples VI and VII support the notion that repeat blocks of unpaired sequences of the type CGG and CTG (but not CCG or CAG) can form stable hairpin secondary structures.

EXAMPLE X

Instructions for a Preferred Assay for Detection of Mutation, Heterozygosity or Polymorphism All steps are performed at room temperature.

1. Prepare MutS reaction buffer by adding 100 ml of 10× reaction buffer (200 mM Tris-HCl pH 7.6, 50 mM $MgCl_2$, 1 mM DTT, and 0.1 mM EDTA) to 900ml $ddH_2O$. Clarify with a 0.22 μm filter.
2. Cut nitrocellulose and 3 fiber pads (GB002 Schleicher & Schull) to fit within depression of Hoefer PR648 slot blot apparatus.
3. Float nitrocellulose on surface of a tray of reaction buffer for 2 minutes, then immerse by shaking. Keep immersed for 5 min.
4. Prepare MutS protein. Dilute in reaction buffer to 500 ng/20 μl. Vortex to mix.
5. Assemble slot blot apparatus, pouring off buffer squeezed from fiber pads. Pipet 100 μl of reaction buffer to all wells and pull through completely with vacuum.
6. Apply MutS solution, 20 μl (500 ng) to each well. Add equal volume of reaction buffer to "no MutS" wells. Incubate 20 min.
7. Prepare 3% HRP-free BSA (ICN) in reaction buffer. 30–40 ml are necessary for a full assay. Clarify with a 0.45 μm filter.
8. Pipet 200 μl of BSA to all wells. Incubate 1 hour, then pull through with vacuum.
9. Prepare DNA load samples. Use biotin labeled heteroduplex 30mer (Bio-het) as positive control, and biotin labeled homoduplex 30mer (Bio-homo) as a negative control. 1 or 5 ng are good control quantities. Dilute DNA in 3% HRP-free BSA, to 20 μl load volume.
10. Add DNA in 20 μl. Incubate 30 min.
11. Flick any residual DNA solution out of apparatus. Do not pull through. Wash 5×150 μl with reaction buffer, flicking each time.
12. Add 100 μl of 0.05 μg/ml streptavidin-HRP in 3% HRP-free BSA to each well. Incubate 20 min.
13. Flick off streptavidin-HRP solution. Wash 5×150 μl with reaction buffer, flicking each time. After last wash apply vacuum to pull through any residual liquid. Disassemble apparatus and transfer nitrocellulose to a tray containing 50 ml of reaction buffer. Immerse, pour off buffer, and add an additional 50 ml of reaction buffer, being careful not to pour buffer directly onto nitrocellulose. Repeat to wash a total of 5 times.

The following two steps, (14 and 15) are performed using the Enzygraphic web method. The IBI Enzygraphic® Web is a support polymer coated with the detection system required to detect enzyme activity (in this case, peroxidase). The Web is similar to autoradiography film in principle, structure and use, though it differs in that it detects peroxidase-linked probes under ordinary room light. The Web is a general peroxidase detection system useful to localize peroxidase labels in a variety of situations, including visualization of proteins on Western transfers and is various other forms of nucleic acid hybridization and DNA sequencing (whenever peroxidase-linked probes are used).

In the current embodiment, when the coated surface of the Web and the peroxidase-linked probe are brought together on a blot, a characteristic blue band rapidly forms within seconds and peaks within minutes at the location of the probe/target complex. Rapid and sensitive detection occurs via an electron transfer process initiated by peroxidase to the unique Web detection system.

14. Blot nitrocellulose dry. Apply 25 mls of 0.05% Tween in 10 mM Tris-Cl, 1 mM EDTA, pH 8.0. Gently shake for 3 min. Pour off Tween, rinse 4×50 mls with $ddH_2O$. Blot nitrocellulose keeping it damp. Apply Enzygraphic Web, frosted side down. Rub to be sure of proper contact. Develop for 3–6 min.
15. Carefully peel nitrocellulose from Web. Photocopy nitrocellulose, as color may change even after removal of web.

The following step (14) is performed in an alternative Enhanced Chemiluminescence assay, as described in the Examples above:

14. Blot nitrocellulose dry. Apply 10 ml ECL development solution (Amersham) for 1 min. Blot dry, place between overhead sheets, and expose to X-ray film for 15 to 300 seconds. 30 and 60 seconds are most typical exposure times.

EXAMPLE XI

Kits for Mismatch Detection

An example of a preferred kit for use in the methods described herein, sufficient to perform 100 assays, comprises the following components.

1. Cardboard Box, 5×6×4 inches, with custom insert.
2. *E. coli* MutS, 50 μg packaged in a 1.6 ml conical tube
3. BSA: 2 g HRP-free BSA in 4 ml Kimble glass vial
4. "Het", 100 ng, DNA heteroduplex 30mer with G-T mismatch, packaged in 0.5 ml eppendorf tube
5. "Homo", 100 ng, DNA homoduplex (perfectly matched) 30mer, packaged in 0.5 ml eppendorf tube
6. Streptavidin, 0.5 μg, conjugated with HRP, packaged in 0.5 ml eppendorf tube
7. 2 sheets Enzygraphic web (Kodak, Catalog No. 2K0750)
8. 2 sheets BA-85 nitrocellulose (Schleicher and Schull)
9. 50 X "RXTN": 40 ml of 50-X Reaction buffer packaged in a 60 ml Nalgene vial
10. 6 Fiber pads (blotting paper pads), Schleicher & Schuell Catalog no. GB002
11. 2 small (2"×3") and 2 large (4"×6") locking plastic bags (C-Line, Polyzip)

EXAMPLE XII

Detection of Minor Mutant DNA Contaminants in PCR Using MutS Immobilized on Magnetic Beads PCR was performed with 0.1 ng of template DNA cloned from the wild-type human glucokinase gene or a mutant (DGK10) human glucokinase gene. These genes are described above. In the segment examined, DGK10 has one nucleotide different from the wild-type gene. The ability of the method to detect minority DNA sequences was tested using in mixtures of wild type DNA artificially "contaminated" with 0%, 0.1%, 0.5%, 1%, and 2% DGK10 DNA. PCR was performed with one 5'-biotinylated primer and one non-biotinylated primer, which amplified a 187 bp product. Pfu polymerase (Stratagene) was used for touchdown PCR Touchdown PCR cycling parameters were as follows: denaturation; 94° C., 19 cycles, 1 minute; extension: 72° C., 2 minutes, with an additional 7 minute extension after the final PCR cycle. PCR products were purified with QIAquick® PCR purification kit (QIAGEN). Purified PCR products (150 ng, duplicate samples from each reaction) were denatured and reannealed: 100° C., 2 minutes; 50° C., 60 minutes; 75C, 2 minutes; 50° C., 30 minutes; cooled to room temperature over 30 minutes.

Denatured and reannealed DNA was added to MutS-coated magnetic beads in 3% PBSA (3% BSA in PBS) for 30 minutes with constant agitation. Beads were magnetically separated from the DNA solution and washed twice with reaction buffer (described above). Streptavidin (0.25 µg/ml) was added to the magnetic beads in 3% PBSA for 20 minutes with constant agitation Beads were magnetically separated from the solution, washed twice with reaction buffer, and TMB liquid substrate (Sigma) was added to the beads for 15 minutes. The reaction was terminated with 200 mM $H_2SO_4$, the solution was diluted with 5 volumes of water, and optical density at 450 nm ($OD_{450}$) was measured.

The results are shown in FIG. 14. The graph shows the average $OD_{450}$ of duplicate samples with background from beads that were not exposed to DNA subtracted. The assay is capable of detecting contamination of as little as 0.1% DNA of different sequence.

EXAMPLE XIII

Identification of a Specific Allele in Diploid DNA

The method is used to characterize sheep for susceptibility to scrapie, a prion disease related to Creutzfeld-Jacob disease in humans. In some breeds of sheep, a single mutation appears to confer resistance to scrapie. The mutation in codon 171 of the prion protein gene involves a switch from glutamine (Q) to arginine (R). Thus R/R and Q/R sheep appear to be resistant to scrapie, whereas Q/Q sheep appear to be susceptible.

PCR was performed on 40 ng of sheep DNA of known genotype QQ, RR and QR. In addition, 20 ng of QQ DNA was mixed with 20 ng of RR DNA prior to PCR. In separate tubes, 20 ng of QQ or RR DNA was mixed with 20 ng of QR DNA prior to PCR The unknown DNA (857) was mixed with known QQ or known RR DNA prior to amplification. 857 DNA alone was also subjected to amplification.

PCR was performed for 30 cycles using an upstream primer labeled at its 5' end with biotin and an unlabeled downstream primer. The primers amplify a 190 bp fragment of the sheep PrP gene. DNA was purified on QIAquick® columns (Qiagen) to remove primers, and eluted in 10 mM Tris-HCl pH 8.5, 100 mM NaCl. DNA was then denatured and annealed by heating to 100° C. for 3 minutes followed by cooling to 50° C. for 60 min, 75° C. for 5 min, and 50° C. for an additional 30 min. Each product (6.25 ng or 12.5 ng) was tested for the presence of mismatches using the immobilized MutS assay described herein.

The results are shown in FIG. 16. Negative signals were observed with QQ, RR, 857 and 857+QQ. Positive results were observed for QQ+RR, QR+QQ, QR+RR and 857+RR. It can therefore be concluded that 857 is of the genotype QQ.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

---

What is claimed is:

1. A method for determining the presence of a functional mismatch-binding protein in a biological fluid sample comprising:

(a) mixing the biological fluid sample with a detectably labeled heteroduplex DNA to form a mixture;

(b) contacting said mixture with an immobilized mismatch-binding protein;

(c) detecting the binding of any heteroduplex DNA to said immobilized mismatch-binding protein; and (d) comparing the amount of heteroduplex DNA bound with an amount bound when steps (a) through (c) are separately performed using a control sample in place of the biological fluid sample, wherein a reduced amount of bound heteroduplex DNA in the presence of the biological fluid sample relative to the control sample is indicative of the presence of a functional mismatch-binding protein in the biological fluid sample.

2. The method of claim 1, wherein said immobilized mismatch-binding protein is *E. coli* MutS protein or a homologue thereof from a different prokaryotic or eukaryotic species.

3. A method for detecting the presence of a triplet repeat block of unit sequence $$\frac{5'\text{-CGG}_n}{3'\text{-GCC}_n} \text{ or } \frac{5'\text{-CTG}_n}{3'\text{-GAC}_n}$$

in test DNA in a sample, which block is longer than a triplet repeat block in a diagnostic oligonucleotide probe, which method comprises:

(a) incubating the test DNA with a detectably labeled single stranded diagnostic oligonucleotide probe having a unit triplet repeat sequence 3'-GCC$_m$ or 3'-GAC$_m$, respectively, wherein (i) n is the number of repeats of the triplet repeat block of said test DNA (ii) m is the number of repeats of the triplet repeat block of said probe, and (iii) n and m are integers;

(b) denaturing any double stranded DNA in the mixture of step (a) into single strands and allowing said strands to reanneal;

(c) incubating the mixture of step (b) with an immobilized mismatch binding protein; and (d) detecting the binding of any detectably labeled DNA to said immobilized mismatch binding protein, wherein the presence of bound detectably labeled DNA is indicative of the presence in said test DNA of a triplet repeat block with a repeat number n greater than m so as to detect the presence of a triplet repeat block of unit sequence $$\frac{5'\text{-CGG}_n}{3'\text{-GCC}_n} \text{ or } \frac{5'\text{-CTG}_n}{3'\text{-GAC}_n}$$

in test DNA in a sample, which block is longer than a triplet repeat block in a diagnostic oligonucleotide probe.

4. A method for detecting the presence of a triplet repeat block of unit sequence $$\frac{5'\text{-CGG}_n}{3'\text{-GCC}_n} \text{ or } \frac{5'\text{-CTG}_n}{3'\text{-GAC}_n}$$

in test DNA in a sample, which block is shorter than a triplet repeat block in a diagnostic oligonucleotide probe, which method comprises:

(a) incubating the test DNA with a detectably labeled single stranded diagnostic oligonucleotide probe having a unit triplet repeat sequence 5'-CGG$_m$ or 5'-CTG$_m$, respectively, wherein (i) n is the number of repeats of the triplet repeat block of said test DNA, (ii) m is the number of repeats of the triplet, repeat block of said probe, and (iii) n and m are integers;

(b) denaturing any double stranded DNA in the mixture of step (a) into single strands and allowing said strands to reanneal;

(c) incubating the mixture of step (b) with an immobilized mismatch binding protein; and (d) detecting the binding of any detectably labeled DNA to said immobilized mismatch binding protein, wherein the presence of bound detectably labeled DNA is indicative of the presence in said test DNA of a triplet repeat block with a repeat number n less than m so as to detect the presence of a triplet repeat block of unit sequence $$\frac{5'\text{-CGG}_n}{3'\text{-GCC}_n} \text{ or } \frac{5'\text{-CTG}_n}{3'\text{-GAC}_n}$$

in test DNA in a sample, which block is shorter than a triplet repeat block in a diagnostic oligonucleotide probe.

5. The method of claim 3 or claim 4, wherein the test DNA is amplified prior to step (a).

6. The method of claim 3 or claim 4 wherein said immobilized mismatch-binding protein is *E. coli* MutS protein or a homologue thereof from a different prokaryotic or eukaryotic species.

7. The method of claim 3 or claim 4, wherein the test DNA is obtained from an individual at risk for developing or transmitting a disease or syndrome associated with triplet repeats.

8. The method of claim 7, where in the disease or syndrome is selected from the group consisting of fragile X syndrome type A, fragile X syndrome type E, myotonic dystrophy, Huntington's disease, spino-cerebellar ataxia type I, spinal bulbar muscular atrophy, Machado-Joseph disease and dentatorubralpallidoluysian atrophy.

9. A competitive assay method for detecting the presence of a triplet repeat block of unit sequence

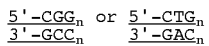

in test DNA in a sample, which block is longer than a triplet repeat block in a diagnostic oligonucleotide probe, which method comprises:
  (a) incubating the test DNA with a single stranded diagnostic oligonucleotide probe having a unit triplet repeat sequence 3'-$GCC_m$ or 3'-$GAC_m$, respectively, wherein
    (i) n is the number of repeats of the triplet repeat block of said test DNA,
    (ii) m is the number of repeats of the triplet repeat block of said probe, and
    (iii) n and m are integers;
  (b) incubating the duplexes formed in step (a) with an immobilized mismatch binding protein, either
    (i) in the presence of a detectably labeled mismatch-containing double stranded oligonucleotide, or
    (ii) wherein said protein was preincubated with and allowed to bind to a detectably labeled mismatch-containing double stranded oligonucleotide,
    under conditions in which heteroduplexes containing a mismatch or one to four unpaired bases bind to said immobilized protein; and
  (c) detecting the amount of detectably labeled mismatch-containing oligonucleotide bound to said immobilized protein,
wherein reduced binding relative to the amount bound in the absence of the duplexes is indicative of the presence in said test DNA of a triplet repeat block with a repeat number n greater than m so as to detect the presence of a triplet repeat block of unit sequence

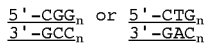

in test DNA in a sample, which block is longer than a triplet repeat block in a diagnostic oligonucleotide probe.

10. A competitive assay method for detecting the presence of a triplet repeat block of unit sequence

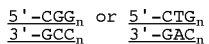

in test DNA in a sample, which block is shorter than a triplet repeat block in a diagnostic oligonucleotide probe, which method comprises:
  (a) incubating the test DNA with a single stranded diagnostic oligonucleotide probe having a unit triplet repeat sequence 5'-$CGG_m$ or 5'-$CTG_m$, respectively, wherein
    (i) n is the number of repeats of the triplet repeat block of said test DNA
    (ii) m is the number of repeats of the triplet repeat block of said probe, and
    (iii) n and m are integers;
  (b) incubating the duplexes formed in step (a) with an immobilized mismatch binding protein, either
    (i) in the presence of a detectably labeled mismatch-containing double stranded oligonucleotide, or
    (ii) wherein said protein was preincubated with and allowed to bind to a detectably labeled mismatch-containing double stranded oligonucleotide,
    under conditions in which heteroduplexes containing a mismatch or one to four unpaired bases bind to said immobilized protein; and
  (c) detecting the amount of detectably labeled mismatch-containing oligonucleotide bound to said immobilized protein,
wherein reduced binding relative to the amount bound in the absence of the duplexes is indicative of the presence in said test DNA of a triplet repeat block with a repeat number n less than m so as to detect the presence of a triplet repeat block of unit sequence

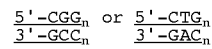

in test DNA in a sample, which block is shorter than a triplet repeat block in a diagnostic oligonucleotide probe.

11. The method of claim 9 or claim 10, wherein the test DNA is amplified prior to step (a).

12. The method of claim 9 or claim 10, wherein said immobilized mismatch-binding protein is *E. coli* MutS protein or a homologue thereof from a different prokaryotic or eukaryotic species.

13. The method of claim 9 or claim 10, wherein the test DNA is obtained from an individual at risk for developing or transmitting a disease or syndrome associated with triplet repeats.

14. The method of claim 13, wherein the disease or syndrome is selected from the group consisting of fragile X syndrome type A, fragile X syndrome type E, myotonic dystrophy, Huntington's disease, spino-cerebellar ataxia type I, spinal bulbar muscular atrophy, Machado-Joseph disease and dentatorubralpallidoluysian atrophy.

15. A method for detecting the presence of a repeat block in a test DNA, which repeat block is longer than a repeat block in a diagnostic oligonucleotide probe, which method comprises:
  (a) determining a unit repeat sequence of the repeat block in the test DNA, wherein the unit repeat sequence but not its complement forms secondary structure which binds to an immobilized mismatch binding protein;
  (b) mixing the test DNA with the diagnostic oligonucleotide probe, which probe is detectably labeled and has a nucleotide sequence complementary to the unit repeat sequence;
  (c) denaturing any double-stranded DNA in the mixture of step (b) into single strands and allowing said strands to reanneal;
  (d) contacting the mixture of step (c) with an immobilized mismatch binding protein; and
  (e) detecting the binding of any detectably-labeled DNA to the immobilized mismatch binding protein,
wherein the presence of bound detectably-labeled DNA is indicative of the presence in the test DNA of a repeat block longer than the repeat block in the diagnostic oligonucleotide probe.

16. The method of claim 15, wherein the test DNA is amplified prior to step (a).

17. The method of claim 15, wherein the immobilized mismatch-binding protein is *E. coli* MutS protein or a homologue thereof from a different prokaryotic or eukaryotic species.

18. The method of claim 15, wherein the test DNA is obtained from an individual at risk for developing or transmitting a disease or syndrome associated with triplet repeats.

19. The method of claim 18, wherein the disease or syndrome is selected from the group consisting of fragile X syndrome type A, fragile X syndrome type E, myotonic dystrophy, Huntington's disease, spino-cerebellar ataxia type I, spinal bulbar muscular atrophy, Machado-Joseph disease and dentatorubralpallidoluysian atrophy.

20. The method of claim 2, wherein said immobilized mismatch-binding protein is *E. coli* MutS protein.

21. The method of claim 2, wherein said immobilized mismatch-binding protein is a homologue of *E. coli* MutS protein from a different prokaryotic species.

22. The method of claim 2, wherein said immobilized mismatch-binding protein is a homologue of *E. coli* Mut S.

23. The method of claim 3, wherein the test DNA is amplified prior to step (a).

24. The method of claim 4, wherein the test DNA is amplified prior to step (a).

25. The method of claim 3, wherein said immobilized mismatch-binding protein is *E. coli* MutS protein.

26. The method of claim 3, wherein said immobilized mismatch-binding protein is a homologue of *E. coli* MutS protein from a different prokaryotic species.

27. The method of claim 3, wherein said immobilized mismatch-binding protein is *E. coli* MutS protein.

28. The method of claim 4, wherein said immobilized mismatch-binding protein is *E. coli* MutS protein.

29. The method of claim 4, wherein said immobilized mismatch-binding protein is a homologue of *E. coli* MutS protein from a different prokaryotic species.

30. The method of claim 4, wherein said immobilized mismatch-binding protein is a homologue of *E. coli* MutS protein from an eurkaryotic species.

31. The method of claim 3, wherein the test DNA is obtained from an individual at risk for developing a disease or syndrome associated with triplet repeats.

32. The method of claim 3, wherein the test DNA is obtained from an individual at risk for transmitting a disease or syndrome associated with triplet repeats.

33. The method of claim 4, wherein the DNA is obtained from an individual risk for developing a disease or syndrome associated with triplet repeats.

34. The method of claim 4, wherein the test DNA is obtained from an individual risk for transmitting a disease or syndrome associated with triplet repeats.

35. The method of claim 3, wherein the test DNA is obtained from an individual at risk for developing or transmitting fragile X syndrome type A.

36. The method of claim 3, wherein the test DNA is obtained from an individual at risk for developing or transmitting fragile X syndrome type E.

37. The method of claim 3, wherein the test DNA is obtained from an individual at risk for developing or transmitting myotonic dystrophy.

38. The method of claim 3, wherein the test DNA is obtained from an individual at risk for developing or transmitting Huntington's disease.

39. The method of claim 3, wherein the test DNA is obtained from an individual at risk for developing or transmitting spino-cerebellar ataxia type I.

40. The method of claim 3, wherein the test DNA is obtained from an individual at risk for developing or transmitting spinal bulbar muscular atrophy.

41. The method of claim 3, wherein the test DNA is obtained from an individual at risk for developing or transmitting Machado-Joseph disease.

42. The method of claim 3, wherein the test DNA is obtained from an individual at risk for developing or transmitting dentatorubralpallidoluysian atrophy.

43. The method of claim 4, wherein the test DNA is obtained from an individual at risk for developing or transmitting fragile X syndrome type A.

44. The method of claim 4, wherein the test DNA is obtained from an individual at risk for developing or transmitting fragile X syndrome type E.

45. The method of claim 4, wherein the test DNA is obtained from an individual at risk for developing or transmitting myotonic dystrophy.

46. The method of claim 4, wherein the test DNA is obtained from an individual at risk for developing or transmitting Huntington's disease.

47. The method of claim 4, wherein the test DNA is obtained from an individual at risk for developing spino-cerebellar ataxia type I.

48. The method of claim 4, wherein the test DNA is obtained from an individual at risk for developing or transmitting spinal bulbar muscular atrophy.

49. The method of claim 4, wherein the test DNA is obtained from an individual at risk for developing or transmitting Machado-Joseph disease.

50. The method of claim 4, wherein the test DNA is obtained from an individual at risk for developing or transmitting dentatorubralpallidoluysian atrophy.

51. The method of claim 9, wherein the test DNA is amplified prior to step (a).

52. The method of claim 10, wherein the test DNA is amplified prior to step (a).

53. The method of claim 9, wherein said immobilized mismatch-binding protein *E. coli* MutS protein.

54. The method of claim 9, wherein said immobilized mismatch-binding protein is a homologue of *E. coli* MutS protein from a different prokaryotic species.

55. The method of claim 9, wherein said immobilized mismatch-binding protein is a homologue of *E. coli* MutS protein from an eukaryotic species.

56. The method of claim 10, wherein said immobilized mismatch-binding protein is *E. coli* MutS protein.

57. The method of claim 10, wherein said immobilized mismatch-binding protein is a homologue of *E. coli* MutS protein from a different prokaryotic species.

58. The method of claim 10, wherein said immobilized mismatch-binding protein is a homologue of *E. coli* MutS protein from an eukaryotic species.

59. The method of claim 9, wherein the test DNA is obtained from an individual at risk for developing a disease or syndrome associated with triplet repeats.

60. The method of claim 9, wherein the test DNA is obtained from an individual at risk for transmitting a disease or syndrome associated with triplet repeats.

61. The method of claim 10, wherein the test DNA is obtained from an individual at risk for developing a disease or syndrome associated with triplet repeats.

62. The method of claim 10, wherein the test DNA is obtained from an individual at risk for transmitting a disease or syndome associated with triplet repeats.

63. The method of claim 9, wherein the test DNA is obtained from an individual at risk for developing or transmitting fragile X syndrome type A.

64. The method of claim 9, wherein the test DNA is obtained from an individual at risk for developing or transmitting fragile X syndrome type E.

65. The method of claim 9, wherein the test DNA is obtained from an individual at risk for developing or transmitting myotinic dystrophy.

66. The method of claim 9, wherein the test DNA is obtained from an individual at risk for developing or transmitting Huntington's disease.

67. The method of claim 9, wherein the test DNA is obtained from an individual at risk for developing or transmitting spino-cerebellar ataxia type I.

68. The method of claim 9, wherein the test DNA is obtained from an individual at risk for developing or transmitting spinal bulbar muscular atrophy.

69. The method of claim 9, wherein the test DNA is obtained from an individual at risk for developing or transmitting Machado-Joseph disease.

70. The method of claim 9, wherein the test DNA is obtained from an individual at risk for developing or transmitting dentatorupallidoluysian atrophy.

71. The method of claim 10, wherein the test DNA is obtained from an individual at risk for developing or transmitting fragile X syndrome type A.

72. The method of claim 10, wherein the test DNA is obtained from an individual at risk for developing or transmitting fragile X syndrome type E.

73. The method of claim 10, wherein the test DNA is obtained from an individual at risk for developing or transmitting myotonic dystrophy.

74. The method of claim 10, wherein the test DNA is obtained from an individual at risk for developing or transmitting Huntington's disease.

75. The method of claim 10, wherein the test DNA is obtained from an individual at risk for developing or transmitting spino-cerebellar ataxia type I.

76. The method of claim 10, wherein the test DNA is obtained from an individual at risk for developing or transmitting spinal bulbar muscular atrophy.

77. The method of claim 10, wherein the test DNA is obtained from an individual at risk for developing or transmitting Machado-Joseph disease.

78. The method of claim 10, wherein the test DNA is obtained from an individual at risk for developing or transmitting dentatorubralpallidoluysian atrophy.

79. The method of claim 17, wherein the immobilized mismatch-binding protein is *E. coli* MutS protein.

80. The method of claim 17, wherein the immobilized mismatch-binding protein is a homologue of *E. coli* MutS protein from a different prokaryotic species.

81. The method of claim 17, wherein the immobilized mismatch-binding protein is a homologue of *E. coli* MutS protein from an eurkaryotic species.

82. The method of claim 18, wherein the test DNA is obtained from an individual at risk for developing a disease or syndrome associated with triplet repeats.

83. The method of claim 18, wherein the test DNA is obtained from an individual risk for transmitting a disease or syndrome associated with triplet repeats.

84. The method of claim 18, wherein the disease or syndrome is fragile X syndrome type A.

85. The method of claim 18, wherein the disease or syndrome is fragile X syndrome type E.

86. The method of claim 18, wherein the disease or syndrome is myotonic dystrophy.

87. The method of claim 18, wherein the disease or syndrome is Huntington's disease.

88. The method of claim 18, wherein the disease or syndrome is spino-cerebellar ataxia type I.

89. The method of claim 18, wherein the disease or syndrome is spinal bulbar muscular atrophy.

90. The method of claim 18, wherein the disease or syndrome is Machado-Joseph disease.

91. The method of claim 18, wherein the disease or syndrome is dentatorubralpallidoluysian atrophy.

* * * * *